United States Patent
West et al.

(10) Patent No.: US 7,615,049 B2
(45) Date of Patent: Nov. 10, 2009

(54) DEVICES, SYSTEMS AND METHODS FOR TREATING TISSUE REGIONS OF THE BODY

(75) Inventors: Scott West, Livermore, CA (US); John W. Gaiser, Mountain View, CA (US); Robin Bek, Campbell, CA (US); David S. Utley, Redwood City, CA (US); Patrick Rimroth, San Jose, CA (US)

(73) Assignee: Mederi Therapeutics, Inc., Cos Cob, CT (US)

( * ) Notice: Subject to any disclaimer, the term of this patent is extended or adjusted under 35 U.S.C. 154(b) by 481 days.

(21) Appl. No.: 11/055,450

(22) Filed: Feb. 9, 2005

(65) Prior Publication Data

US 2005/0154386 A1    Jul. 14, 2005

Related U.S. Application Data

(60) Continuation of application No. 10/872,656, filed on Jun. 21, 2004, now abandoned, which is a continuation-in-part of application No. 10/760,433, filed on Jan. 20, 2004, now Pat. No. 7,179,257, which is a division of application No. 09/955,915, filed on Sep. 19, 2001, now Pat. No. 6,699,243.

(60) Provisional application No. 60/480,147, filed on Jun. 20, 2003.

(51) Int. Cl.
*A61B 18/18* (2006.01)
*A61M 29/00* (2006.01)

(52) U.S. Cl. .......................... 606/41; 607/101; 606/191
(58) Field of Classification Search ................... 606/41, 606/45–50, 191–194; 607/101, 102, 122; 604/101–104
See application file for complete search history.

(56) References Cited

U.S. PATENT DOCUMENTS

| | | | | |
|---|---|---|---|---|
| 5,345,936 | A | * | 9/1994 | Pomeranz et al. ........... 600/374 |
| 5,370,675 | A | | 12/1994 | Edwards et al. |
| 5,454,782 | A | | 10/1995 | Perkins |
| 5,549,661 | A | * | 8/1996 | Kordis et al. .................. 607/99 |
| 5,588,960 | A | | 12/1996 | Edwards et al. |
| 6,006,755 | A | | 12/1999 | Edwards |
| 6,009,877 | A | | 1/2000 | Edwards |
| 6,016,452 | A | | 1/2000 | Kasevich |
| 6,036,689 | A | * | 3/2000 | Tu et al. ....................... 606/41 |
| 6,044,846 | A | | 4/2000 | Edwards |
| 6,056,744 | A | | 5/2000 | Edwards |
| 6,092,528 | A | | 7/2000 | Edwards |
| 6,254,598 | B1 | * | 7/2001 | Edwards et al. ............... 606/41 |
| 6,258,087 | B1 | | 7/2001 | Edwards et al. |
| 6,355,031 | B1 | | 3/2002 | Edwards et al. |
| 6,405,732 | B1 | | 6/2002 | Edwards et al. |
| 6,423,058 | B1 | * | 7/2002 | Edwards et al. ............... 606/41 |

(Continued)

FOREIGN PATENT DOCUMENTS

WO    WO 99/35986    7/1999

(Continued)

*Primary Examiner*—Michael Peffley
(74) *Attorney, Agent, or Firm*—Ryan Kromholz & Manion S.C.

(57) ABSTRACT

Improved devices, systems and methods for treating a tissue region provide straightforward, yet reliable ways for installing diverse functional components within the confined space of a catheter-based instrument.

4 Claims, 52 Drawing Sheets

U.S. PATENT DOCUMENTS

| | | | |
|---|---|---|---|
| 6,464,689 | B1 | 10/2002 | Qin et al. |
| 6,464,697 | B1 | 10/2002 | Edwards et al. |
| 6,544,226 | B1 | 4/2003 | Gaiser et al. |
| 6,547,776 | B1 | 4/2003 | Gaiser et al. |
| 6,589,238 | B2 | 7/2003 | Edwards et al. |
| 6,645,201 | B1 | 11/2003 | Utley et al. |
| 6,699,243 | B2 | 3/2004 | West et al. |
| 6,733,495 | B1 | 5/2004 | Bek et al. |
| 6,783,523 | B2 | 8/2004 | Qin et al. |
| 6,790,207 | B2 | 9/2004 | Utley et al. |
| 6,802,841 | B2 | 10/2004 | Utley et al. |
| 2002/0120262 | A1 | 8/2002 | Bek et al. |
| 2002/0151871 | A1 | 10/2002 | Gaiser et al. |
| 2002/0162555 | A1 | 11/2002 | West et al. |
| 2004/0089313 | A1 | 5/2004 | Utley et al. |

FOREIGN PATENT DOCUMENTS

| | | |
|---|---|---|
| WO | WO 01/05318 | 1/2001 |
| WO | WO 02/28303 | 4/2002 |

\* cited by examiner

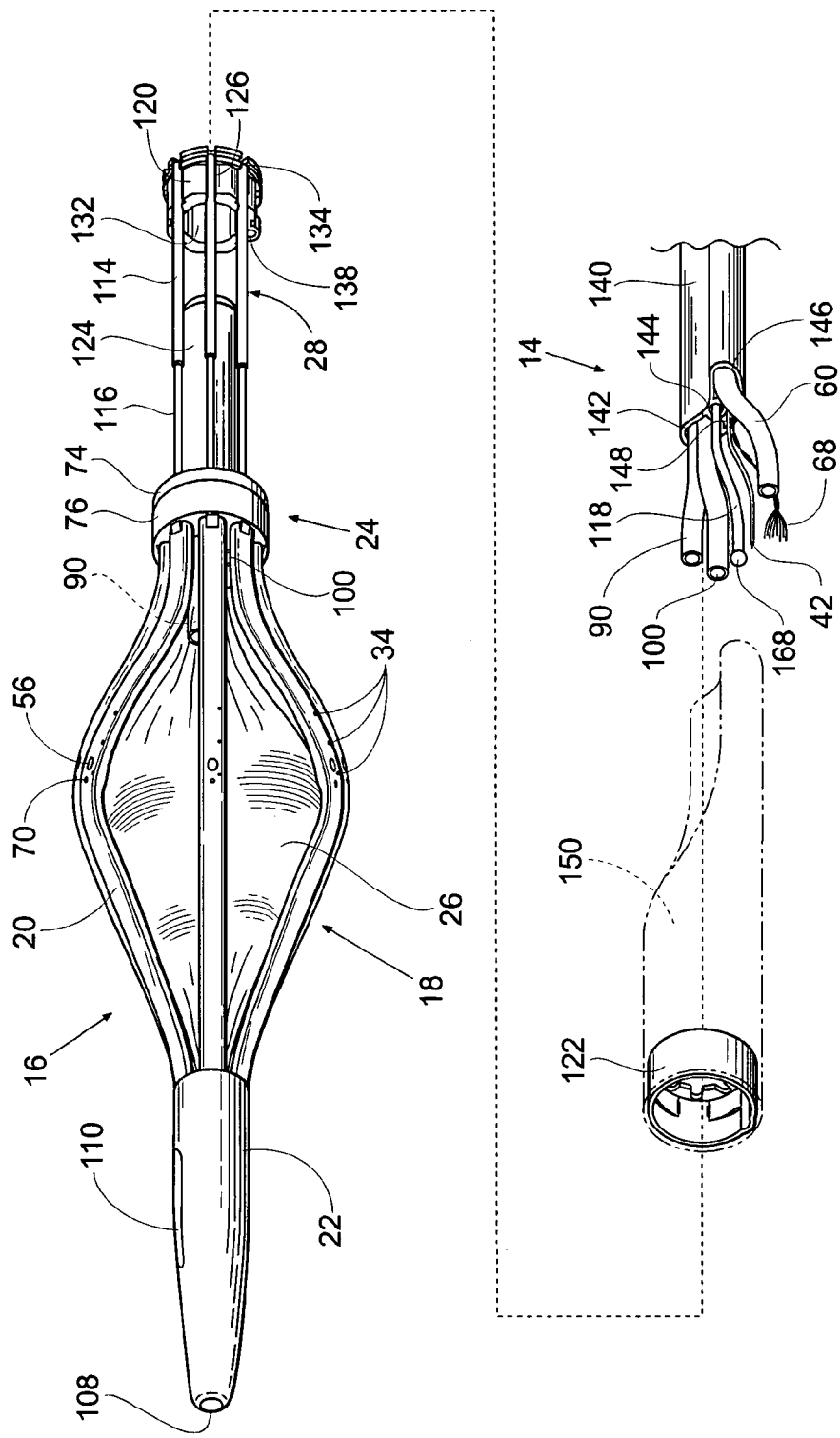

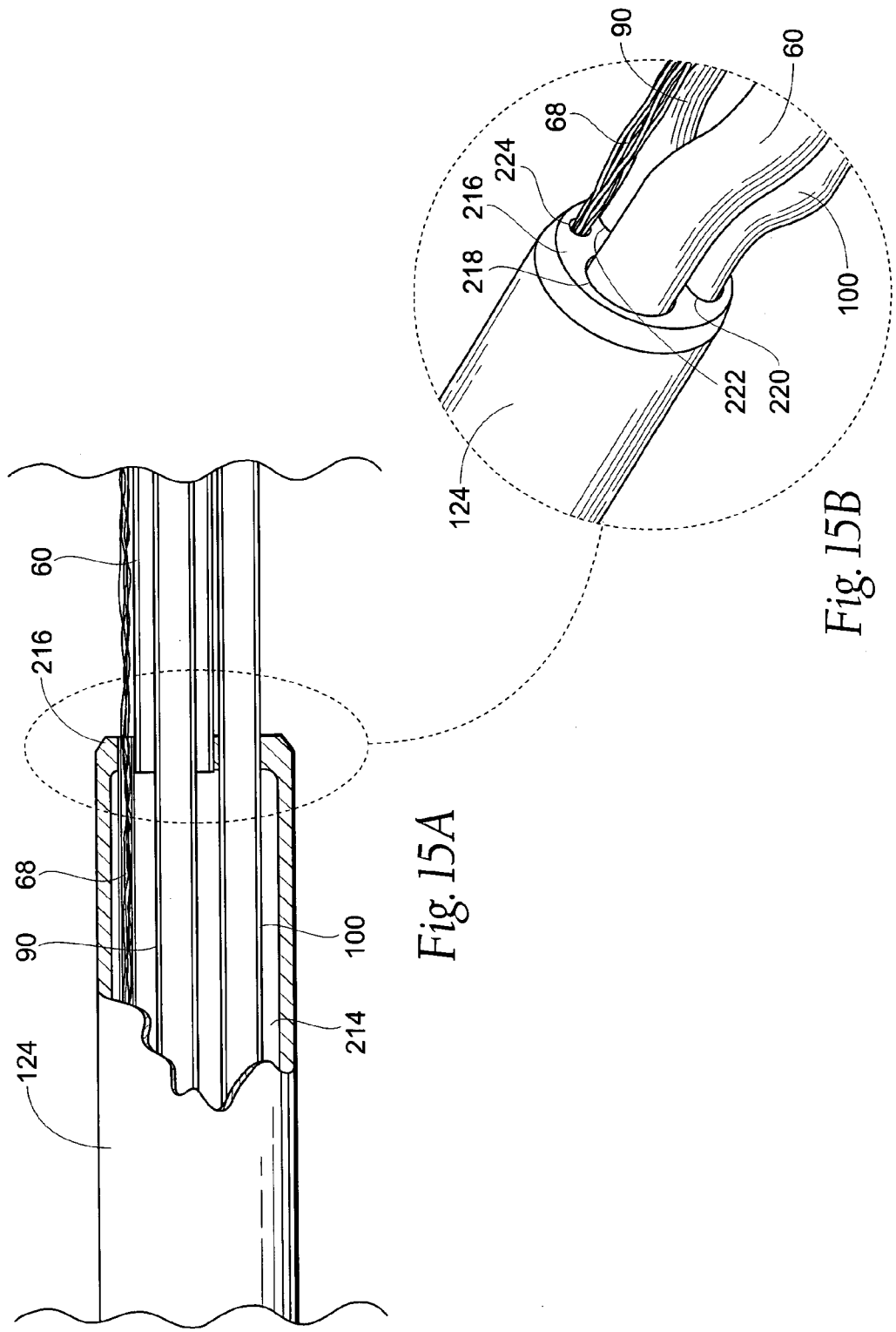

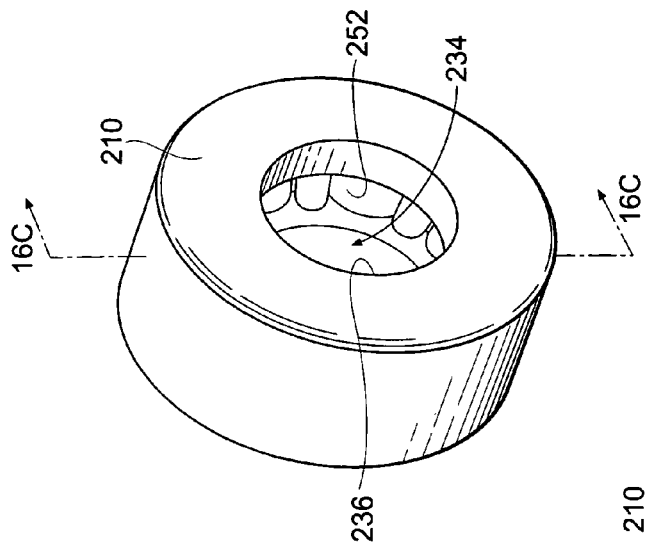
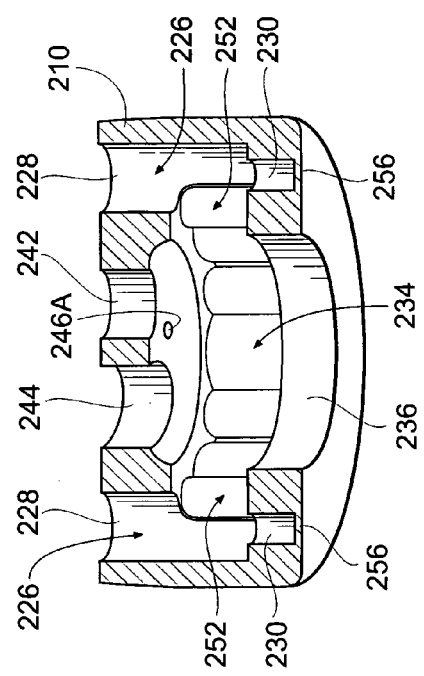
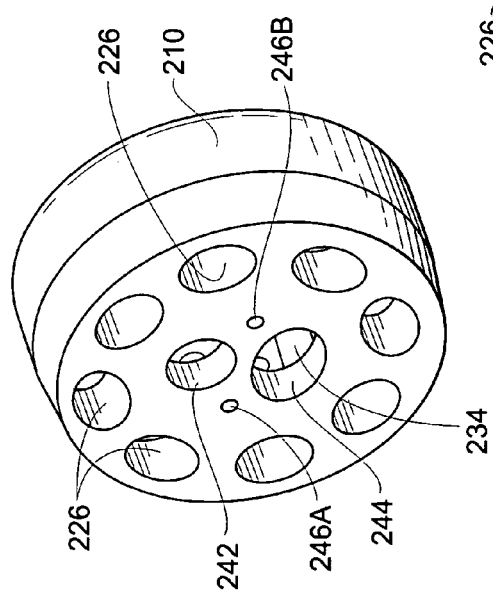
Fig. 16B
Fig. 16C
Fig. 16A

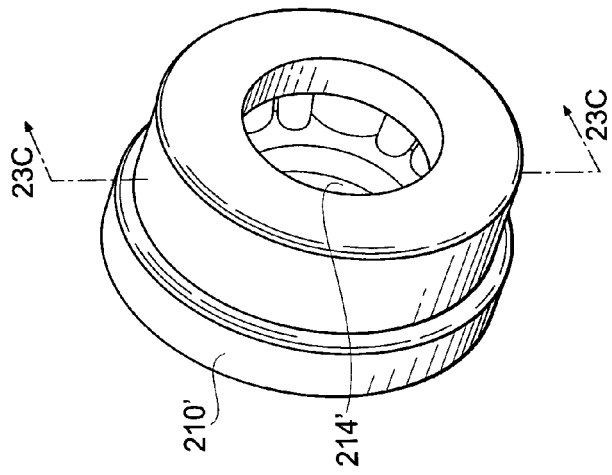
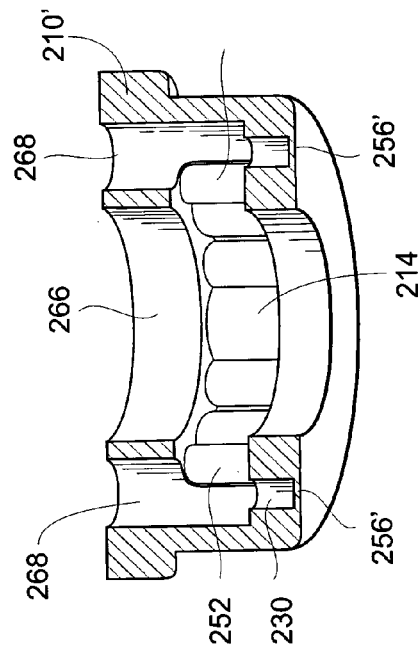
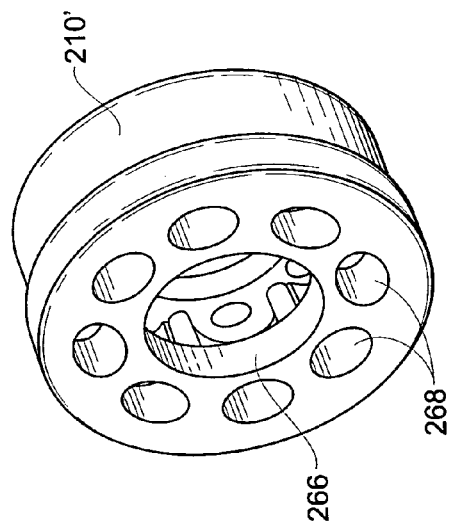

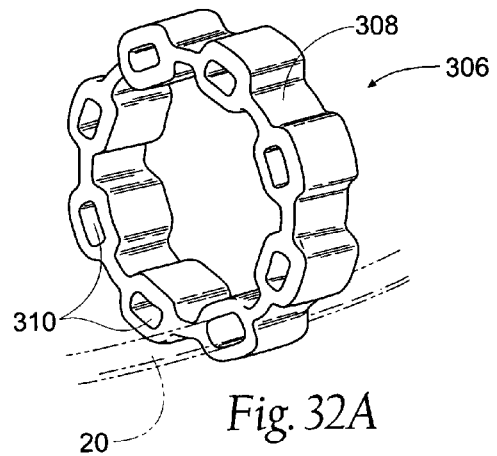
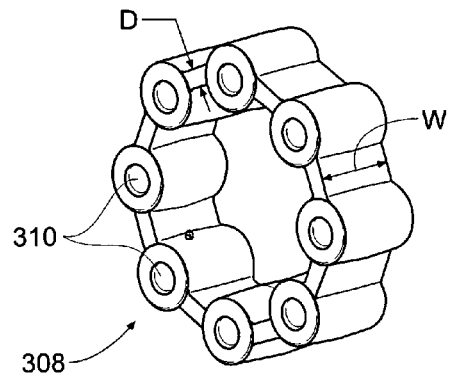
Fig. 32A  Fig. 32D
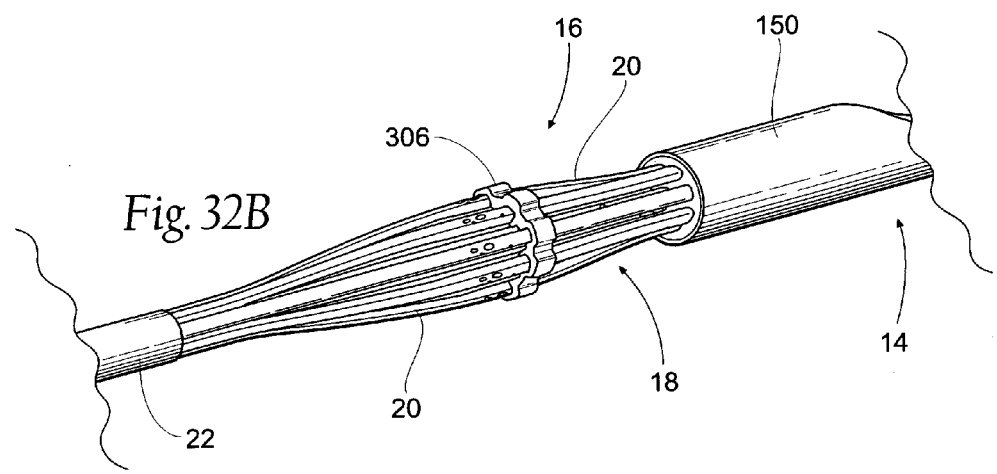
Fig. 32B
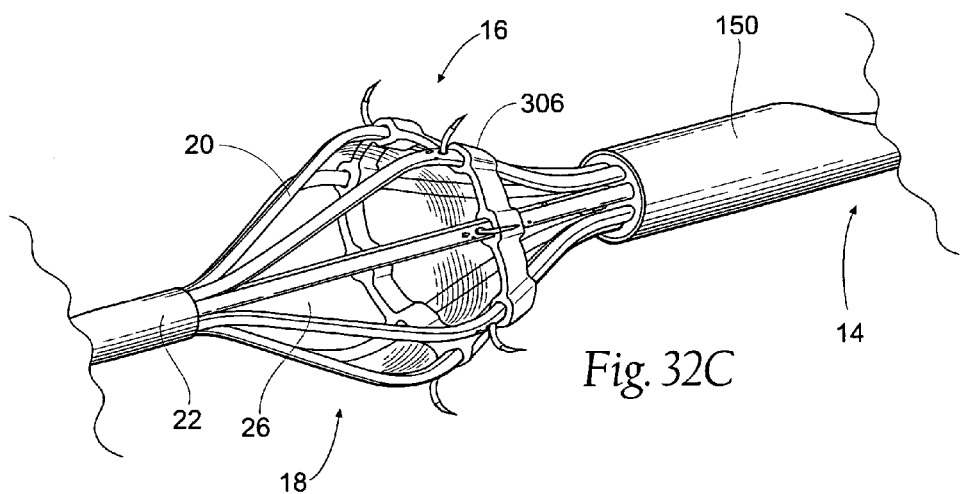
Fig. 32C

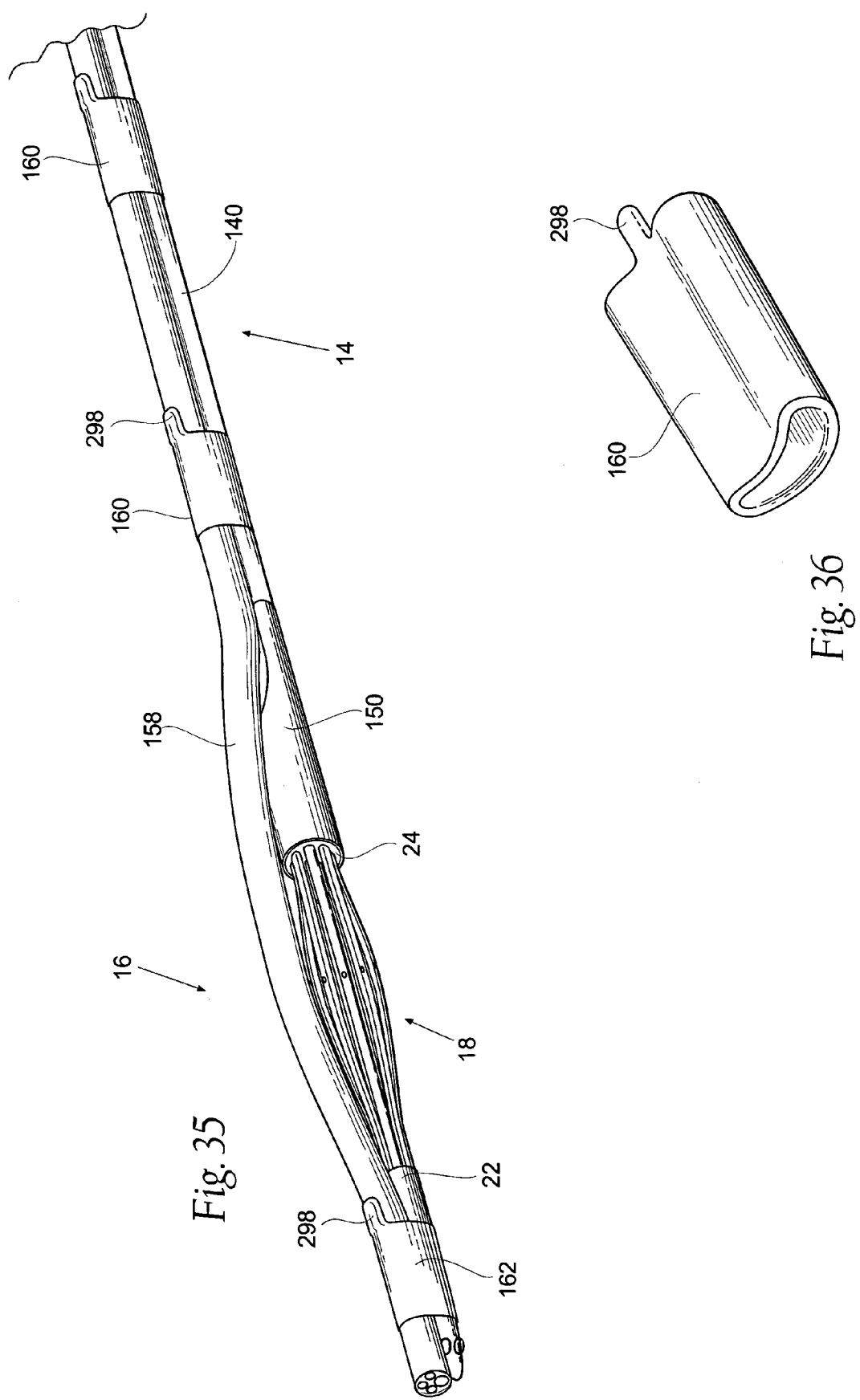

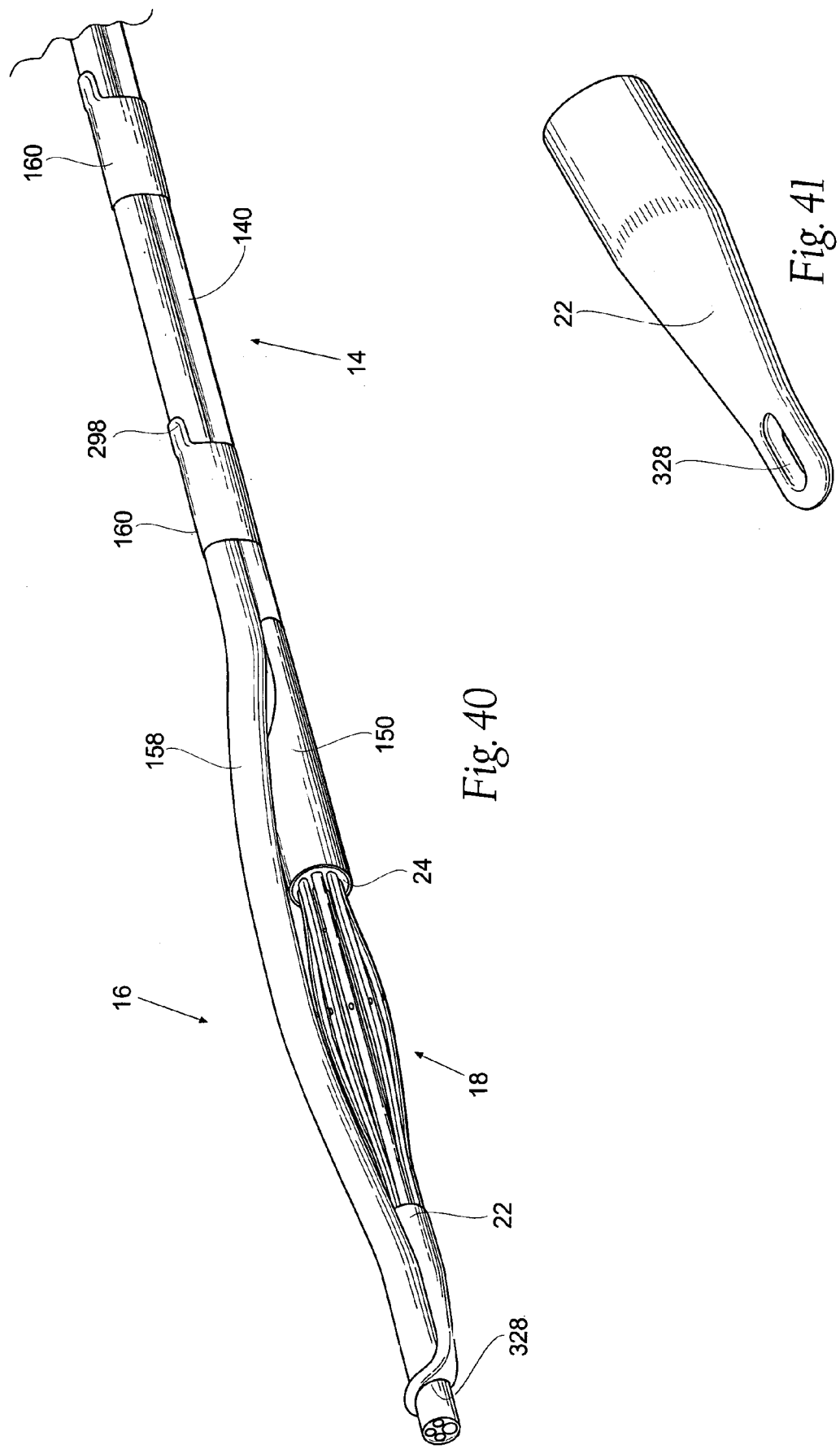

DEVICES, SYSTEMS AND METHODS FOR TREATING TISSUE REGIONS OF THE BODY

RELATED APPLICATIONS

This application is a continuation of U.S. application Ser. No. 10/872,656, filed Jun. 21, 2004 (now abandoned), which claims the benefit of provisional U.S. application Ser. No. 60/480,147, filed Jun. 20, 2003, and which is also a continuation in part of U.S. application Ser. No. 10/760,433, filed Jan. 20, 2004, now U.S. Pat. No. 7,179,257, which is a divisional of U.S. application Ser. No. 09/955,915, filed Sep. 19, 2001, now U.S. Pat. No. 6,699,243.

FIELD OF THE INVENTION

The invention is directed to devices, systems and methods for treating tissue regions of the body.

BACKGROUND OF THE INVENTION

Catheter based instruments are widely used to gain access to interior body regions for diagnostic or therapeutic purposes. The size of such instruments are constrained by the need to permit deployment and use within relatively small, confined areas of the body. Still, there is the need for such instruments to carry one or more functional components, e.g., to ablate body tissue and/or to convey fluid into contact with tissue in the targeted tissue region and/or to sense local tissue conditions, etc.

The challenge persists in accommodating the need for small, easily deployed catheter-based instruments with the demand for reliable and robust functionality.

SUMMARY OF THE INVENTION

The invention provides improved devices, systems and methods for treating a tissue region that provide straightforward, yet reliable ways for installing diverse functional components within the confined space of a catheter-based instrument.

BRIEF DESCRIPTION OF THE DRAWINGS

FIG. 3C is a further partially assembled view of the operative element shown in FIG. 3B, showing the assemblage of the electrode advancer assembly to the expandable basket structure shown in FIG. 3B.

FIG. 15A is an enlarged side section view of the proximal end of the stem of the electrode advancer assembly of the operative element shown in FIGS. 13 and 14, showing the routing of related electrical and fluid conveyance components through the stem to enable "direct irrigation".

FIG. 15B is an enlarged perspective view of the proximal end of the stem shown in FIG. 15A.

FIGS. 16A, 16B, and 16C are, respectively, a distal end perspective view, a proximal end perspective view, and a side section view of the irrigation seal member that the operative element shown in FIGS. 13 and 14 employs to support and seal the basket arms and electrode elements, as well as distribute irrigation fluid into the lumens of the basket arms that carry the electrode elements, thereby enabling "direct irrigation".

FIGS. 23A, 23B, and 23C are, respectively, a distal end perspective view, a proximal end perspective view, and a side section view of the irrigation seal member that the operative element shown in FIGS. 20 to 21 employs to support and seal the basket arms and electrode elements, as well as distribute irrigation fluid into the lumens of the basket arms that carry the electrode elements, thereby enabling "direct irrigation".

FIGS. 32A, 32B, and 32C are perspective views of an operative element of the type shown in FIG. 31, and in which the resilient component comprises an elastomeric band.

FIG. 32D is a perspective view of an alternative embodiment of an elastomeric band.

FIG. 35 is a perspective view of an operative element of the type shown in FIGS. 2A to 2C, and further including guide sheaths to enable an endoscopic element to be tethered to the operative element in a piggy-back fashion for use.

FIG. 36 is an enlarged perspective view of a guide sheath shown in FIG. 35.

FIG. 40 is a perspective view of an operative element of the type shown in FIGS. 2A to 2C, and further including a slotted distal tip to enable an endoscopic element to be tethered to the operative element in a piggy-back fashion for use.

FIG. 41 is an enlarged perspective view of the slotted distal tip shown in FIG. 40.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification discloses various catheter-based systems and methods for treating dysfunction in various locations in an animal body. For example, the various aspects of the invention have application in procedures requiring treatment of sphincters and adjoining tissue regions in the body, or hemorrhoids, or incontinence, or obesity, or restoring compliance to or otherwise tightening interior tissue or muscle regions. The systems and methods that embody features of the invention are also adaptable for use with systems and surgical techniques that are not necessarily catheter-based.

The systems and methods are particularly well suited for treating dysfunctions in the upper gastrointestinal tract, e.g., in the lower esophageal sphincter and adjacent cardia of the stomach. For this reason, the systems and methods will be described in this context. Still, it should be appreciated that the disclosed systems and methods are applicable for use in treating other dysfunctions elsewhere in the body, which are not necessarily sphincter-related.

I. Overview

Figure 1:
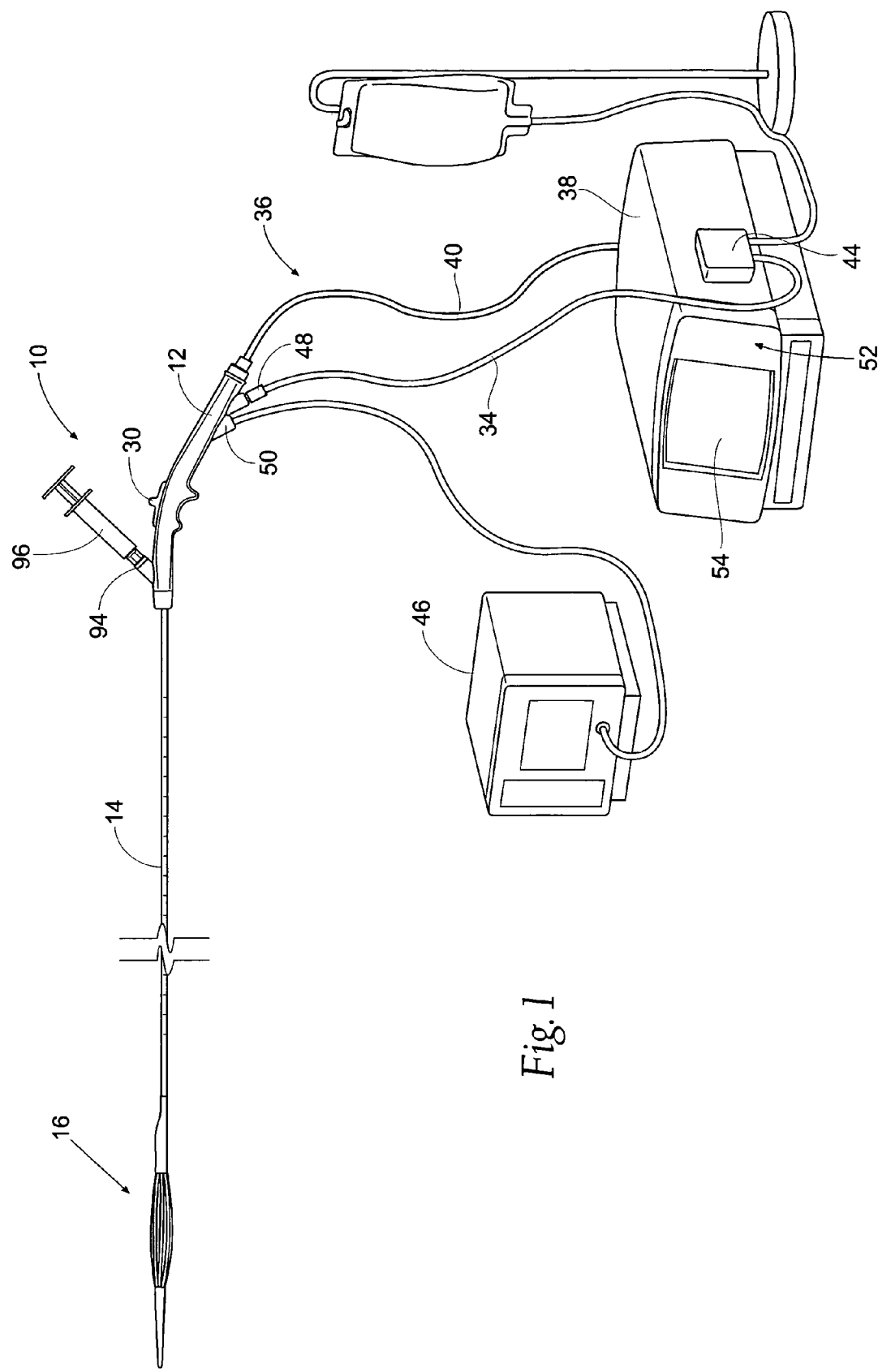
FIG. 1 is a schematic view of a system for treating tissue that includes a treatment device that embodies features of the invention.

A tissue treatment device 10 is shown in FIG. 1. The device 10 includes a handle 12 made, e.g., from molded plastic. The handle 12 carries a flexible catheter tube 14. The catheter tube 14 can be constructed, for example, using standard flexible, medical grade plastic materials, like Pebax™ plastic material, vinyl, nylon, poly(ethylene), ionomer, poly(urethane), poly(amide), and poly(ethylene terephthalate). In the illustrated embodiment (as will be described later), the catheter tube 14 is desirably fabricated as an extruded plastic part.

The handle 12 is sized to be conveniently held by a physician, to introduce the catheter tube 14 into the tissue region targeted for treatment. The catheter tube 14 may be deployed with or without the use of a guide wire. The catheter tube 14 carries on its distal end an operative element 16. The operative element 16 can take different forms and can be used for either therapeutic purposes, or diagnostic purposes, or both. The operative element 16 can support, for example, a device for imaging body tissue, such as an endoscope, or an ultrasound transducer. The operative element 16 can also support a device to deliver a drug or therapeutic material to body tissue. The operative element 16 can also support a device for sensing a physiological characteristic in tissue, such as electrical activity, or for transmitting energy to stimulate tissue or to form lesions in tissue.

In the illustrated embodiment, one function that the operative element 16 performs is to ablate tissue in a selective fashion in a targeted tissue region.

II. The Operative Element

Dedicated Irrigation Lumen

Figure 2A:
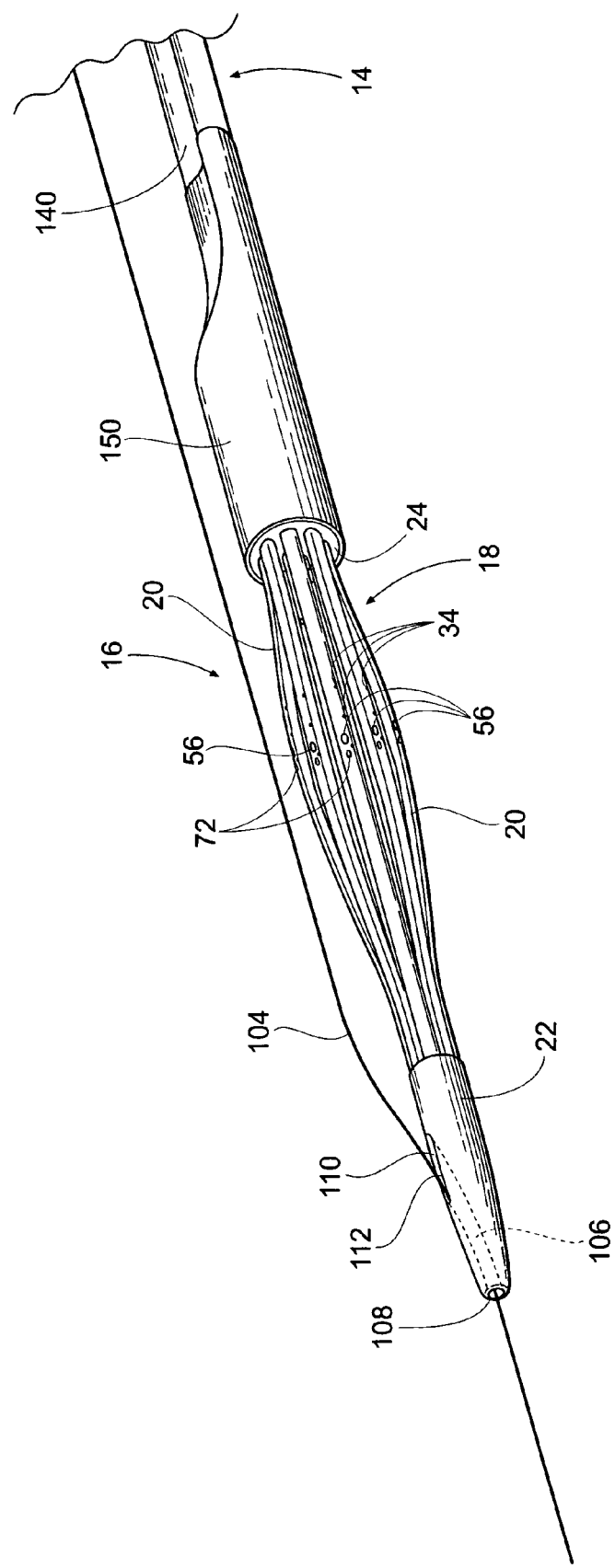
FIG. 2A is a perspective view of the operative element carried at the distal end of the treatment device shown in FIG. 1, the operative element including a basket structure that is shown in a collapsed condition for deployment to a targeted tissue region.
Figure 2B:
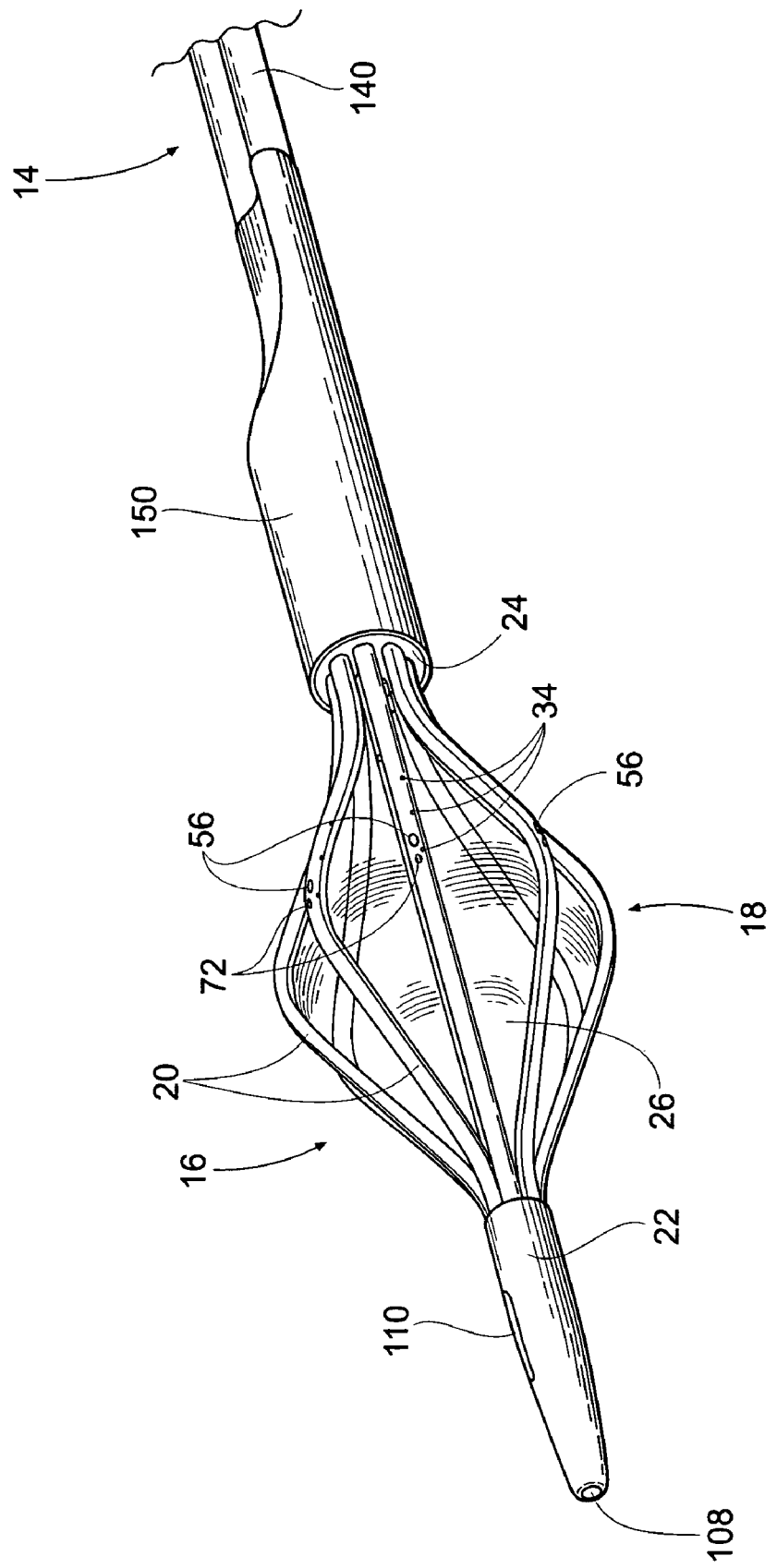
FIG. 2B is a perspective view of the operative element shown in FIG. 2A, the basket structure being shown in an expanded condition after deployment to a targeted tissue region.
Figure 2C:
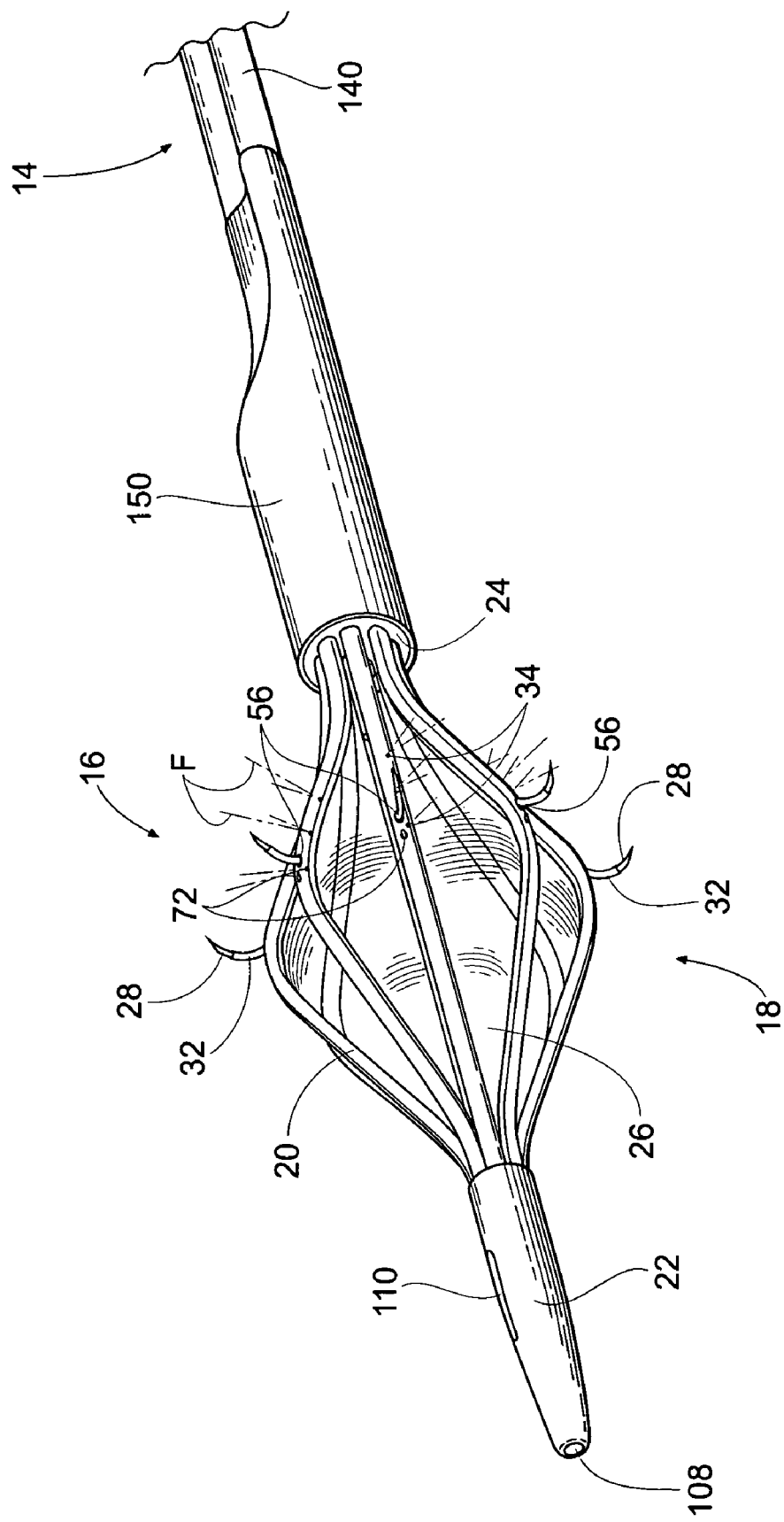
FIG. 2C is a perspective view of the operative element shown in FIG. 2B, after extension of electrode elements carried by the basket structure for deployment into tissue in the targeted tissue region.

In the embodiment shown in FIGS. 2A to 2C, the operative element 16 comprises a three-dimensional basket 18. The basket 18 includes one or more arms 20, and typically includes from four to eight arms 20, which are assembled together between a distal tip 22 and a proximal base element 24. In FIGS. 2A to 2C, eight basket arms 20 are shown, which are arranged to be equally circumferentially spaced apart. Different circumferential spacing patterns could, of course, be used.

In the embodiment shown in FIGS. 2A to 2C, an expandable structure 26 comprising, e.g., a balloon, is located within the basket 18. The expandable balloon structure 26 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material. Non-compliant materials offer the advantages of a predictable size and pressure feedback when inflated in contact with tissue. Compliant materials offer the advantages of variable sizes and shape conformance to adjacent tissue geometries.

The balloon structure 26 presents a normally, generally collapsed condition, as FIG. 2A shows. In this condition, the basket 18 is also normally collapsed about the balloon structure 26, presenting a low profile for deployment into the targeted tissue region.

Expansion of the balloon structure 26 urges the arms 20 of the basket 18 to open and expand (as FIG. 2B shows). The force exerted by the balloon structure 26 upon the basket arms 20, when expanded, is sufficient to exert an opening force upon the tissue surrounding the basket 18. When deployed in a sphincter region, the opening force serves to dilate the sphincter region.

As further shown in FIGS. 2A to 2C, each basket arm 20 carries an electrode element 28. Each electrode element 28 is carried within its respective basket arm 20 for sliding movement. More particularly, each electrode element 28 can be made to slide from a retracted position, withdrawn in the basket arm 20 (as shown in FIGS. 2A and 2B), and an extended position, extending outward from the basket arm 20 through an opening 56 in the basket arm 20 (as shown in FIG. 2C). An electrode control lever 30 on the handle 12 (see FIG. 1) allows the physician to remotely control the position of the electrode elements 28.

When in its extended position, the electrode element 28 penetrates tissue contacted by the basket arms 20. As FIG. 2C shows, the electrode elements 28 are desirably moved to their extended positions when the balloon structure 26 (thus the surrounding basket 18) is expanded against surrounding tissue. When moved to their extended positions, the electrodes 28 penetrate tissue contacted by the expanded basket arms 20.

When extended into tissue, the application of energy through electrode elements 28 serves to heat tissue below the mucosal surface of the tissue that the basket arms 20 contact. The tissue heating creates one or more sub-surface lesions, or a prescribed pattern of sub-surface lesions, below the mucosal surface of the tissue.

In a desired arrangement, the delivered energy comprises radio frequency energy, e.g., energy having a frequency in the range of about 400 kHz to about 10 mHz. A return path is established, e.g., by an external patch electrode, also called an indifferent electrode. In this arrangement, the application of radio frequency energy serves to ohmically heat tissue in the vicinity of the electrode elements 28, to thermally injure the tissue and form the localized sub-surface lesions. Of course, tissue heating can be accomplished by other means, e.g., by coherent or incoherent light; heated or cooled fluid; resistive heating; microwave; ultrasound; a tissue heating fluid; or cryogenic fluid.

In this arrangement (see FIG. 2C), the exterior surface of each electrode element 28 may carry an electrical insulating material 32, except at its distal region, where the radio frequency energy is applied to tissue. The presence of the insulating material 32 serves to preserve and protect the mucosal tissue surface from exposure to the radio frequency energy, and, thus, from thermal damage. In addition, as will be described in greater detail later, an irrigation fluid is preferably discharged through an opening or series of openings 34 (see FIG. 7B) formed in each basket arm 28 in the vicinity of each electrode element 28. The irrigation fluid can comprise, e.g., saline or sterile water. The irrigation fluid cools surface tissue while energy is being applied by the electrode elements 28 to ohmically heat muscle or tissue beneath the surface, to thereby protect the surface tissue from thermal damage.

For the purpose of illustration, the targeted tissue region can comprise, for example, the lower esophageal sphincter, or cardia of the stomach, or both. In this arrangement, the natural healing of subsurface lesions or pattern of subsurface lesions created by the applied energy leads to a physical tightening of the sphincter and/or adjoining cardia and/or a reduction in the compliance of these tissues. The subsurface lesions can also result in the interruption of aberrant electrical pathways that may cause spontaneous sphincter relaxation. In any event, the treatment can restore normal closure function to the sphincter.

In this arrangement (as FIG. 1 shows), the treatment device 10 desirably operates as part of a system 36. The system 36 includes a generator 38 to supply the treatment energy to the operative element 16. In the illustrated embodiment, the generator 38 supplies radio frequency energy to the electrodes 28.

Figure 3A:
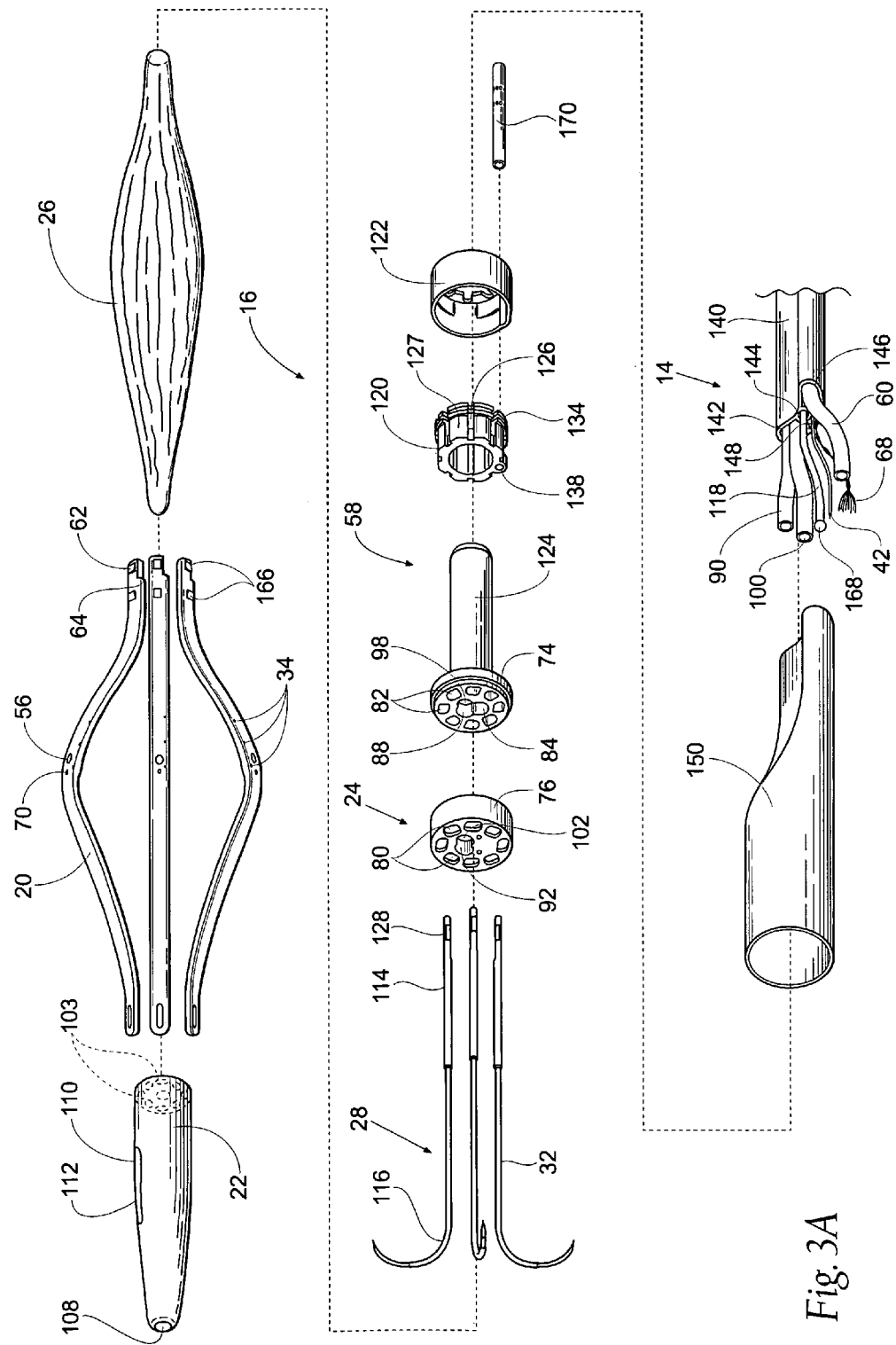
FIG. 3A is an exploded perspective view of the components of the operative element shown in FIGS. 2A to 2C, the operative element providing for cooling of surface tissue by conducting irrigation fluid through dedicated irrigation fluid lumens in the arms of the expandable basket structure, which are separate from the lumens through which the electrode elements are deployed.

A cable 40 extending from the handle 12 is electrically coupled at its distal end to the operative element 16 by electrode supply wires. As FIG. 3A shows, the electrode supply wires 42 extend through the catheter tube 14 and are, at their distal ends, electrically coupled to the electrode elements 28 (see FIG. 3D). This will be described in greater detail later. The proximal end of the cable 40 is electrically coupled to the generator 38, to convey the generated energy to the electrode elements 28 through the supply wires 42.

The system 36 can also include certain auxiliary processing equipment. In the illustrated embodiment, the processing equipment comprises an external fluid delivery or irrigation apparatus 44. In the illustrated embodiment, the fluid delivery apparatus 44 comprises an integrated, self priming peristaltic pump rotor that is carried on a side panel of the generator 38. Other types of non-invasive pumping mechanisms can be used, e.g., a syringe pump, a shuttle pump, or a diaphragm pump.

A luer fitting 48 on the handle 12 couples to tubing 34 to connect the treatment device 10 to the fluid delivery apparatus 44, to convey irrigation fluid for discharge through the irrigation openings 34 (see FIG. 7B) by or near the electrodes 28. This provides localized cooling of surface tissue, as previously described, and as will also be described later in greater detail.

In this arrangement, the processing equipment desirably includes an aspiration source 46. Another luer fitting 50 on the handle 12 couples tubing to connect the treatment device 10 to the aspiration source 46. The aspiration source 46 draws irrigation fluid discharged by or near the electrodes 28 away from the tissue region. The aspiration source 46 can comprise, for example, the vacuum source typically present in a physician's suite.

The system 36 also desirably includes a controller 52. The controller 52 is linked to the generator 38 and the fluid delivery apparatus 44. The controller 52, which preferably includes an onboard central processing unit, governs the power levels, cycles, and duration that the radio frequency energy is distributed to the electrodes 28, to achieve and maintain temperature levels appropriate to achieve the desired treatment objectives. In tandem, the controller 52 also desirably governs the delivery of irrigation fluid.

The controller 52 desirably includes an input/output (I/O) device 54. The I/O device 54, which can employ a graphical user interface, allows the physician to input control and processing variables, to enable the controller to generate appropriate command signals.

A. The Basket Assembly

The various components of the tissue treatment device 10 and operative element 16, as just generally described, can differ in construction and assemblage.

1. The Basket Arms

In one preferred embodiment (see FIG. 3A), each basket arm 20 comprises an extruded body made, e.g. from molded plastic (e.g., Peek™), stainless steel, or nickel titanium alloy. The cross sectional shape of the basket arm 20 can vary, possessing, e.g., a circular, elliptical, square, or rectilinear shape. In the illustrated embodiment (see FIG. 5), each basket arm 20 possesses a generally rectilinear shape to prevent the electrode element 28 carried within the basket arm 20 (which possesses a generally oval cross section) from twisting.

In the illustrated embodiment (see FIG. 5), each extruded basket arm 20 comprises two co-extruded interior lumens or passages, designated L1 and L2. The co-extruded passages L1 and L2 serve different functions.

More particularly, the first co-extruded passage L1 is sized and configured to carry one electrode element 28. The distal, tissue piercing region of the electrode element 28 is aligned within the passage L1 to pass through an opening 56 in the extruded basket arm 20, as shown in FIG. 2C. An electrode advancer assembly 58 (see, e.g., FIGS. 3D and 4) is coupled to the proximal regions of the electrode elements 28 to urge the electrode elements 28 in tandem, fore and aft, through passages L1 of the basket arms 20, in response to operation of the electrode control lever 30 on the handle 12. Further details of the electrode advancer assembly 58 will be described later in greater detail.

The second co-extruded passage L2 extends along one side the first passage L1. The second passage L2 is sized and configured to carry irrigation fluid delivered from the fluid delivery device 44 through a source irrigation tube 60, which passes through the catheter tube (see FIG. 3A). As FIG. 7B best shows, the openings 34 formed in the extruded arm along passage L2 discharge the irrigation fluid in the vicinity of the opening 56 through which the electrode element 28 carried by the arm 20 projects.

Figure 5:
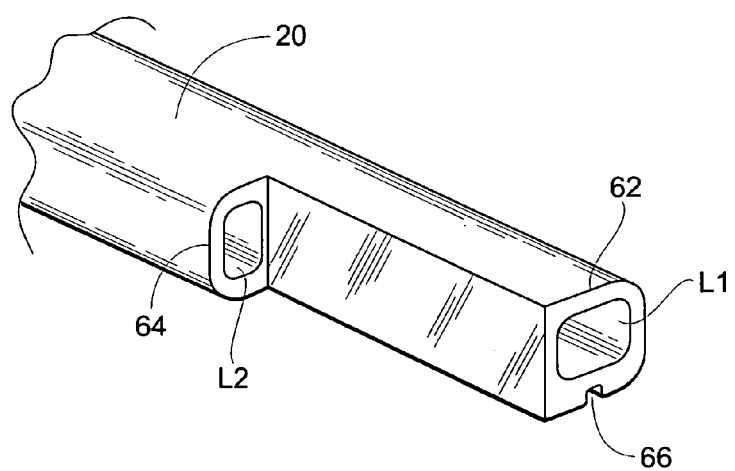
FIG. 5 is an enlarged perspective view of the proximal end of a basket arm of the expandable basket structure shown in FIGS. 3A to 3E and 4, showing the passage for conducting irrigation fluid through the arm.

In the illustrated embodiment, each basket arm 20 is desirably extruded to present a prescribed configuration at its proximal end, which is shown in FIG. 5. In this configuration, the proximal end 62 of the electrode element passage L1 projects beyond the proximal end 64 of the irrigation fluid passage L2. As will be described in greater detail later, this stepped proximal configuration of the basket arms 20 enables the channeling of irrigation fluid through the basket arms 20 from the single irrigation source tube 60 (as FIG. 3A shows), while otherwise isolating all the electrode 28 within the basket arms 20 from contact with the irrigation fluid.

Figure 7A:
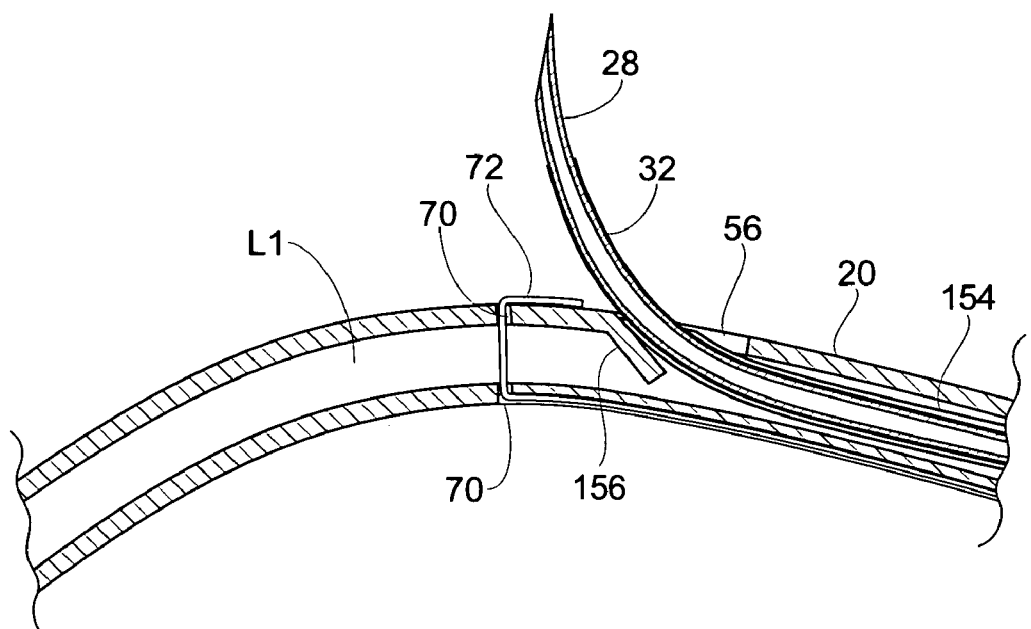
FIG. 7A is an interior side section view of a portion of the basket arm of the expandable basket structure shown in FIGS. 6A and 6B, showing advancement of the electrode element through an opening in the basket arm and the coupling of an associated temperature sensor to the basket arm.
Figure 7B:
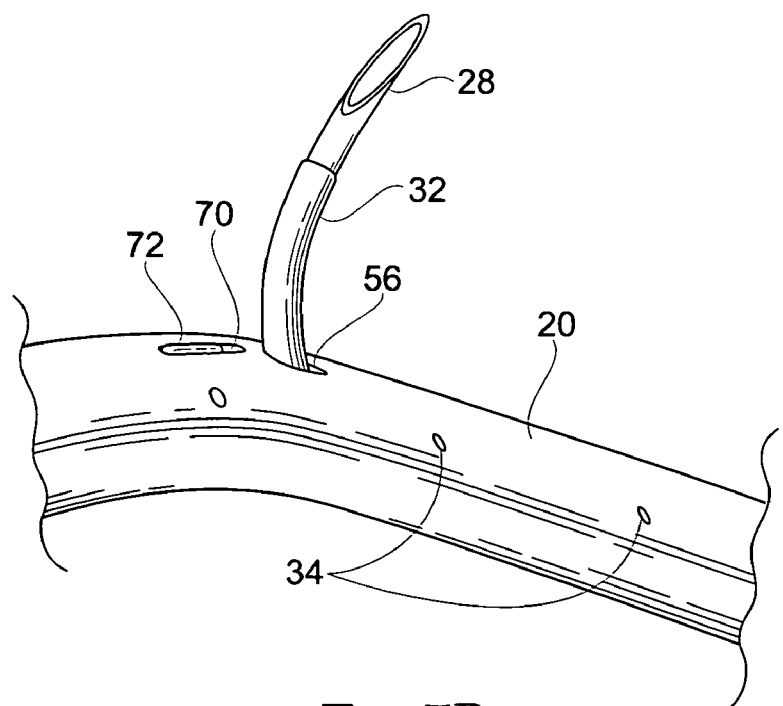
FIG. 7B is an exterior perspective view of the portion of the basket arm shown in FIG. 7A.

As FIG. 5 further shows, an exterior groove 66 is formed, e.g., during extrusion or in an auxiliary machining process, on the outside of each basket arm 20 along the inside surface of the first passage L1 (i.e., the surface of the basket arm that faces the interior of the basket). The groove 66 is sized and configured to accommodate passage of an insulated thermocouple wire, as FIG. 7A shows. A bundle 68 of paired insulated thermocouple wires (see FIG. 3A), desirably equal in number to the number of electrode elements 28, extends through the catheter tube 14. The bundle 68 is separated out into individual paired wires and channeled within the grooves 66 along the basket arms 20, as will be described later.

As FIG. 7A shows, each groove 66 terminates at an aligned pair of through holes 70 in the basket arm 20, which are formed near and distal to the electrode element opening 56. The paired thermocouple wires are joined by soldering or welding to form a temperature sensing junction 72. The junction 72 is passed through the holes 70, from the interior side of basket arm 20 to the exterior side. The junction 72 is then bent or crimped over against the exterior side of the basket arm 20, in the vicinity of the electrode element 26 (see FIG. 7B also).

In use, the crimped-over junction 72 serves as a temperature sensor, which rests against surface tissue when the basket structure 18 is deployed for use. Desirably (as FIG. 7B best shows), the temperature sensor 72 is generally aligned with the electrode element 28 and cooling fluid openings 34, so that sub-surface lesion creation, surface temperature sensing, and cooling occur generally in the same localized tissue region. The temperature conditions sensed near each electrode element 28 are desirably conveyed by the thermocouple wire bundle 68 to the controller 52 for display to the operator and for controlling the application of the radio frequency energy and the discharge of irrigation fluid. In this arrangement, the controller 52 receives real time processing feedback information from the temperature sensors 72. The graphical user interface (GUI) 54 desirably graphically presents processing information to the physician for viewing or analysis.

2. The Basket Base

As FIG. 2A shows, the proximal ends 62 and 64 of the extruded basket arms 20 are collectively joined to the catheter tube 14 by the base element 24. The base element 24 desirably comprises a molded or machined plastic part, comprising, e.g., polycarbonate, or Ultem™ plastic material, or Peek™ plastic material. In the embodiment illustrated in FIG. 3A, the base element 24 is shown to comprise a two part assembly of a base mount 74 joined to a base manifold 76, e.g., by an adhesive bond or suitable mechanical interlock. When the base mount 74 is joined to the base manifold 76 (see FIG. 4), an interior manifold chamber 78 is formed in the base element 24. It is through this manifold chamber 78 that irrigation fluid from the single irrigation tube 60 is channeled through the passages L2 of the multiple basket arms 20.

Figure 4:
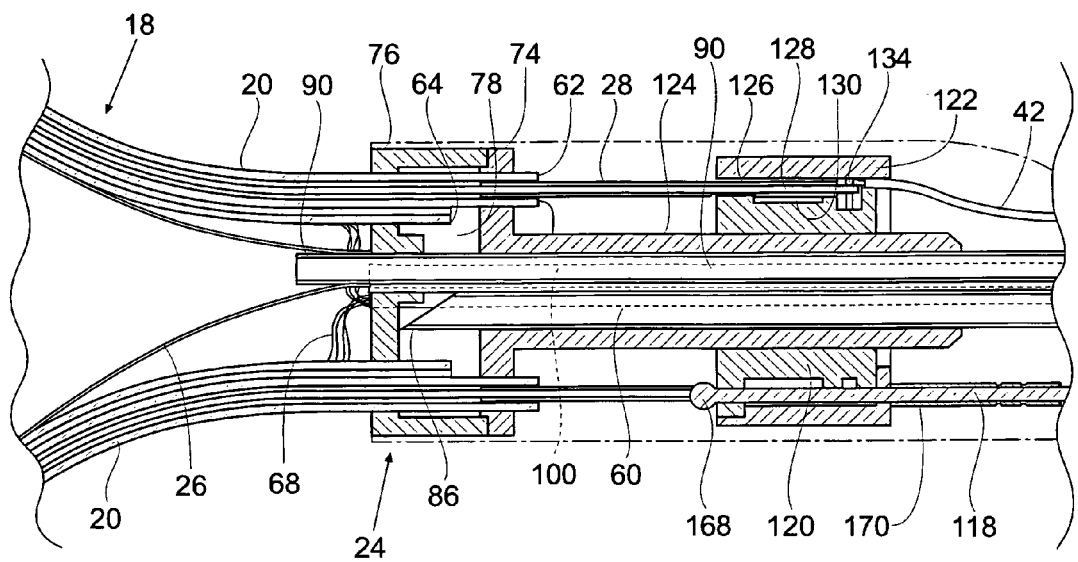
FIG. 4 is a side section view of the assemblage of the electrode advancer assembly and related electrical and fluid conveyance components to the expandable basket structure, as shown in FIG. 3E.

The base manifold 76 includes an array of pre-formed circumferential openings 80 (see, e.g., FIG. 3A), which are sized and configured to receive and engage the proximal ends 62 and 64 of both passages L1 and L2 of the basket arms 28 (see FIG. 4). The engagement preferably comprises a secure, mechanical, friction fit. The friction fit can be further enhanced, e.g., by use of an adhesive bond or suitable mechanical interlock (e.g., one or more barbs 166, as shown in FIG. 3A).

The base mount 74 also includes an array of circumferential openings 82 that are sized and configured to receive and engage only the proximal ends 62 of the basket arms 20 (see FIG. 4). The stepped configuration of the proximal ends 62 and 64 of the basket arms 20, previously described and shown in FIG. 5, allows the elongated extension of the proximal ends 62 (i.e., the passages L1) across the manifold chamber 78 and through the mount openings 82. The shorter extensions of the proximal ends 64 (i.e., the passages L2) terminate within the manifold chamber 78 short of the base mount 74. The passages L2 therefore commonly communicate with the manifold chamber 78, while the passages L1 do not.

Due to this arrangement (see FIG. 4) the electrode element passages L1, when coupled to the base element 24, extend across the manifold chamber 78 and through the base mount 74, without fluid communication with the manifold chamber 78. At the same time, the shorter irrigation fluid passages L2, when coupled to the base element 24, lay in direct fluid communication with the manifold chamber 78. In this way, the electrode elements 28 are kept entirely isolated from contact with the irrigation fluid within the manifold chamber 78, even while all basket arms 20 serve to deliver irrigation fluid.

The base mount 74 further includes a first, more central opening 84. This opening 84 is sized and configured to allow fluid-tight passage of the single source irrigation tube 60 (see FIGS. 3A and 4). The source irrigation tube 60 terminates within the manifold chamber 78, to discharge the irrigation fluid into the manifold chamber 78. The irrigation fluid is distributed by the manifold chamber 78 to the passages L2 of all the basket arms 20. As shown in FIG. 4, the source irrigation tube 60 desirably includes a tapered outlet region 86, which discharges irrigation fluid toward the center region of the manifold chamber 78, for more uniform distribution to the passages L2 of the basket arms 20.

The base mount 74 also includes a second, more central opening 88 (see FIG. 3A). This opening 88 is sized and configured to allow fluid-tight passage of an inflation tube 90 for the balloon structure 26, as FIG. 4 shows. The base manifold 76 likewise includes a more central opening 92 (see FIG. 3A) that registers with the second, more central opening 88 of the base mount 74. As FIG. 4 shows, the single, more central opening 92 of the base manifold 76 is sized and configured to accommodate fluid-tight extension of the inflation tube 90 through the manifold chamber 78, distally beyond the base element 24. The terminal end of the inflation tube 90 is joined to the balloon structure 26. The inflation tube 90 carries fluid under pressure into the balloon structure 26, causing its expansion. As FIG. 1 shows, a luer fitting 94 can couple a syringe 96 to the handle 12, to supply the inflation fluid.

The base mount 74 also includes a third, more central opening 98 (see FIG. 3A). This opening 98 is sized and configured to allow fluid-tight passage of an aspiration tube 100, as FIG. 4 shows. The base manifold 76 likewise includes a another, more central opening 102 (see FIG. 3A) that registers with the third, more central opening 98 of the base mount 74. As FIG. 4 shows, the other, more central opening 102 of the base manifold 76 is sized and configured to accommodate fluid-tight extension of the aspiration tube 100 through the manifold chamber 78. The aspiration tube 100 terminates generally flush with the distal face of the base element 24. The terminal end of the aspiration tube 100 communicates with the interior of the basket structure 18, outside the balloon structure 26. Coupled to the aspiration source 46 (see FIG. 1), the aspiration tube 100 draws irrigation fluid discharged through the openings 34 on the basket arms 20 to promote localized cooling, away from the operative element 16.

3. The Basket Tip

Figure 3B:
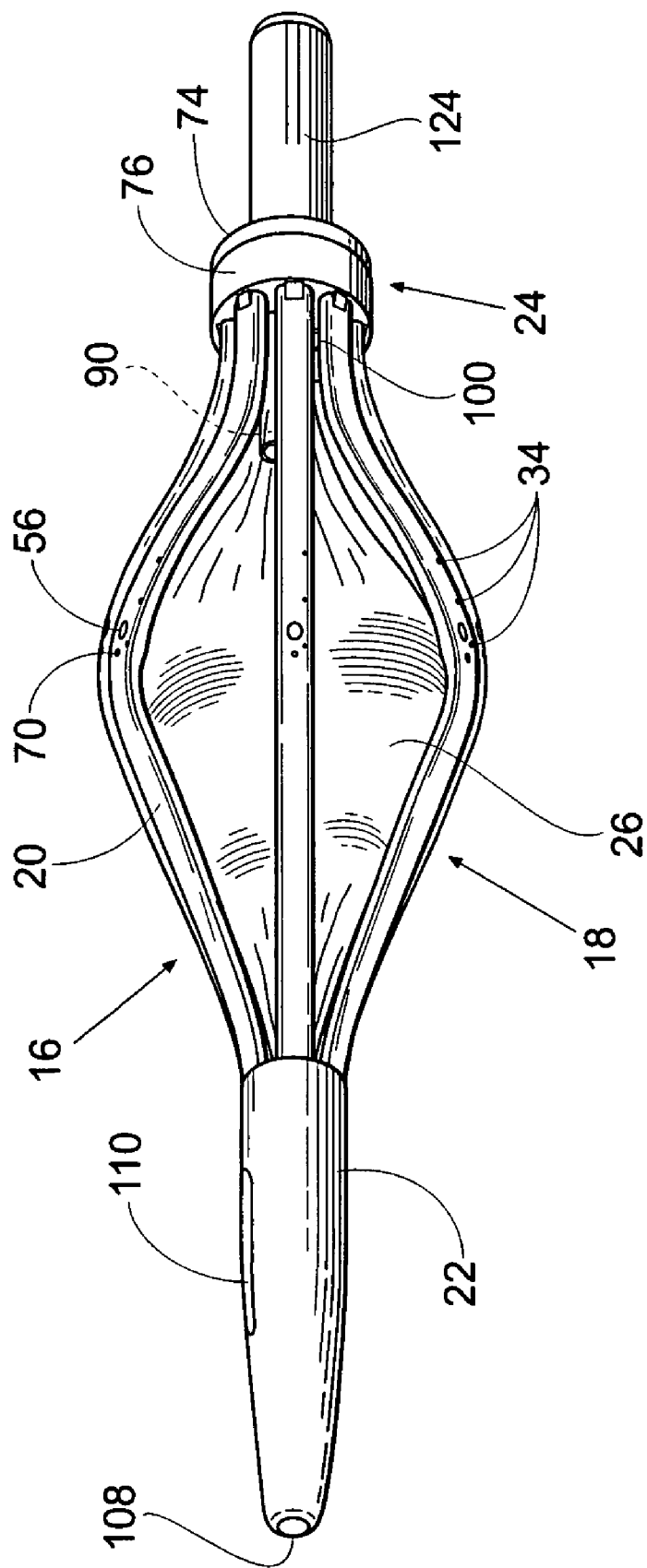
FIG. 3B is a partially assembled view of the operative element shown in FIG. 3A, showing the assemblage of the expandable basket structure.
Figure 3D:
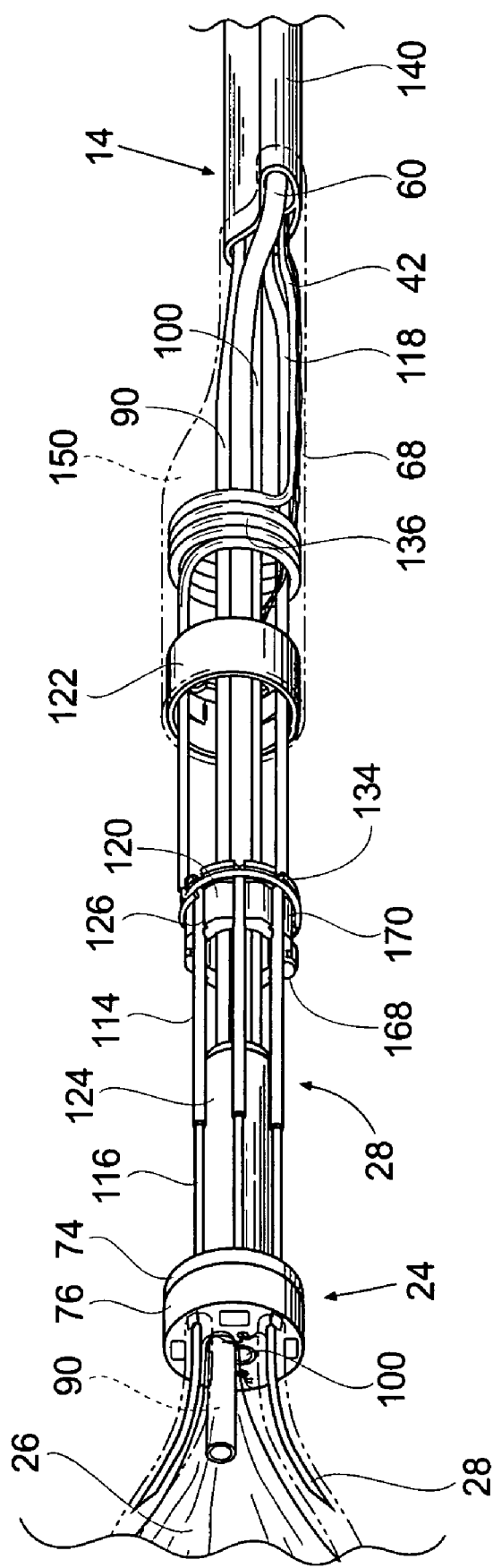
FIG. 3D is a further partially assembled view of the operative element shown in FIG. 3C, showing more of the assemblage of the electrode advancer assembly and related electrical and fluid conveyance components to the expandable basket structure shown in FIG. 3C.
Figure 3E:
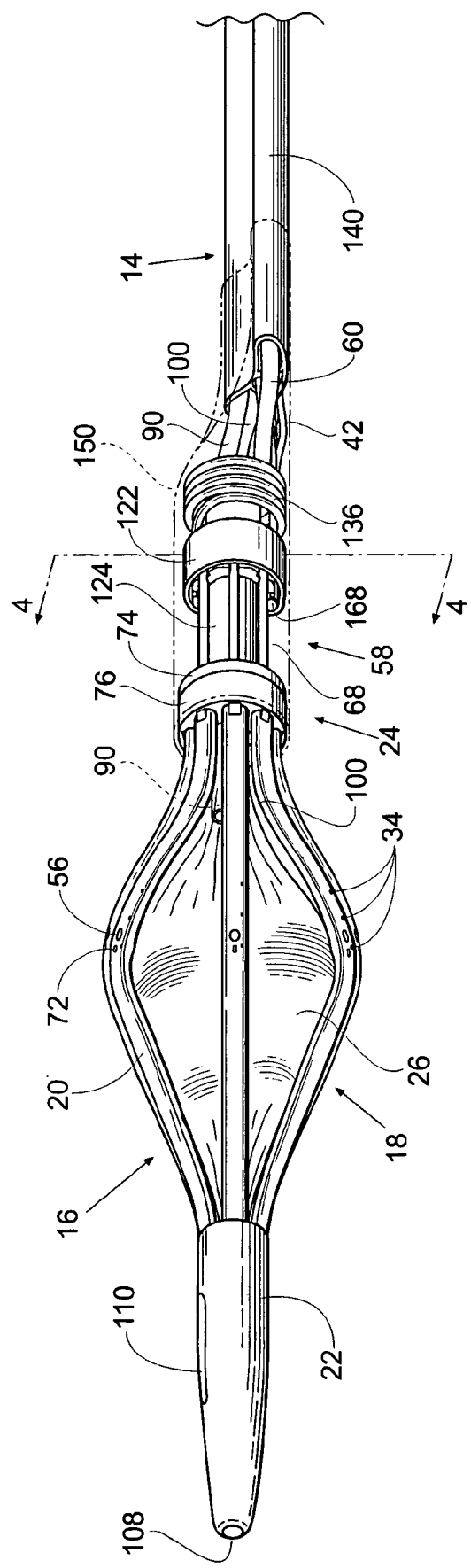
FIG. 3E is a further partially assembled view of the operative element shown in FIG. 3D, showing essentially the complete assemblage of the electrode advancer assembly and related electrical and fluid conveyance components to the expandable basket structure shown in FIG. 3D.

As FIG. 3D also best shows, the distal ends of the extruded basket arms 20 are collectively joined by the distal tip 22. Arms 20 are sized and configured to be received by openings 103 in distal tip 22 to secure the basket 18 to the distal tip 22 (see also FIG. 45). The distal tip 22 may be conventional, formed, e.g., from semi-rigid, medical grade plastic (e.g., Pebax™ plastic material, polyurethane, silicone, Santoprene™ plastic material, Kraton™ plastic material, or other flexible materials) by conventional molding techniques.

As FIG. 2A shows, the distal tip 22 can be adapted to accommodate a guide wire 104. The purpose of the guide wire 104 is to aid insertion and guidance of the operative element 16 into the targeted tissue region. In the illustrated embodiment, the guide wire 104 is threaded through an interior lumen 106, which extends within the distal tip 22. The interior lumen 106 extends between a side entrance 110 and a distal opening 108 in the tip 22. A slot 112 in the side entrance 110 aids in threading a guide wire 104 through the tip 22, as illustrated in FIG. 2A.

B. The Electrode Elements

The electrode elements 28 can be formed from various energy transmitting materials. For deployment in the esophagus or cardia of the stomach, the electrode elements 28 are formed, e.g., from nickel titanium. The electrode elements 28 can also be formed from stainless steel, e.g., 304 stainless steel, or, as will be described later, a combination of nickel titanium and stainless steel. The electrode elements 28 have sufficient distal sharpness and strength to penetrate a desired depth into the smooth muscle of the esophageal or cardia wall. The desired depth can range from about 4 mm to about 5 mm.

The electrode elements 28 can be formed in various sizes and shapes. The electrode elements 28 can possess a circular cross sectional shape. However, the electrode elements 28 preferably possess a cross section that provides increased resistance to twisting or bending as the electrodes penetrate tissue. For example, the electrode elements 28 can possess a rectangular cross section. Alternatively, the electrode elements 28 can possess an elliptical cross section. Other cross sections, e.g., conical or pyramidal, can also be used to resist twisting.

To further facilitate penetration and anchoring in the targeted tissue region, each electrode element 28 is preferably biased with a bend (as FIG. 3A shows). Movement of the electrode element 28 through the passage L1 overcomes the bias and straightens the electrode 28. Movement through the opening 56 in the arm 20 frees the electrode element 28 to assume the biased shape (as FIG. 2C shows).

In the illustrated embodiment (as FIG. 3A shows), each electrode element 28 is normally biased with an antegrade bend (i.e., bending toward the basket base element 24). Alternatively, each electrode element 28 can be normally biased toward an opposite retrograde bend (i.e., bending toward the basket distal tip 22). Whatever the direction, the bend provides a secure anchorage in tissue.

In this arrangement (see FIG. 3A), the electrode element 28 may comprise a hybrid of materials comprising stainless steel for the proximal portion 114 and nickel titanium alloy for the distal portion 116. The nickel titanium alloy performs best in the curved distal portion 116 of the electrode element 28, due to its super-elastic properties. The use of stainless steel in the proximal portion 114 can reduce cost, by minimizing the amount of nickel titanium alloy required.

The different materials may be joined, e.g., by crimping, roll flattening, platen flattening, swaging, soldering, welding, or adhesive bonding, which provide electrical continuity between or among the various materials.

As previously described, the electrical insulating material 32 (see FIG. 3A) may be coated about the distal end of each electrode element 28, a distance below the distal tip. The material 32 can be coated on the proximal portion 114, or the distal portion 116, or both, depending upon the relative lengths of each portion 114 and 116. For deployment in the esophagus or cardia, the length of the insulating material 32 ranges from about 10 to about 40 mm. The insulating material can comprise, e.g., a Polyethylene Terephthalate (PET) material, or a polyimide or polyamide material. For deployment in the esophagus or cardia, each electrode element 28 preferably presents an exposed, non-insulated conductive length of about 8 mm. When the distal end of the electrode element 28, which penetrates the targeted tissue region, transmits radio frequency energy, the material 32 insulates the surface of the tissue region from direct exposure to the radio frequency energy. The material 32 also reduces the incidence of electrical "cross-talk" among the electrode elements 28.

In the illustrated arrangement, the electrode elements 28 are intended for monopolar operation. Each electrode element 28 serves as a transmitter of energy, and an indifferent patch electrode on the patient's skin (not shown) serves as a common return for all electrode elements 28. It should be appreciated, however, the operative element 16 could include bipolar pairs of electrode elements 28, if desired.

C. The Electrode Advancer Assembly

The electrode advancer assembly 58 enables the electrode element 28 carried within the basket arms 20 to be moved simultaneously between the retracted position, withdrawn in the basket arm 20 (as shown in FIG. 2A), and an extended position, extending outward from the basket arm 20 through the opening 56 in the arm 20 (as shown in FIG. 2C).

As FIG. 1 shows, the handle carries a push-pull control lever 30. The push pull lever 30 is coupled by a stylet 118 to the electrode advancer assembly 58. The stylet 118 extends through the catheter tube 14, as FIG. 3A shows.

As FIG. 3A also shows, the electrode advancer assembly 58 includes an electrode advancer hub 120, an electrode advancer sleeve 122, and an electrode advancer stem 124.

As FIG. 3B shows, the proximal ends of the electrode elements 28 (which exit the basket arms 20 through the base mount 74) are collectively coupled to the electrode advancer hub 120. As FIG. 3C shows, the proximal ends of the electrode elements 28 ride within axial channels 126 defining a series of external ribs 127 on the electrode advancer hub 120. A slot 128 formed on the proximal end of each electrode element 28 (see FIG. 3A) fits over a boss 130 formed in each channel 126. This mechanically couples the electrode element 28 to the electrode advancer hub 120, without need of an adhesive or welding.

The electrode advancer sleeve 122 is sized and configured to fit over the electrode advancer hub 120 (see FIGS. 3C and 4). The electrode advancer sleeve 122 captures the proximal ends of the electrode elements 28 resting within the channels 126, thereby completing the attachment of the electrode elements 28 to the hub 120.

During actual assembly, the stylet 118 is back-loaded through the advancer hub 120 and sleeve 122 and into the catheter tube 14. A ball 168 on the distal end of the stylet 118 (see FIG. 3D) abuts against the distal surface of the advancer hub 120. As FIG. 3D also shows, a crimped length of hypotubing 170 is cinched up against the proximal surface of the advancer sleeve 122, thereby securing the advancer hub 120 and advancer sleeve 122 together with a mechanical, adhesive-less joint. The stylet 118 is also joined to the assembled advancer hub 120 and sleeve 122. Advancement of the stylet 118 thereby imparts movement to the electrode advancer hub 120 and sleeve 122 as a unit, also thereby imparting movement to the electrode elements 28 themselves.

The electrode advancer hub 120 and sleeve 122 each desirably comprises a molded or machined plastic part, comprising, e.g., polycarbonate or Ultem™.

The distal end of the electrode advancer stem 124 is coupled to the base mount 74 (see FIG. 3B). The stem 124 desirably comprises a plastic part that is integrally molded or machined with the base mount 74. Of course, the stem 124 can comprise a separate molded or machined plastic part later joined to the base mount 74.

The electrode advancer hub 120 includes an open central passage 132 (see FIG. 3A). The passage 132 is sized and configured to slidably fit about the stem 124 (see FIG. 3C). The hub 120 can thereby ride fore and aft along the stem 124, as FIGS. 6A and 6B show.

Figure 6A:
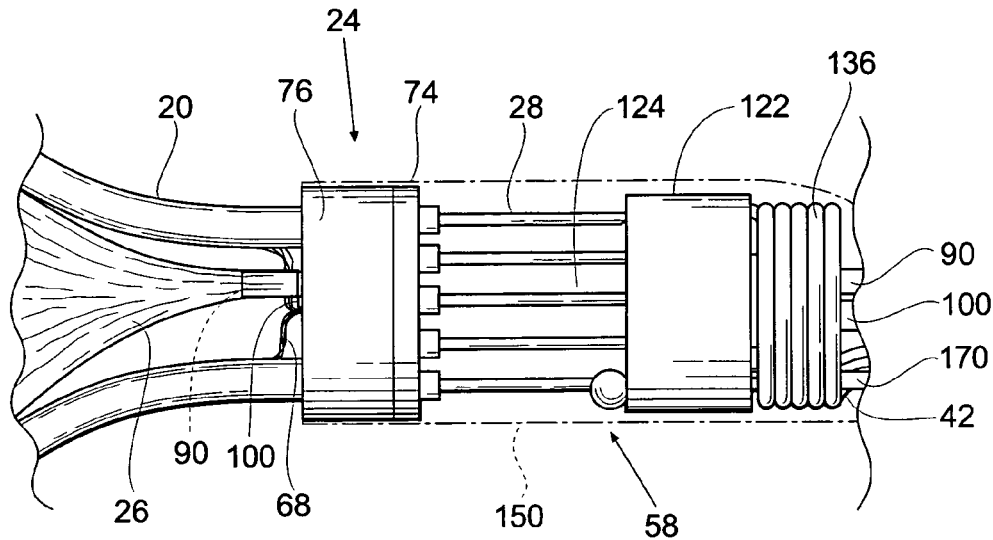
FIGS. 6A and 6B are side views of the assemblage of the electrode advancer assembly and related electrical and fluid conveyance components to the expandable basket structure, as shown in FIG. 3E, showing fore and aft movement of the electrode advancer assembly to extend and withdraw the electrode elements.
Figure 6B:
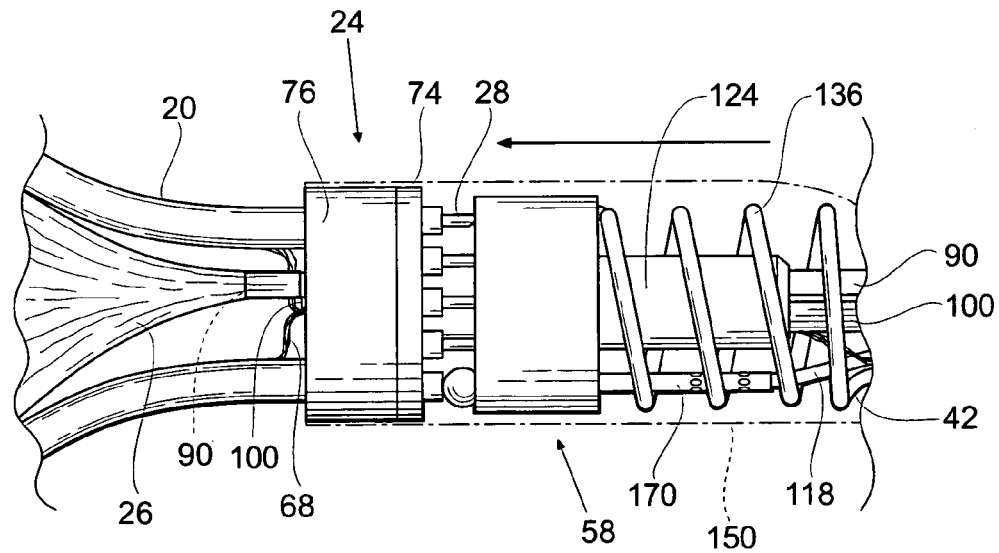

When assembled to the electrode advancer sleeve 122 (as FIGS. 6A and 6B show), movement of the stylet 118 (attached to the sleeve 122) serves to slide the assembly of the hub 120 and sleeve 122 as a unit along the stem 124. The electrode elements 28 carried by the hub 120 are likewise advanced fore and aft through the basket arms 20 between the position shown in FIG. 6A, which results in the extended electrode positions shown in FIG. 2C, and the position shown in FIG. 6B, which results in the retracted electrode positions shown in FIGS. 2A and 2B.

In one arrangement (see FIG. 7A), each electrode element 28 slides within an insert 154 positioned within the first passage L1. The insert 154 guides the electrode element 28 to the electrode opening 56 and protects the extruded basket arm 20 from inadvertent puncture or "poke-through" by the electrode element 28. In assembly, the electrode opening 56 is formed in the arm 20 in a secondary operation after extrusion by a heat gun or the like. As FIG. 7A shows, the heat gun displaces a segment 156 of the arm wall into the passage L1 as the opening 56 is created. This wall segment 156 is deflected into the passage L1, to form an interior ramp appended to the opening 56. Further details of the insert 154 and the ramp segment 156 are described in U.S. patent application Ser. No. 09/955,915, filed Sep. 19, 2001, now U.S. Pat. No. 6,699,243, which is incorporated herein by reference.

In another, more desired arrangement, the interior of the first passage L1 is shaped during extrusion (or by molding, as will be described later) to form a ramp leading to the location of the electrode opening 56.

The distal ends of the electrode supply wires 42 are free of insulating tubing (e.g., made from PET™ plastic material) and are wrapped about an annular channel 134 formed at the proximal end of the electrode advancer hub 120 (see FIG. 4). In the channel 134, the electrode supply wires 42 are electrically coupled to the proximal ends of the electrode elements 28. The electrode advancer sleeve 122, when assembled to the electrode advancer hub 120, covers the annular channel 134 and thereby encloses the supply wires 42.

Between the channel 134 and the terminus of the catheter tube 14, the electrically insulated electrode supply wires 42 are desirably formed into a resilient coil 136. The coil 136 resiliently contracts and expands (see FIGS. 6A and 6B) to accommodate, respectively, aft and fore movement of the electrode advancer hub 120 and sleeve assembly along the electrode advancer stem 124. The thermocouple wire bundle 68 extends from the terminus of the catheter tube 14 (see FIG. 3A) and, as a bundle 68, through a side channel 138 formed in the electrode advancer hub 120 (see FIG. 3B). Adjacent the proximal side of the base manifold 76 (see FIG. 4), the bundle 68 is separated out into individual pairs of thermocouple wires and routed individually through the grooves 66 formed for this purpose along the passage L1 of the basket arms 20, as previously described and shown in FIG. 7A.

D. The Catheter Tube

In the illustrated embodiment (see FIG. 3A), the catheter tube 14 desirably comprises an extruded multiple lumen shaft 140. The co-extruded lumens 142 to 148 in the shaft 140 accommodate passage of the various components that, in use, couple to the operative element 16.

More particularly, one co-extruded lumen 142 accommodates passage of the aspiration tube 100 and the balloon inflation tube 90. A second co-extruded lumen 144 accommodates passage of the electrode advancer stylet 118. A third co-extruded lumen 146 accommodates passage of the irrigation tube 60. A fourth co-extruded lumen 148 accommodates passage of the electrode supply wires 42 and the bundle 68 of thermocouple wires.

In the illustrated embodiment, the extruded shaft 140 includes a scalloped external configuration. This configuration reduces the overall outside diameter of the shaft 140 and allows side-by-side use with an visualization element, as will be described in greater detail later.

The catheter tube 14 also desirably includes a distal shaft component 150. The distal shaft component 150 desirably comprises a molded or machined plastic part, comprising, e.g., polycarbonate, or Pebax™ plastic material, or PET™ plastic material, or Ultem™ plastic material. The distal shaft component 150 is sized and configured at its proximal end to engage the terminus of the extruded catheter shaft 140 in a frictional slide-fit, which can be augmented with the use of adhesive or thermal bonding. The distal shaft component 150 is sized and configured at its distal end to hold and secure the base element 24 of the basket assembly 18 in a frictional slide-fit, which can likewise be augmented with the use of adhesive or thermal bonding. The base element 24 can also include one or multiple annular barbs to augment the joining of the distal shaft component 150. When assembled to the shaft 140 and the base element 24, the distal shaft component 150 encloses the working components of the electrode advancer assembly 58, base element 24, tubes, and wires serving the operative element 16.

III. The Operative Element

Irrigation Balloon

FIGS. 8 to 11 show a second embodiment of an operative element 16'. The operative element 16' shares many features of the first embodiment of the operative element 16 just described. Like reference numbers are therefore assigned like structural elements.

Figure 8:
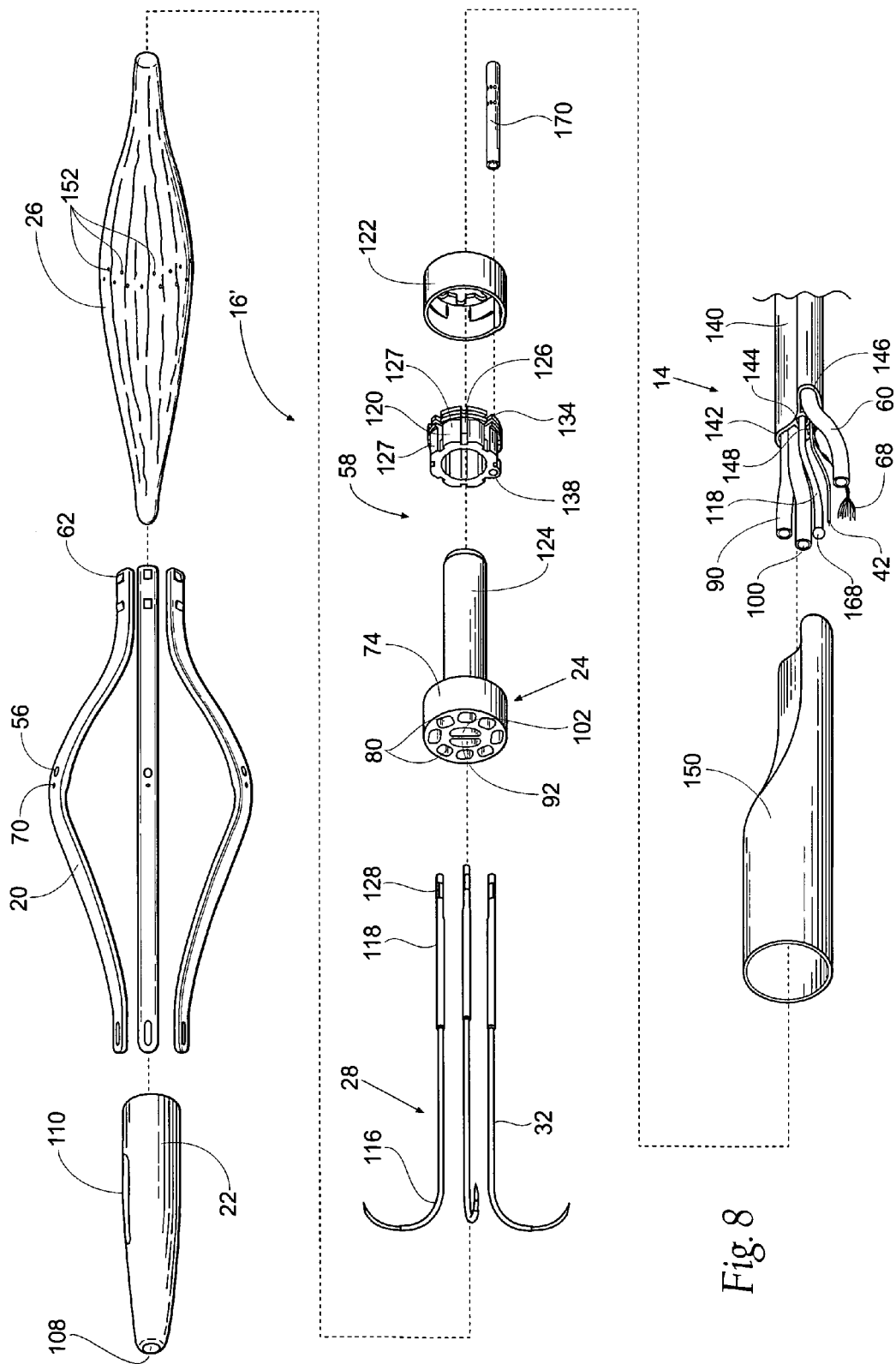
FIG. 8 is an exploded perspective view of the components of another embodiment of an operative element that can be used in association with the treatment device shown in FIG. 1, this operative element providing for cooling of surface tissue by conducting irrigation fluid through an expandable balloon within the basket structure.

Like the embodiment of the operative element 16 shown in FIGS. 2A to 2C, the operative element 16' shown in FIGS. 8 to 11 comprises a three-dimensional basket 18. The basket 18 likewise includes an array of extruded arms 20, which are assembled together between a distal tip 22 and a proximal base element 24. As FIG. 8 shows, the distal tip 22 can include an interior lumen 106 for threading a guide wire, as previously described.

Figure 9:
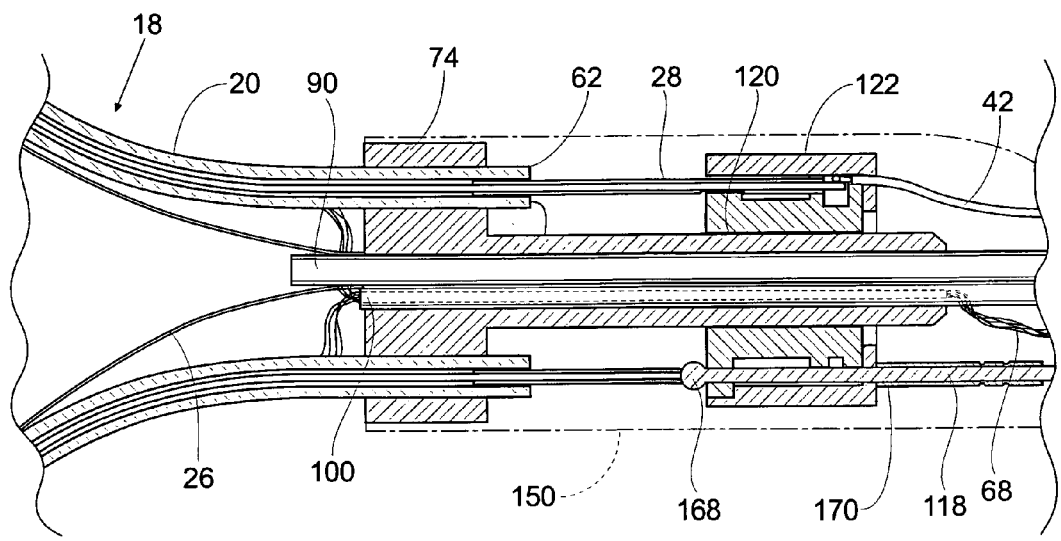
FIG. 9 is a side section view of the embodiment of the operative element shown in FIG. 8, showing the assemblage of assemblage of the electrode advancer assembly and related electrical and fluid conveyance components to the expandable basket structure.
Figure 10:
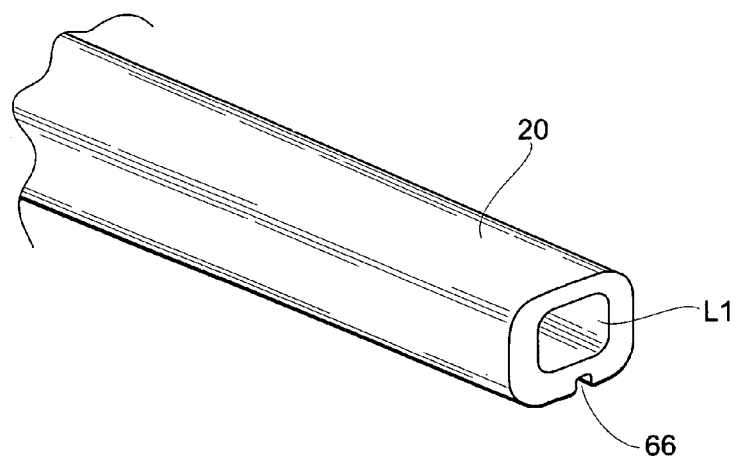
FIG. 10 is an enlarged perspective view of the proximal end of a basket arm of the expandable basket structure shown in FIGS. 8 and 9.
Figure 11:
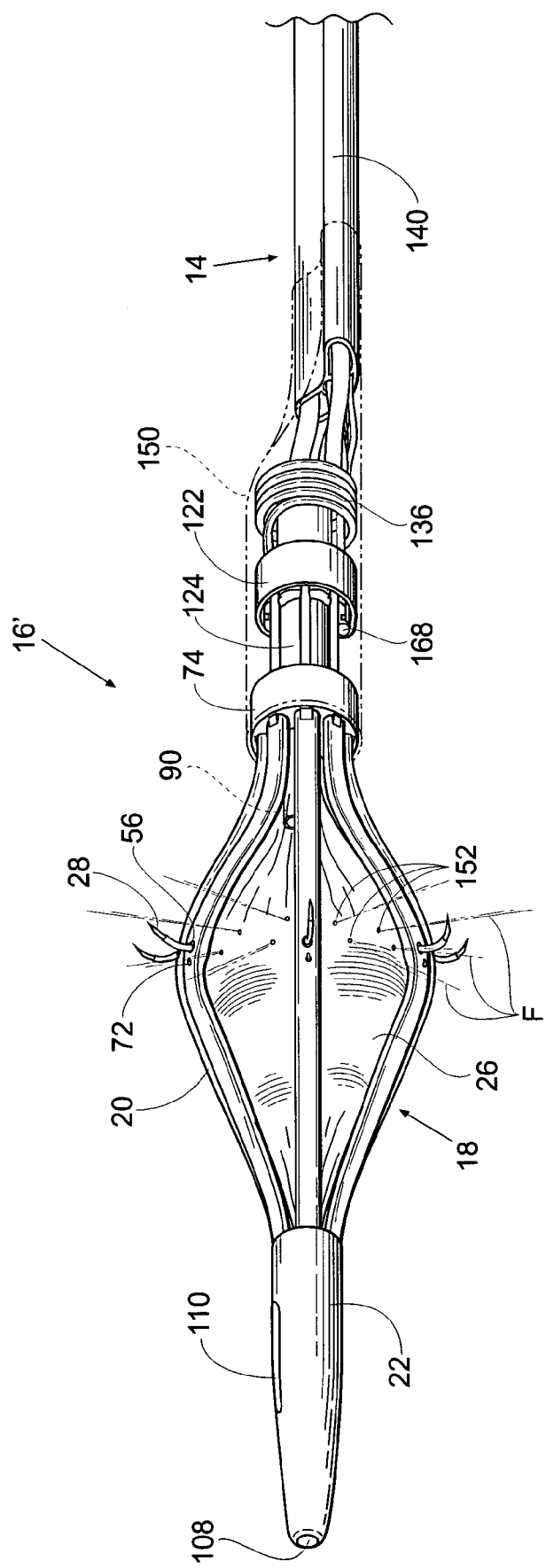
FIG. 11 is a perspective view of the expandable basket structure shown in FIGS. 8 and 9, with the basket structure shown in its expanded condition and irrigation fluid being conveyed through a series of openings formed in the interior balloon structure.

The operative element 16' shown in FIGS. 8 to 11 also includes an expandable balloon structure 26 located within the basket 18. As previously described, the balloon structure 26 expands from a generally collapsed condition (as FIG. 8 shows) and an expanded condition (as FIG. 11 shows).

In the embodiment shown in FIGS. 8 to 11, each basket arm 20 likewise carries an electrode element 28 for sliding movement from a retracted position to an extended position, for piercing tissue, as shown in FIG. 11. When extended into tissue, the application of energy—which desirably is radio frequency energy—through electrode elements 28 serves to ablate tissue below the mucosal surface of the tissue that the basket arms 28 contact. To facilitate penetration and anchoring in the targeted tissue region, each electrode element 28 is preferably biased with a bend (as FIG. 8 shows), as previously discussed.

An electrode advancer assembly 58 couples a stylet 118 operated by a push-pull control lever 30 to enable movement of the electrode elements 28 carried within the basket arms 20. The stylet 118 extends through the catheter tube 14, as FIG. 8 shows. As FIG. 8 also shows, the electrode advancer assembly 58 includes an electrode advancer hub 120, an electrode advancer sleeve 122, and an electrode advancer stem 124, which are constructed and arranged in the same manner previously described. As FIG. 9 shows, the proximal ends of the electrode elements 28 are collectively coupled to the electrode advancer hub 120, as previously described. The electrode advancer sleeve 122 fits over the electrode advancer hub 120 to capture the proximal ends of the electrode elements 28. Coupled to the stylet 118, the assembly of the electrode advancer hub 120 and sleeve 122 rides fore and aft along the stem 124, advancing the electrode elements 28 fore and aft through the basket arms 20. The electrical connections of the electrode supply wires 42 (which pass through the catheter tube 14, as FIG. 8 shows) to the proximal ends of the electrode elements 28 are accomplished in the same manner as previously described. As previously described, the thermocouple wire bundle 68 extends from the terminus of the catheter tube 14 as a bundle 68, through a side channel 138 formed in the electrode advancer hub 120, and is separated out into individual pairs of thermocouple wires and routed individually through the grooves 66 formed for this purpose in the basket arms 20.

Also as previously discussed, each electrode element 28 may comprise a hybrid of materials comprising stainless steel for the proximal portion 114 and nickel titanium alloy for the distal portion 116.

To preserve and protect the mucosal tissue surface from exposure to the radio frequency energy, the exterior surface of each electrode element 28 also desirably carries an electrical insulating material 32, except at its distal region, where the radio frequency energy is applied to tissue.

As before described, an irrigation fluid is preferably discharged in the vicinity of each electrode element 28 to cool surface tissue while energy is being applied by the electrode elements 28. Unlike the embodiment shown in, e.g., FIG. 7B—in which the irrigation fluid is conveyed into a dedicated passage L2 and through openings 34 in the basket arms 20—in the embodiment shown in FIGS. 8 to 11, the irrigation fluid is conveyed through an array of openings 152 formed in the balloon structure 26 itself (see FIG. 11), e.g., by laser drilling, mechanical drilling, or poking with a hot needle. This difference leads to the elimination of a dedicated irrigation tube 60 passed through the catheter tube 14, as well as to the elimination of a manifold element coupled to the irrigation tube 60 on the proximal basket base, as will now be explained.

For a first difference, in the operative element 16', each extruded basket arm 20 comprises only a single interior lumen L1, as FIG. 10 shows. This is because, in this embodiment, no irrigation fluid is transported through the basket arm 20, so there is no need for the second passage L2.

The single passage L1 is sized and configured to carry one electrode element 28, in the same manner as previously described. An electrode advancer assembly 58 (see, e.g., FIGS. 8 and 9) is coupled to the proximal regions of the electrode elements 28 to urge the electrode elements 28 in tandem, fore and aft, through passages L1 of the basket arms 20, in response to operation of the electrode control lever 30 on the handle 12.

As FIG. 10 also shows, an exterior groove 66 is formed on the outside of each basket arm 20. The groove 66 is sized and configured to accommodate passage of an insulated thermocouple wire, in the manner shown in FIGS. 7A and 7B. As FIG. 8 shows, a bundle 68 of insulated thermocouple wires extends through the catheter tube 14, which is separated into individual wires and channeled within the grooves 66 along the basket arms 20. An end 72 of each thermocouple wire is passed through the through holes 70 to serve as a temperature sensor.

Figure 12:
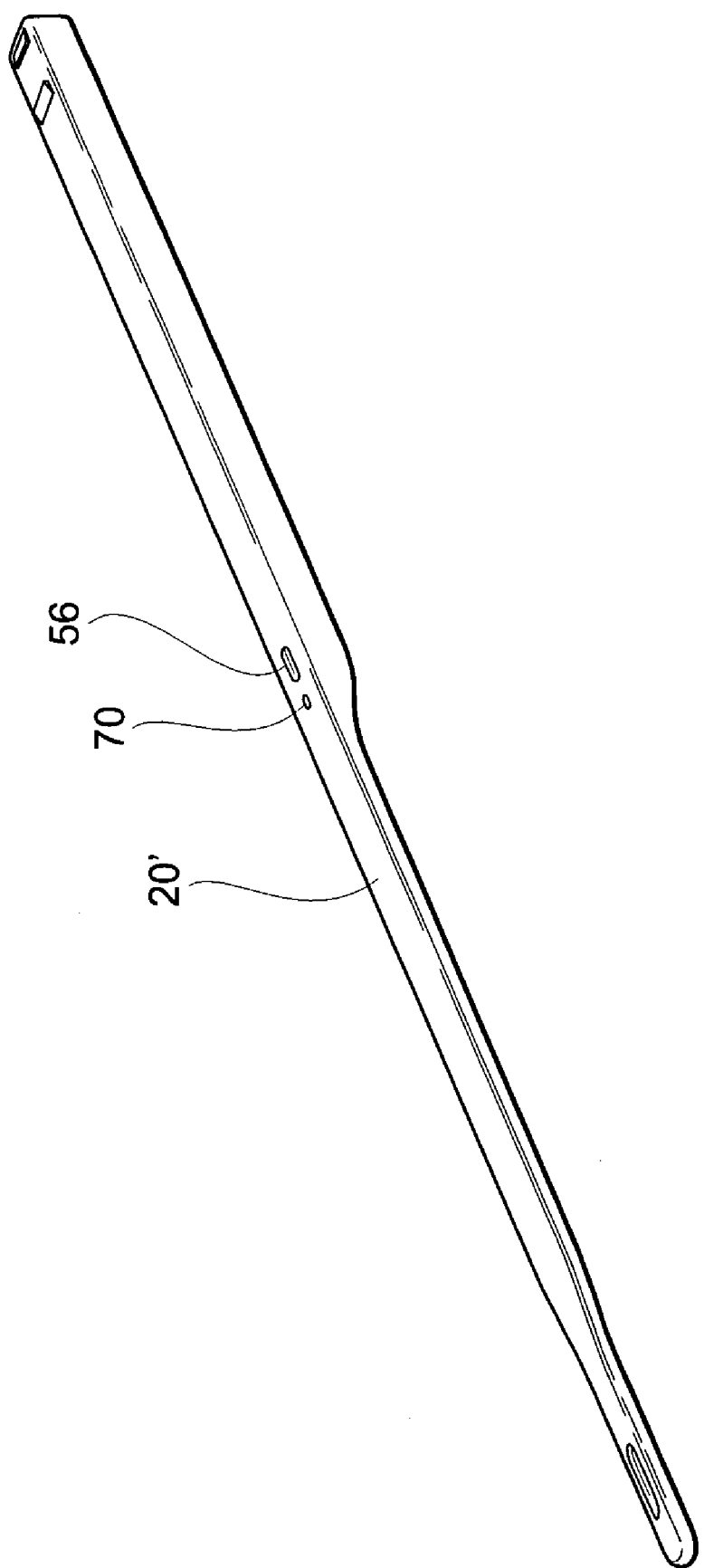
FIG. 12 is a perspective view of a molded basket arm structure that can be used in association with the basket structure shown in FIG. 11.

Irrigation through the balloon structure 26 simplifies the configuration of the basket arms 20 by the elimination of irrigation passages in the arms 20. This simplification also makes possible the construction of a basket arm 20' entirely by molding, instead of extrusion, as FIG. 12 shows. In this arrangement, the electrode openings 56 and the thermocouple openings 70 can be integrally formed in the arm 20' during molding. This eliminates the need for secondary operations to form these features after arm extrusion. Molding the basket arm 20' also makes it possible to integrally form the passage L1 with the desired interior geometry leading to the opening 56, thereby eliminating the need to provide a separately formed insert 154 and to form the ramp segment 156 in a secondary operation, as previously described and as shown in FIG. 7C.

As FIG. 8 shows, the proximal ends 62 of the extruded basket arms 20 are collectively joined to the catheter tube 14 by the base element 24, which also desirably comprises a molded or machined plastic part, comprising, e.g., polycarbonate, or Peek™ plastic material, or Ultem™ plastic material. In the embodiment illustrated in FIG. 8, the base element 24 is shown to comprise a single assembly of a base mount 74. The absence of a base manifold 76 and an interior manifold chamber 78 in the base element 24 is a second difference in construction of the operative element 16' This is because, in this embodiment, irrigation fluid is not channeled through the basket arms 20, but through the balloon structure 26 itself.

The base mount 74 includes an array of circumferential openings 82 (see FIGS. 8 and 9) that are sized and configured to receive and engage the proximal ends 62 of the basket arms 20.

In this arrangement, the base mount 74 includes a first, more central opening 88 (see FIG. 8). This opening 88 is sized and configured to allow fluid-tight passage of an inflation tube 90 for the balloon structure 26, distally beyond the base element 24, as FIG. 9 shows. The inflation tube 90 passes through the catheter tube 14 and through the opening 88 in the base mount 74. The terminal end of the inflation tube 90 is joined to the balloon structure 26.

The inflation tube 90 carries liquid saline or water under pressure into the balloon structure 26, causing its expansion. As FIG. 1 shows, a luer fitting 94 can couple a syringe 96 to the handle 12, to supply the inflation fluid. The same pressurized liquid used to inflate the balloon structure 26 also seeps under pressure from the openings 152 formed in the balloon structure 26 (as FIG. 11 shows). The cooling fluid openings 152 convey irrigation fluid into contact with surface tissue in the regions of the electrode elements 28. Thus, ablation, temperature sensing, and cooling occur generally in the same localized tissue region.

The base mount 74 also includes another, more central opening 98 (see FIG. 8). This opening 98 is sized and configured to allow fluid-tight passage of an aspiration tube 100, as FIG. 9 shows. The aspiration tube 100 passes through the catheter tube 14 and through the opening 98 in the base mount 74, distally beyond the base element 24. The terminal end of the aspiration tube 100 is desirably flush with the distal face of the base element 24. Coupled to the aspiration source 46 (see FIG. 1), the aspiration tube 100 draws irrigation fluid discharged through the openings 152 in the balloon structure 26, away from the operative element 16.

In this embodiment (see FIG. 8), the catheter tube 14 desirably comprises an extruded multiple lumen shaft 140. The co-extruded lumens 142 to 148 in the shaft 140 accommodate passage of the various components that, in use, couple to the operative element 16.

More particularly, one co-extruded lumen 142 accommodates passage of the aspiration tube 100. A second co-extruded lumen 144 accommodates passage of the electrode advancer stylet 118. A third co-extruded lumen 146 accommodates passage of the balloon inflation/irrigation tube 90. A fourth co-extruded lumen 148 accommodates passage of the electrode supply wire 42 and the bundle 68 of thermocouple wires.

In the illustrated embodiment, the extruded shaft 140 includes a scalloped external configuration. This configuration reduces the overall outside diameter of the shaft 140 and allows side-by-side use with an visualization element, as will be described in greater detail later.

The catheter tube 14 also desirably includes a distal shaft component 150. The distal shaft component 150 desirably comprises a molded or machined plastic part, comprising, e.g., polycarbonate, or Pebax™ plastic material, or PET™ plastic material, or Ultem™ plastic material. The distal shaft component 150 is sized and configured at its proximal end to engage the terminus of the extruded catheter shaft 140 in a frictional slide-fit, which can be augmented with the use of adhesive or thermal bonding. The distal shaft component 150 is sized and configured at its distal end to hold and secure the base element 24 of the basket assembly 18 in a frictional slide-fit, which can likewise be augmented with the use of adhesive or thermal bonding. When assembled to the shaft 140 and the base element 24, the distal shaft component 150 encloses the working components of the electrode advancer assembly 58, base element 24, tubes, and wires serving the operative element 16.

IV. The Operative Element

Direct Irrigation Embodiments

In the previous embodiments, irrigation fluid is delivered through a fluid path that is isolated from the basket arm lumen in which the electrode element 28 resides, to keep the mucosa cool during delivery of radio frequency energy. While the technical features of these previous embodiments have distinct benefits, there are also benefits to a construction in which the irrigation fluid is delivered through the same basket arm lumen that contains the electrode element 28. This construction will be generally called "direct irrigation." The benefits of direct irrigation include the delivery of irrigation fluid directly to the base of each electrode element, where the majority of tissue heating is presumed to occur. Direct irrigation also makes it possible to simplify the construction of the operative element, which is of particular benefit when multiple-arm basket structures are required.

Direct irrigation can be accomplished in various ways. Several representative embodiments will be described.

A. Direct Irrigation Using an Irrigation Seal in the Basket Base Element

FIGS. 13 to 19 show one representative embodiment of an operative element 200 that employs direct irrigation. Apart from the structural features that enable direct irrigation, the operative element 200 shares many features of the previously described embodiments of the operative element 16 and 16'. Common reference numbers will be therefore assigned to shorten the description. Previous descriptions of structural elements having the same reference number are incorporated herein.

Figure 13:
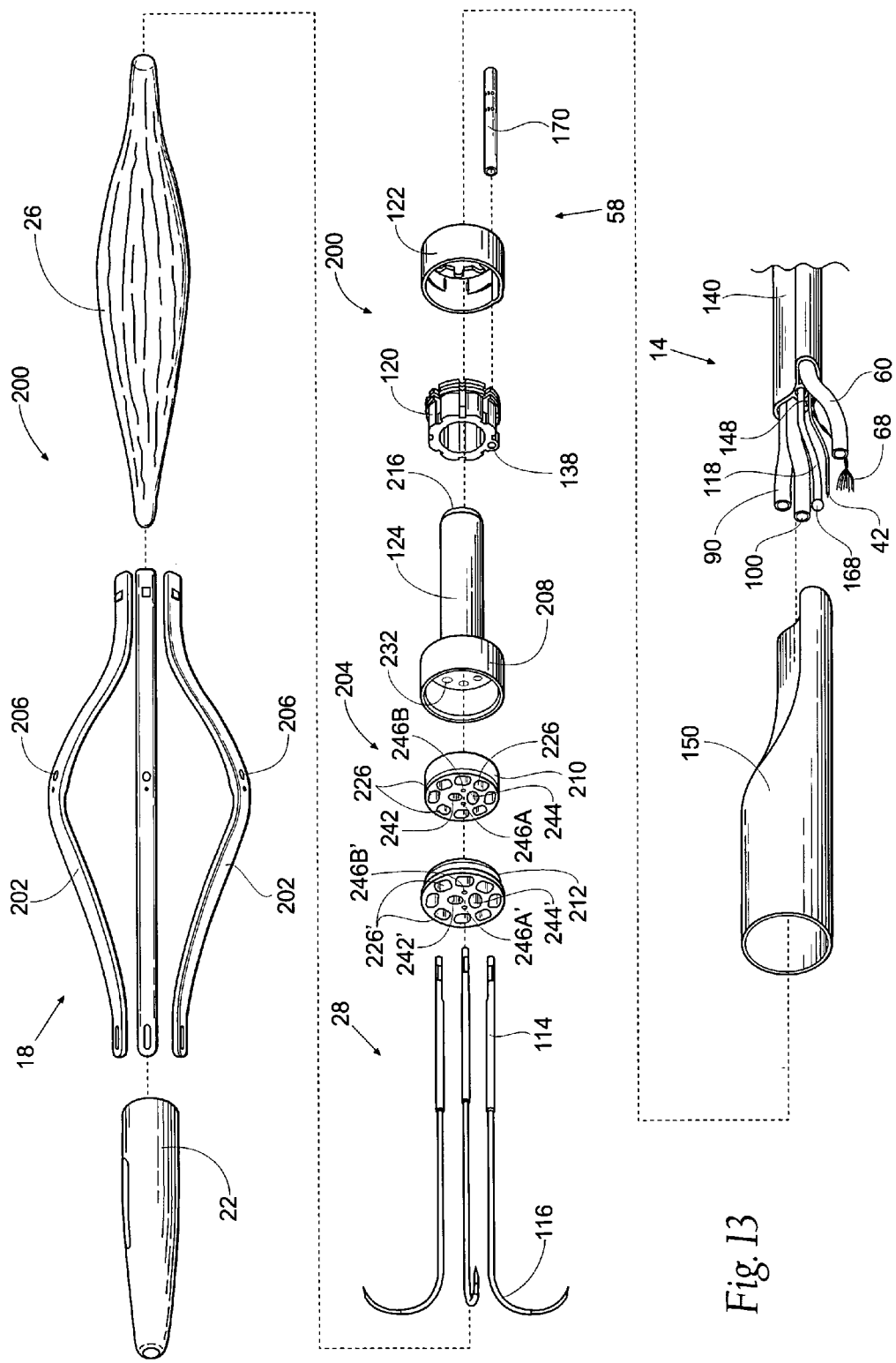
FIG. 13 is an exploded perspective view of the components of another embodiment of an operative element that can be used in association with the treatment device shown in FIG. 1, this operative element providing for cooling of surface tissue by "direct irrigation," i.e., by conducting irrigation fluid through the same basket arm lumens through which the electrode elements are deployed.
Figure 14:
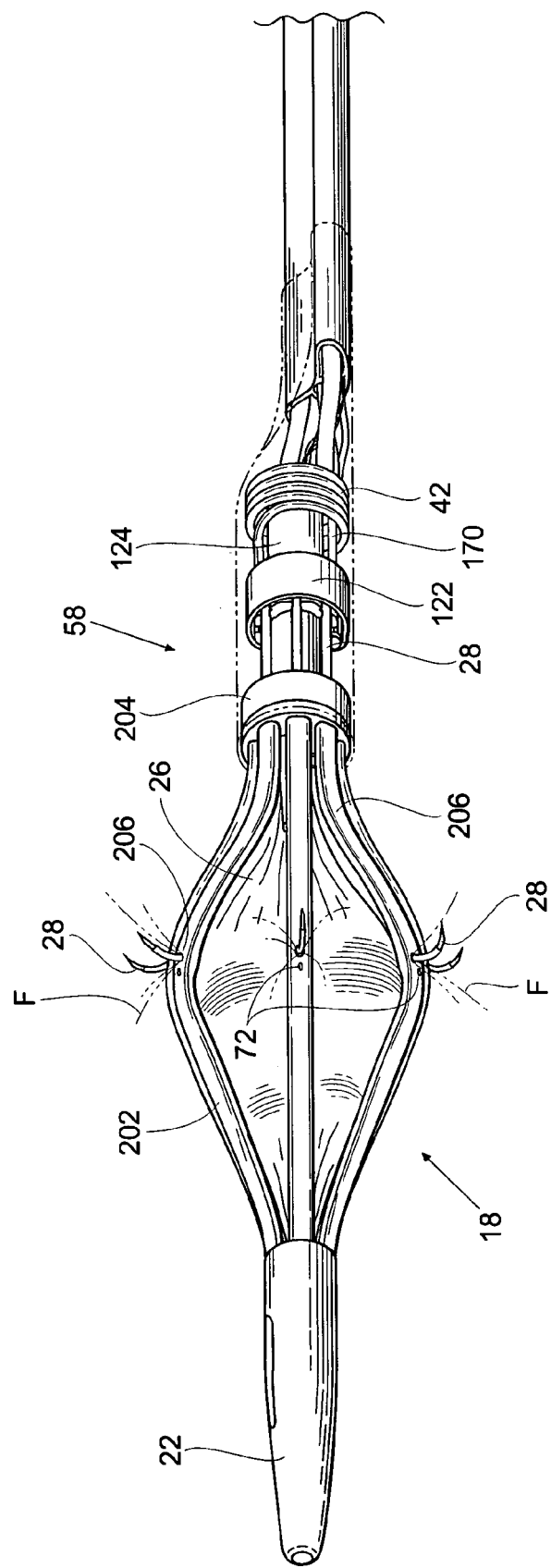
FIG. 14 is an assembled view of the operative element shown in FIG. 13, with the basket structure expanded, the electrode elements deployed through the basket arm lumens, and irrigation fluid being conveyed at the base of each electrode element through the same basket arm lumens, thereby comprising "direct irrigation".

Like the previous embodiments of the operative elements 16 and 16', the operative element shown in FIGS. 13 to 19 comprises a three-dimensional basket 18 (see, e.g., FIGS. 13 and 14). As previously described, the basket 18 includes an array of arms 202. The arms 202 are desirably made from extruded or molded plastic, but they could also be formed from stainless steel or nickel titanium alloy. To accommodate direct irrigation, the arms 202 differ in certain respects from the basket arms 20 previously described, as will be described later.

As shown in FIG. 14, the arms 202 are assembled together between a distal tip 22 (which, in the illustrated embodiment, shares the features of the distal tip 22 previously described) and a proximal base element 204. To accommodate direct irrigation, the base element 204 also differs in certain respects from the previously described base element 24, as will be described later.

The operative element 200 shown in FIGS. 13 to 19 also includes an expandable balloon structure 26 located within the basket 18. As previously described, in use, the balloon structure 26 expands from a generally collapsed condition (as FIG. 13 shows in a non-assembled condition) and an expanded condition (as FIG. 14 shows in an assembled condition). The balloon structure 26 serves to expand the basket structure 18 for the purposes already explained. The balloon structure 26 is like the balloon structure 26 described in the context of the operative element 16 (FIGS. 1 to 7). The balloon structure 26 in FIGS. 13 to 19 differs from the balloon structure 26 described in the context of operative element 16' (FIGS. 8 to 11), due to the absence of the irrigation openings 152, which direct irrigation obviates.

Figure 17A:
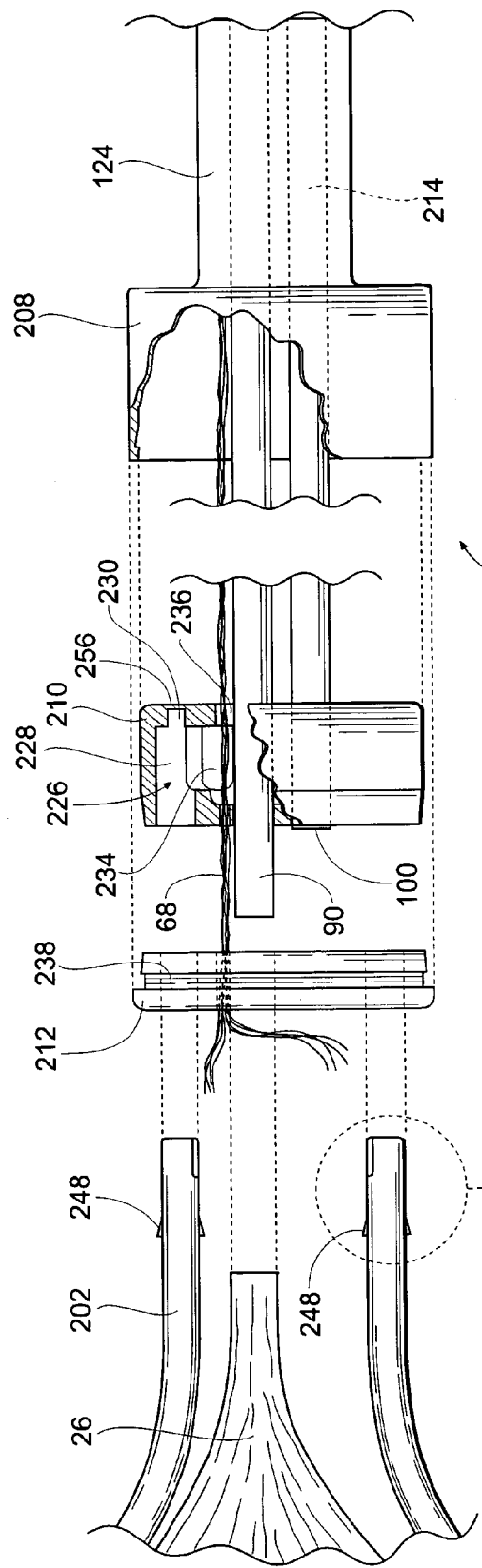
FIG. 17A is an exploded side view, with parts broken away and in section, of a portion of the operative element shown in FIGS. 13 and 14.
Figure 17C:
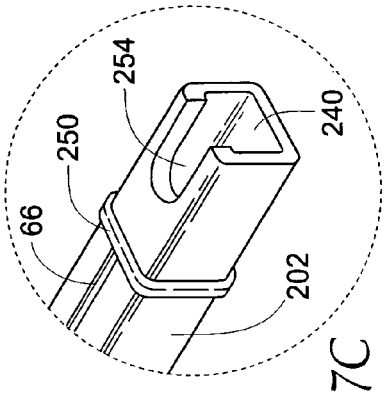
FIGS. 17B and 17C are enlarged perspective views showing alternative embodiments of the proximal end of a basket arm associated with the operative element shown in FIG. 17A.
Figure 17B:
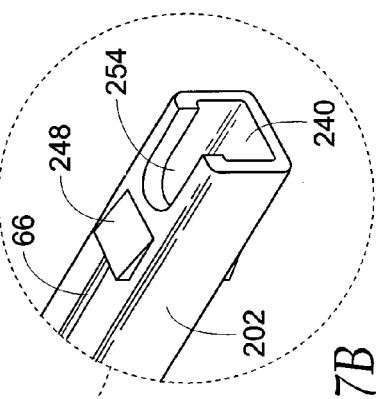

In the embodiment shown in FIGS. 13 to 19, each basket arm 202 possesses a single interior lumen 240 (see FIG. 17B or FIG. 17C). This is like the single lumen basket arm 20 associated with the operative element 16' (which FIGS. 8 to 11 show). When the operative element 200 is assembled, an electrode element 28 resides in the lumen 240 (as best shown in cross section in FIG. 19). As previously explained, in use, the electrode element 28 slides within the lumen 240 between a retracted position (not shown in the FIGS. 13 to 19 drawings) and an extended position (which is shown in FIG. 14). As FIG. 14 shows, the electrode element 28, when extended, projects through an opening 206 in the basket arm and pierces tissue. The electrode element 28, when extended, applies radio frequency energy to heat submucosal tissue.

The electrode elements 28 can be constructed in the same manner previously described in earlier embodiments. Desirably (as FIG. 13 shows), the electrode elements 28 comprise a hybrid of materials comprising stainless steel for the proximal portion 114 and nickel titanium alloy for the distal portion 116.

Figure 19:
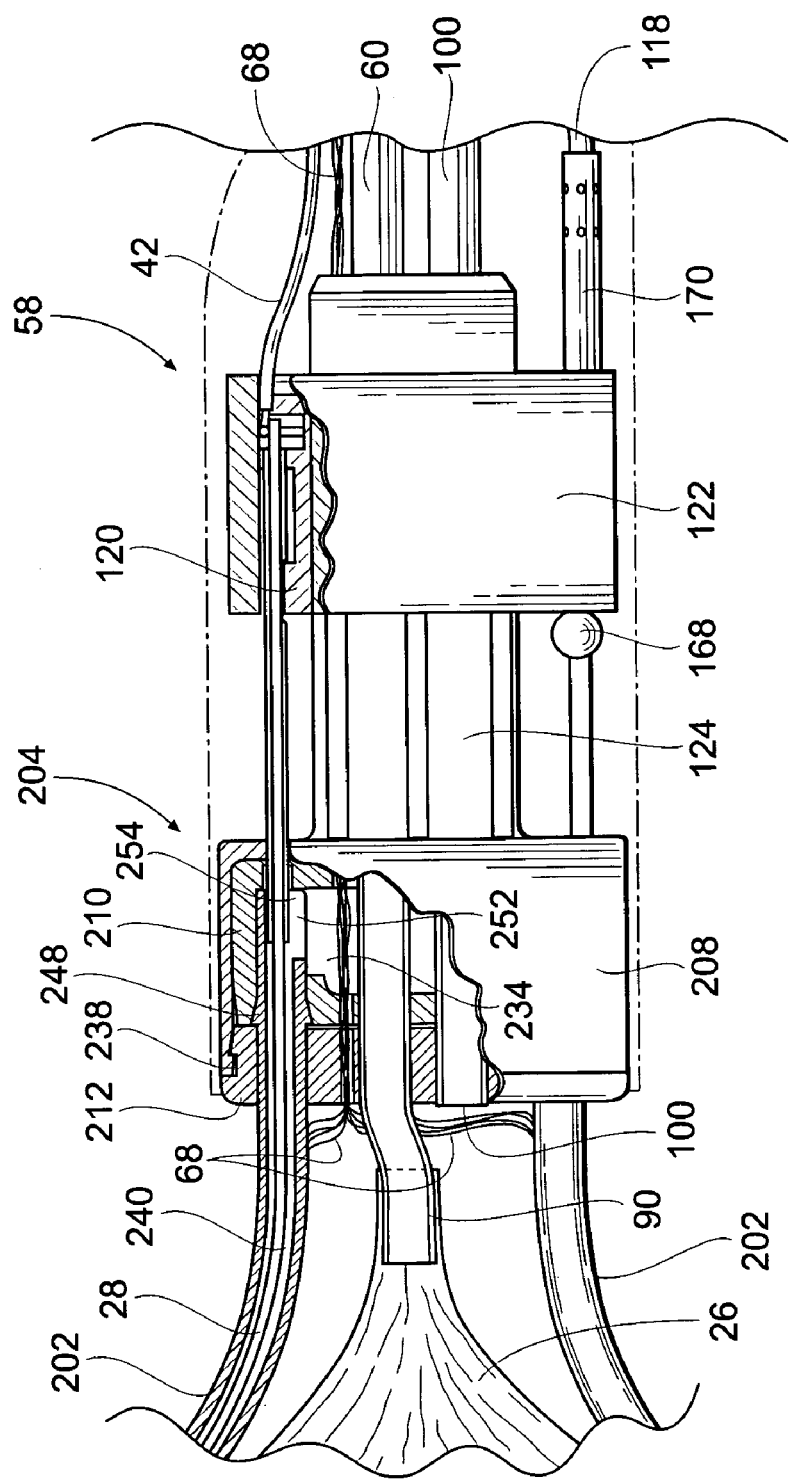
FIG. 19 is an assembled side view of the portion of the operative element shown in FIG. 17A, with parts broken away and in section.
Figure 20:
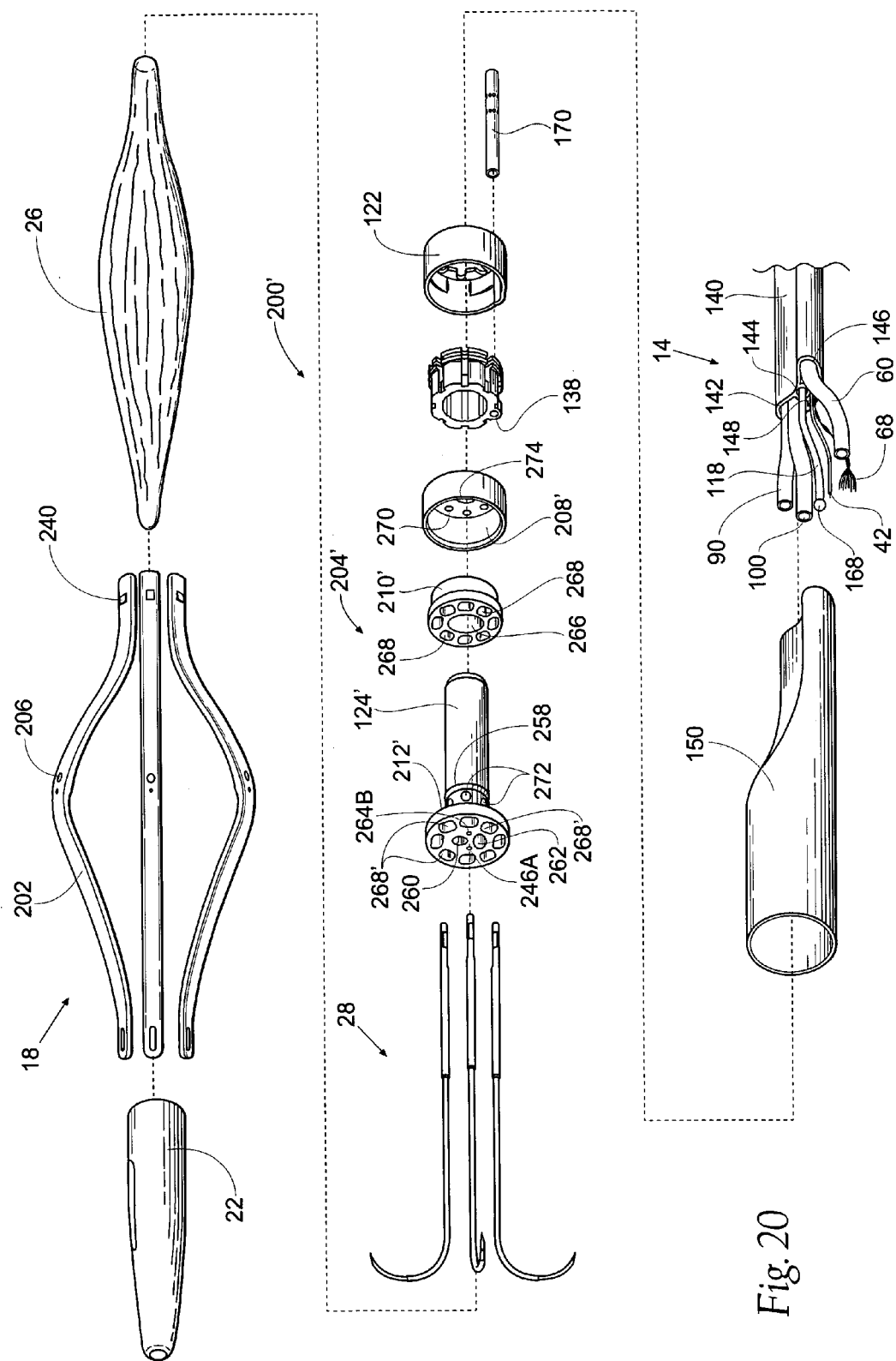
FIG. 20 is an exploded perspective view of the components of another embodiment of an operative element that can be used in association with the treatment device shown in FIG. 1, this operative element providing for cooling of surface tissue by direct irrigation.

As in earlier described embodiments, an electrode advancer assembly 58 is joined to a stylet 118 (see, e.g., FIGS. 14 and 19). The stylet 118 is coupled to a control lever on the proximal end of the catheter tube 18, as generally shown in FIG. 1. Manipulation of the stylet 118 enables retraction and extension of the electrode elements 28 carried within the basket arms 202. The structure of the electrode advancer assembly 58 is the same as previously described. As previously described (see FIG. 19), the assembly of the electrode advancer hub 120 and advancer sleeve 122 (to which the electrode elements 28 are coupled) rides fore and aft along a stem 124 (see also FIG. 14), which is coupled to the proximal base element 204. This advances the electrode elements 28 fore and aft through the basket arms 204. The electrical connections of the electrode supply wires 42 to the proximal ends of the electrode elements 28 are accomplished in the same manner as previously described.

In this embodiment (see FIG. 14), the irrigation fluid (designated F in FIG. 14) is discharged directly at the base of each electrode element 28. The irrigation fluid is conveyed through the same basket arm lumen 240 and is discharged through the same basket arm opening 206 as the electrode element 28. This has been previously referred to as "direct irrigation."

To enable direct irrigation through the basket lumen 240, without leakage of irrigation fluid F, the proximal base element 204 (see FIG. 13) comprises a chamber 208 which holds an irrigation seal member 210. The seal member 210 is enclosed in a fluid-tight manner within the chamber 208 by an irrigation seal cap 212 (the entire assembly is best shown in FIG. 19).

In the illustrated embodiment (see, e.g., FIG. 13), the chamber 208 is formed as an integrated part of the electrode advancer stem 124. The integrated assembly can comprise a molded or machined plastic part, fabricated, e.g., from polycarbonate, or Peek™ plastic material, or Ultem™ plastic material.

To convey irrigation fluid to the chamber 208 (see FIG. 15A), the stem 124 is fabricated to include an open interior passage 214. At its distal end (as best shown in FIG. 17A), the passage 214 enters the chamber 208. At its proximal end (best shown in FIGS. 15A and 15B), a closure wall 216 extends across the passage 214. A series of openings 218, 220, 222, 224 (see FIG. 15B) pass through the wall 216 and into the interior passage 214.

As FIGS. 15A and 15B show, the openings 218, 220, 222, and 224 to are sized and configured to receive in a fluid-tight manner, respectively, the irrigation tube 60, the aspiration tube 100, the balloon inflation tube 90, and the bundle 68 of thermocouple wires. When assembled, these components extend from the extruded shaft 140 of the catheter tube 14 (see FIG. 13) into and through the openings 218, 220, 222, and 224 of the closure wall 216. The irrigation tube 60, the aspiration tube 100, the balloon inflation tube 90, and bundle 68 of thermocouple wires are desirably bonded by adhesive in their respective openings, to assure a secure, fluid-tight junction.

As FIG. 15A shows, the irrigation tube 60 terminates generally flush with the interior surface of the closure wall 216. In use, the tube 60 conveys irrigation fluid into the passage 214 for delivery into the chamber 208.

Figure 18:
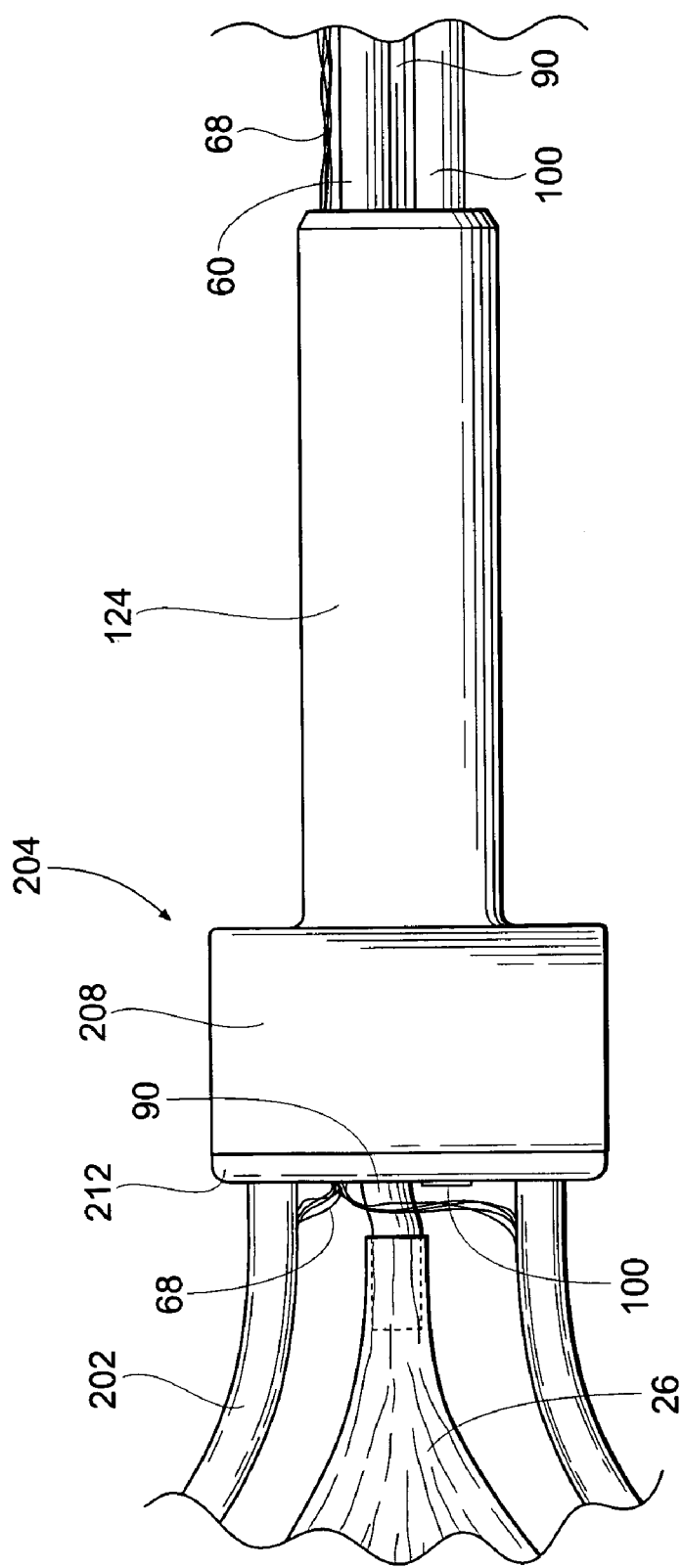
FIG. 18 is an assembled side view of the portion of the operative element shown in FIG. 17A.

The aspiration tube 100, the balloon inflation tube 90, and the bundle 68 of thermocouple wires extend from their respective openings 220, 222, and 224 into and through the fluid-carrying passage 214 (see FIG. 15A). As will be described later (and as FIG. 19 shows), the aspiration tube 100, the balloon inflation tube 90, and the bundle 68 of thermocouple wires pass in a fluid-tight manner through the irrigation seal member 210 within the chamber 208, as well as through the irrigation seal cap 212. The ends of the aspiration tube 100, the balloon inflation tube 90, and the bundle 68 of thermocouple wires thereby ultimately occupy positions outside the distal end of the base element 204 of the basket structure 18, as FIGS. 18 and 19 show.

When assembled, the irrigation seal 210 occupies the chamber 208 into which the irrigation fluid F is conveyed. During assembly (see FIGS. 17A and 19), the irrigation seal member 210 is inserted into the chamber 208 and covered by the irrigation seal cap 212. The seal cap 212 can be formed, e.g., from a molded or machined plastic part fabricated, e.g., from polycarbonate, or Peek™ plastic material, or Ultem™ plastic material. The seal cap 212 includes an annular groove 238 around its perimeter, which mates with an annular rim 239 (see FIGS. 17A and 19) within the chamber 208, to form a fluid-tight closure for the chamber 208. The seal cap 212 also applies sealing compression to the seal member 210 within the chamber 208.

In use (see FIG. 19), the irrigation seal member 210 engages and supports the proximal ends of the basket arms 202 in a fluid-tight manner. The seal member 210 also serves as a manifold to distribute irrigation fluid F introduced into the chamber 208 into each basket arm, also without leakage.

The seal member 210 can be variously constructed to serve these functions. Referring to FIGS. 16A, 16B, and 16C, the irrigation seal member 210 is desirably molded from an elastomeric material, such as silicone, or, alternatively, an elastomeric, injection moldable material such as santoprene. The seal member 210 includes a formed interior manifold region 234. The proximal end of the manifold region 234 (see FIGS. 16B and 16C) has an opening 236. When the seal member 210 is seated in the chamber 208, the opening 236 registers with the fluid-carrying passage 214 of the stem 124. In this manner, irrigation fluid F conveyed by the passage 214 enters the manifold region 234 of the seal member 210.

The aspiration tube 100, the balloon inflation tube 90, and bundle 68 of thermocouple wires carried by the passage 214 also enter the manifold region 234 through the opening 236 (this is shown in FIG. 17A). The seal member 210 includes at the distal end of the manifold region 234 an array of interior openings 242, 244, and 246A/B (see FIGS. 16A and 16C). The openings 242, 244, and 246A/B are sized and configured to pass, respectively the balloon inflation tube 90, the aspiration tube 100, and bundle 68 of thermocouple wires from the manifold region 234 (see FIG. 17A). The irrigation seal cap 212 likewise includes an array of interior openings 242', 244', and 246A/B' (see FIG. 13), which overly and register with the seal member openings 242, 244, and 246A/B, respectively, allowing passage of the aspiration tube 100, the balloon inflation tube 90, and bundle 68 of thermocouple wires outside of the base element 204 (as FIGS. 18 and 19 show). In the illustrated embodiment, the bundle 68 of thermocouple wires is separated into two bundles and passed through two interior openings 246A/B and 246A/B' formed for that purpose. The elastomeric material of the seal member 210 peripherally engages the aspiration tube 100, the balloon inflation tube 90, and bundle 68 of thermocouple wires in a fluid-tight manner, to prevent leakage of irrigation fluid from the base element 204.

The seal member 210 further includes a peripheral array of basket arm support lumens 226 (see FIGS. 16A and 16C). The irrigation seal cap 212 (see FIG. 13) likewise includes an array of peripheral openings 226', which overlay and register with the basket arm support lumens 226 in the seal member 210. This arrangement accommodates the insertion of the proximal ends of the basket arms 202 through the cap 212 and into the support lumens 226 of the seal member 210, as FIG. 19 shows. The elastomeric material of the seal member 210 peripherally engages the basket arms within the support lumens 226 in a fluid-tight manner, to resist leakage or seepage of irrigation fluid about the exterior of the basket arms 202. The basket arm support lumens 226 in the seal member 210 also make possible the connection of the basket arms 202 to the basket base element 204 without using adhesive. A barb 248 can be provided on the proximal end of each basket arm 202 (see FIG. 17B). The barb 248 snap-fits against the interior of cap 212 as the basket arm 202 is inserted through the cap 212 (see FIG. 19), to resist subsequent pull-out of the basket arm 202 from the cap 212. Alternatively, as shown in FIG. 17C, a flange 250 on the proximal end of the basket arm 202 could accomplish the same function. In this arrangement, however, the cap 212 is desirably secured to the chamber 208 after insertion of the basket arms 202 into the support lumens 226.

In the illustrated embodiment (see FIG. 16C), each support lumen 226 in the seal member 210 is internally stepped to form a larger diameter distal portion 228 and a smaller diameter proximal portion 230. Each larger diameter distal portion 228 is sized and configured to accommodate and engage the proximal end of an inserted basket arm 202 in a fluid-tight manner (see FIG. 19). The larger diameter distal portion 228 also includes a cut-out that forms an inlet passage 252, which opens communication between the manifold region 234 and the respective lumen 226.

In this arrangement (see FIG. 17B or 17C), the proximal end of each basket arm 202 includes a side notch 254. The side notch 254 provides entry into the basket lumen 240 through a side of the basket arm 202. When a basket arm 202 is properly inserted within its support lumen 226, the notch 254 registers with the cut-out inlet passage 252 in the support lumen 226. In this way, irrigation fluid flowing into the manifold region 234 is free to enter the lumen 240 of each basket arm 202. Direct passage of irrigation fluid through the lumen 240 and out the electrode opening 206 in each basket arm 202 is thereby enabled.

Each smaller diameter proximal portion 230 of the support lumen 226 is sized and configured to accommodate in a fluid-tight manner the electrode element 28 carried by the associated basket arm (see FIG. 19). The electrode elements 28 pass from the hub 120 and sleeve 122 of the advancer assembly through corresponding openings 232 (see FIG. 13) formed in the base of the chamber 208. When the seal member 210 is properly inserted into the chamber 208, the openings 232 register with the proximal portions 230 of the support lumens 226. A web of elastomeric material is present between each proximal lumen portion 230 and the corresponding chamber opening 232 for the electrode elements 28, to serve as a fluid-tight septum 256 (see FIG. 16C), through which the electrode element 28 passes before entering its basket arm lumen 240.

Outside the base element 204 (see FIGS. 18 and 19), the balloon inflation tube 90 is joined to the balloon structure 26. The aspiration tube 100 is positioned generally flush with the exterior surface of the base element 204. The thermocouple wire bundles 68 are separated out into individual pairs of thermocouple wires and routed individually through the grooves 66 (see FIG. 17B or 17C) formed for this purpose in the basket arms 20, to form the joined temperature sensing elements 72 (see FIG. 14) adjacent each electrode/irrigation opening 206.

FIGS. 20 to 23A/B/C show an alternative embodiment of an operative element 200' that enables direct irrigation. In this embodiment, like the first-described direct irrigation embodiment, a basket base element 204' holds an interior seal member 210', which serves both to support an array of basket arms 202 as well as distribute irrigation fluid through the same lumen 240 in each basket arm 202 that also carries the electrode element 28. As in the first-described direct irrigation embodiment, the seal member 210' of the base element 204' is enclosed in a fluid-tight manner within the chamber 208' by an irrigation seal cap 212'.

In the alternative embodiment shown in FIGS. 20 to 23A/B/C, the chamber 208' comprises a separate molded or machined plastic part, fabricated, e.g., from polycarbonate, or Peek™ plastic material, or Ultem™ plastic material. In this arrangement, the seal cap 212' (and not the chamber 208' itself) is formed as an integrated part of the electrode advancer stem 124'. The integrated assembly can comprise a molded or machined plastic part, fabricated, e.g., from polycarbonate, or Peek™ plastic material, or Ultem™ plastic material.

In the embodiment shown in FIGS. 20 to 23 A/B/C, the seal member 210' and the chamber 208' are assembled on the stem 124' from its proximal end. The seal member 210' is advanced along the stem 124' from its proximal end (through the opening 266 in the seal member, shown in FIG. 20) until it seats against the seal cap 212' (see FIG. 22). Following placement of the seal member 210', the chamber 208' can be advanced along the stem 124' from its proximal end (through the opening 274, shown in FIG. 20) over the seal member 210' (see FIGS. 21 and 22). The chamber 208' compresses the seal member 210' within the chamber 208'. The chamber 208' is retained against the seal cap 212' by snap-fit engagement with a flange 258 on the stem 124' (see FIGS. 21 and 22).

Figure 22:
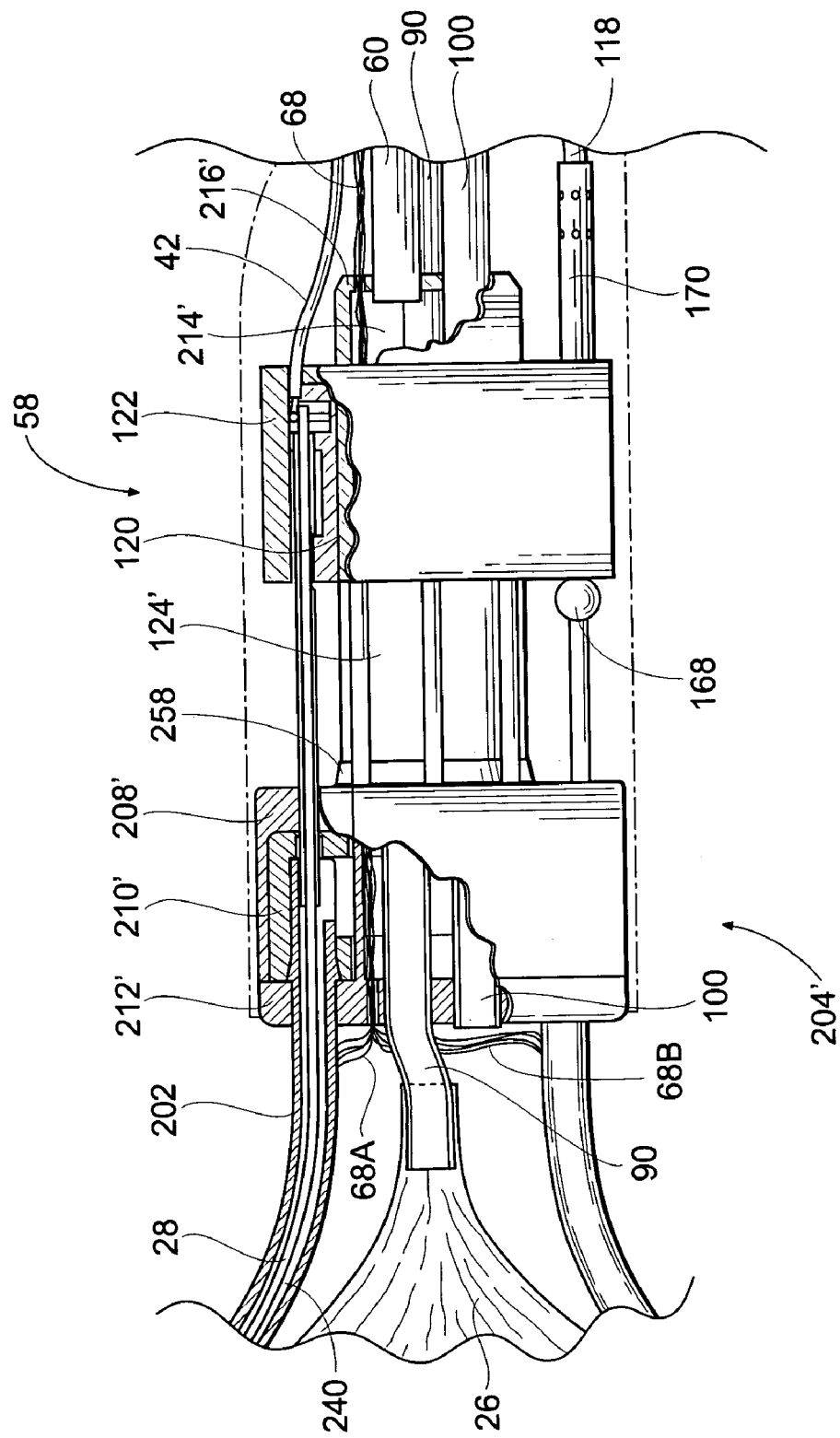
FIG. 22 is an assembled side view of the portion of the operative element shown in FIG. 21, with parts broken away and in section.

As in the previous direct irrigation embodiment, and as FIG. 22 shows, the stem 124' includes an open interior passage 214'. The irrigation tube 60 is bonded to the proximal end of the stem 124' (through an opening in a proximal closure wall 216', in the same manner shown in FIGS. 15A and 15B). As FIG. 22 shows, the irrigation tube 60 terminates generally flush against the interior of the closure wall 216', to convey irrigation fluid into the passage 214'. The irrigation fluid F is intended to exit the passage 214' through an array of side openings 272 (see FIG. 20) formed near the cap 212'. This fluid path will be explained in greater detail later.

Figure 21:
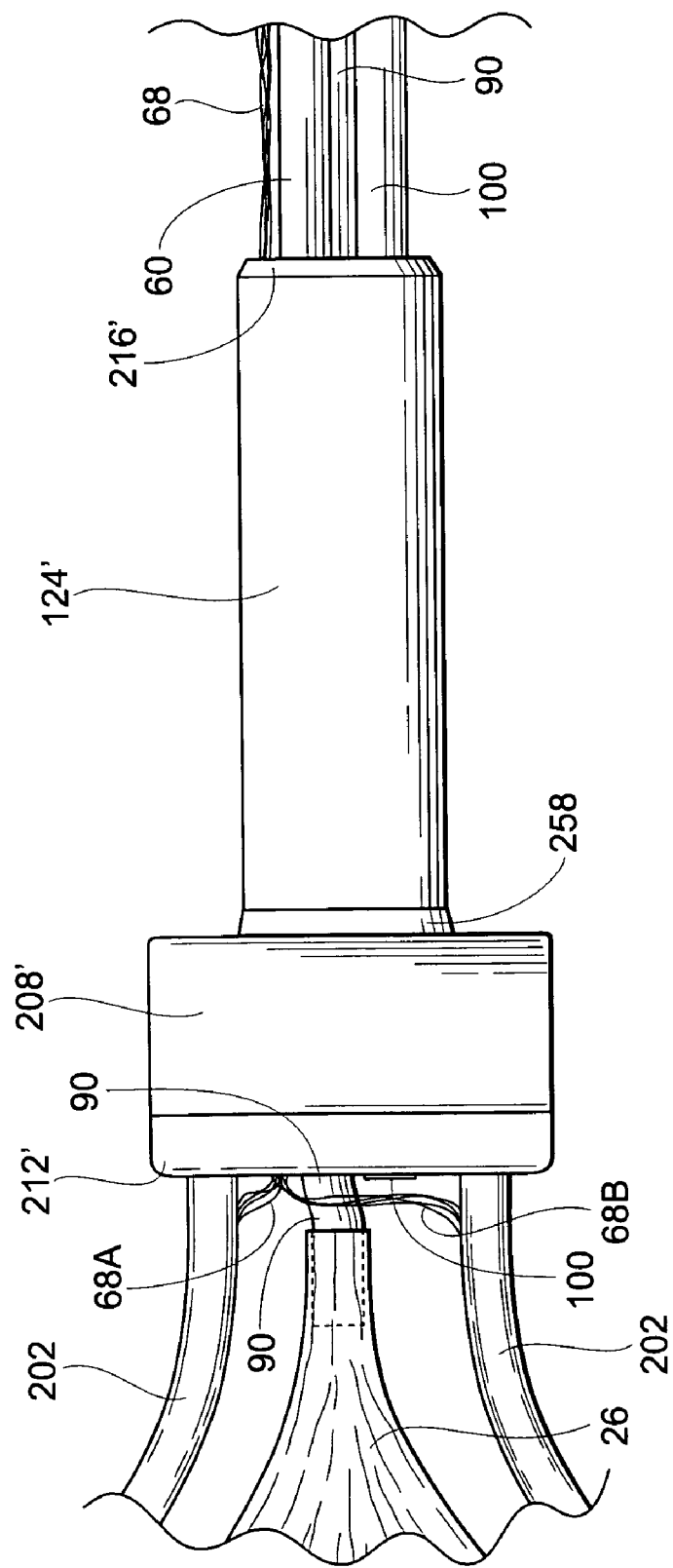
FIG. 21 is an assembled side view of the portion of the operative element shown in FIG. 20.

The aspiration tube 100, the balloon inflation tube 90 and the bundle 68 of thermocouple wires traverse the entire length of the passage 214' (through openings in a proximal closure wall 216', also in the same manner shown in FIGS. 15A and 15B). The balloon inflation tube 90, the aspiration tube 100, and the bundle 68 of thermocouple wires exit the passage 214' through an array of openings, respectively, 260, 262, and 264A/B, in the seal cap 212'. The aspiration tube 100, the balloon inflation tube 90, and the bundle 68 of thermocouple wires are desirably bonded by adhesive to these openings to prevent leakage of irrigation fluid from the cap 212'. The ends of the aspiration tube 100, the balloon inflation tube 90, and the bundle 68 of thermocouple wires occupy positions outside the cap 212', as FIGS. 21 and 22 show. Outside the base cap 212' (see FIGS. 21 and 22), the balloon inflation tube 90 is joined to the balloon structure 26. The aspiration tube 100 is positioned generally flush with the exterior surface of the base element 204'. The thermocouple wire bundle 68 is separated out into the two groups of thermocouple wires 68A and 68B and routed individually through the grooves 66 of the basket arms 202 (as shown, e.g., in FIG. 17B), to form the temperature sensing elements adjacent each electrode/irrigation opening 206.

When assembled (see FIG. 22), the irrigation seal member 210' occupies the chamber 208', into which the irrigation fluid F is conveyed through the side openings 272. As in the first-described direct irrigation embodiment, the seal member 210' is molded from an elastomeric material, such as silicone, or, alternatively, an elastomeric, injection moldable material such as santoprene. In generally the same fashion as the first described seal member 210, the seal member 210' includes a formed interior manifold region 234'. The center opening 266 of the seal member 210 passes through the entire manifold region 234', and the stem 124', when assembled, therefore also extends through the entire manifold region 234'. Irrigation fluid F in the stem passage 214' enters the manifold region 234' via the array of side openings 272 in the stem 124, which are aligned with the manifold region 234'.

As in the first-described direct irrigation embodiment, the seal member 210' includes a peripheral array of basket arm support lumens 268 (see FIGS. 23A and 23C). The irrigation cap 212 (see FIG. 13) includes an array of peripheral openings 268', which overlay and register with the basket arm support lumens 268 in the seal member 210'. This arrangement accommodates the insertion of the proximal ends of the basket arms 202 through the cap 212' and into the support lumens 268 of the seal member 210', as FIG. 22 shows. In the same fashion as the previously described embodiment, the elastomeric material of the seal member 210' peripherally engages the basket arms within the support lumens 268 in a fluid-tight manner, to resist leakage or seepage of irrigation fluid about the exterior of the basket arms 202. A barb 248 (see FIG. 20) can be provided on the proximal end of each basket arm 202 to resist pull-out of the basket arm 202 from the cap 212. The support lumens 268 in the seal member 210' make possible the connection of the basket arms 202 to the basket base element 204' with using adhesive.

The basket arm support lumens 268 communicate with the manifold region 234' through cut-out inlet passages 252' (see FIG. 23B). As in the first-described direct irrigation embodiment (shown in FIG. 17B), the proximal end of each basket arm 202 includes a side notch 254. When a basket arm 202 is properly inserted within its support lumen 268, the notch 254 registers with the cut-out inlet passage 252' in the support lumen 268. In this way, irrigation fluid flowing into the manifold region 234' from the stem passage 214' (through the side openings 272) is free to enter the lumen 240 of each basket arm 202. Direct passage of irrigation fluid through the lumen 240 and out the electrode opening 206 in each basket arm 202 is thereby enabled.

In the same fashion as described with respect to the first-described direct irrigation embodiment, the electrode elements 28 extend from the hub 120 and sleeve 122 of the advancer assembly 58 into the basket arm lumen 240 (see FIG. 22), passing through the openings 270 (see FIG. 20) formed in the base of the chamber 208' and a web of elastomeric material that forms a fluid-tight septum 256' in the seal member 210'. The electrical connections of the electrode supply wires 42 to the proximal ends of the electrode elements 28 are accomplished in the same manner as previously described.

In the first and second-described direct irrigation embodiments, irrigation fluid F is distributed to the basket arms lumens through the basket base element 204 or 204'. In these embodiments, an elastomeric seal member 210 or 210' occupies a chamber 208 or 208' that forms a part of the basket base element 204 or 204'. Within the chamber 208 or 208', the seal member 210 or 210' prevents leakage of irrigation fluid from the basket base element 204 or 204 by providing a fluid-tight seal around both the basket arms (i.e., by virtue of the lumens 226 or 268 in the seal member) and the electrode elements (i.e., by virtue of the stepped down portion of the lumens 226 or 268 and the septum 256 or 256' in the seal member, through which the electrodes pass into the basket base element). In this arrangement, the seal member 210 or 210' also serves to support the proximal ends of the basket arms 202 within the basket base element 204 or 204' (i.e., within the lumens 226 or 268).

This obviates the need to apply adhesive to secure the proximal ends of the basket arms to the basket base element 204 or 204'.

Figure 24:
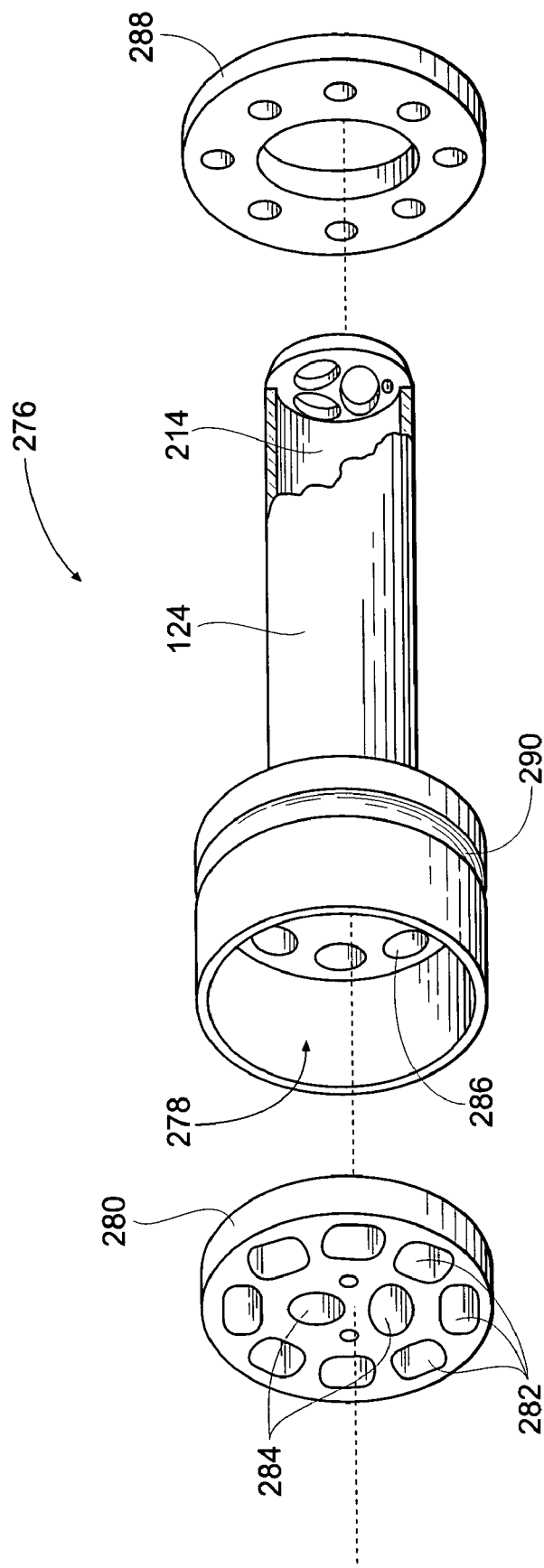
FIG. 24 is an exploded perspective view of a portion of an operative element showing yet another structural arrangement that provides for cooling of surface tissue by direct irrigation, but without use of an interior seal member to support and seal the basket arms in the manner shown in FIGS. 17A/B/C or FIGS. 23A/B/C.

Alternatively, direct irrigation can be accomplished through the basket base element without use of a seal member within the interior of the basket base element. In this arrangement (see FIG. 24), a basket base element 276 can include a irrigation chamber 278 carried at the end of the electrode advancer stem 124. A cap 280 covers the chamber 278, being secured in a fluid-tight manner, e.g., by adhesive. The proximal ends of the basket arms 202 are inserted into the chamber 278 through lumens 282 in the cap 280. The basket arms 202 are secured in a fluid-tight manner within the lumens 282, e.g., by adhesive.

Figure 26:
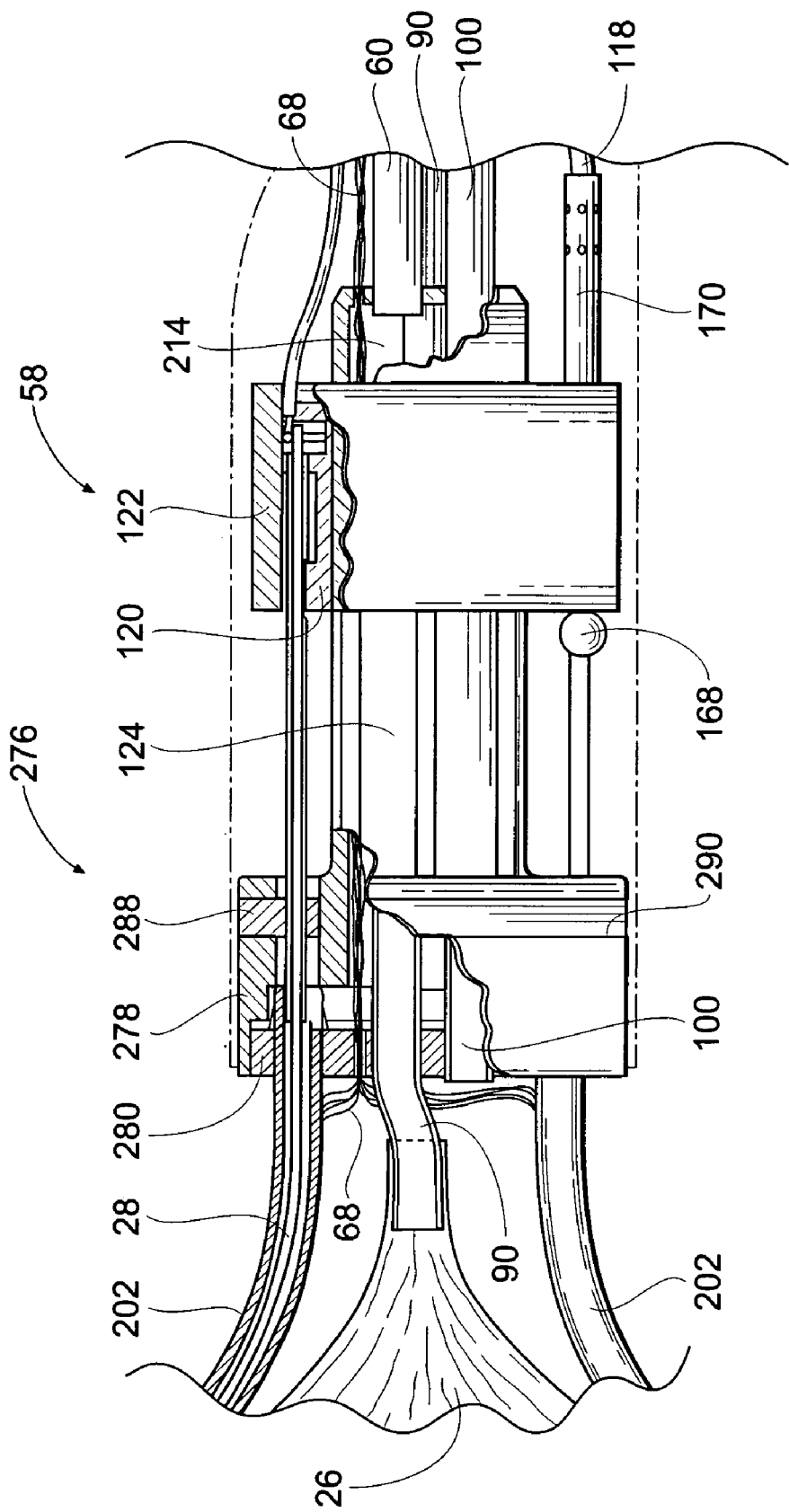
FIG. 26 is an assembled side view, with parts broken away and in section, of the operative element shown in FIG. 25.

In this arrangement, the proximal ends of the basket arms 202, which occupy the chamber 278, can include a single lumen L1, as shown in FIG. 10. The lumen L1 carries the electrode element 28 as well as irrigation fluid, thereby enabling direct irrigation. Irrigation fluid is conveyed directly into the chamber 278 for entry into the lumens L1, via an interior passage 214 in the stem 124 (see FIG. 26), which is coupled to the irrigation tube 60, as previously described in the first and second direct irrigation embodiments. As FIG. 26 also shows, the balloon inflation tube 90, the aspiration tube 100, and the bundle 68 of thermocouple wires also pass through the stem passage 214 and chamber 278, and exit the basket base element 276 through lumens 284 in the cap 280 (see FIG. 24), as previously described. These components are secured, e.g., by adhesive, in a fluid-tight manner within the lumens 284.

Figure 25:
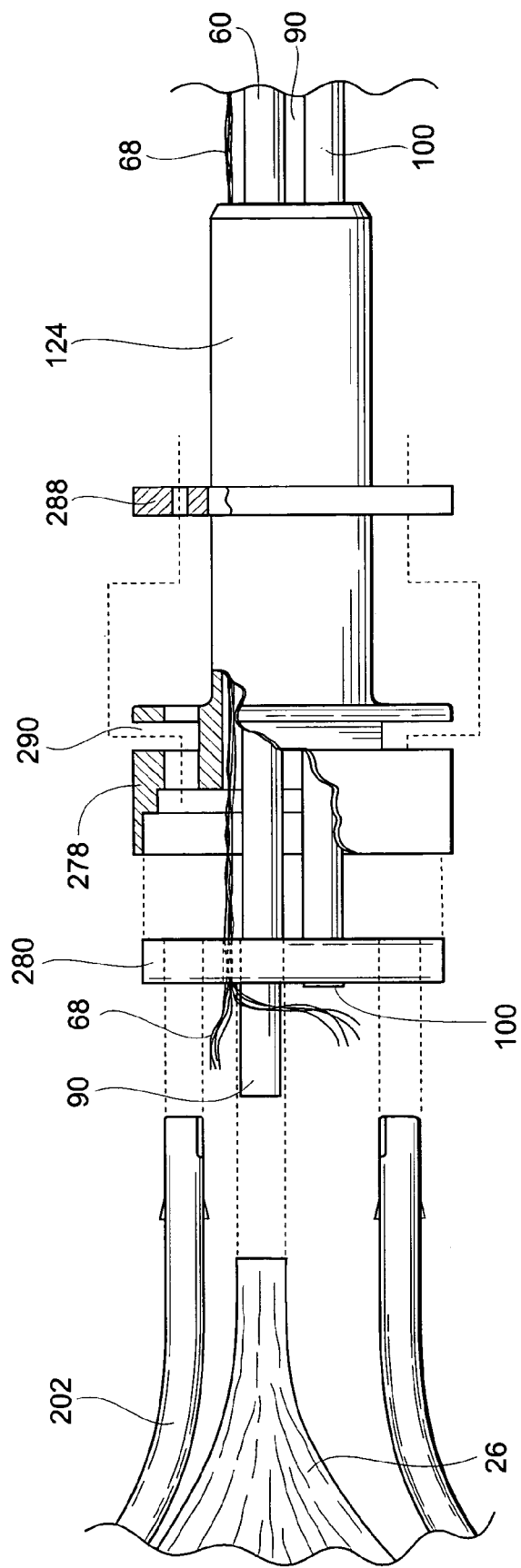
FIG. 25 is an exploded side view, with parts broken away and in section, of an operative element that incorporates structural arrangement shown in FIG. 24.

In the same fashion as described with respect to the first and second-described direct irrigation embodiments, the electrode elements 28 extend from the hub 120 and sleeve 122 of the advancer assembly 58 into the basket arm lumen 240 (see FIG. 26), passing through openings 286 (see FIG. 24) formed in the base of the chamber 278. In this arrangement (see FIG. 26), an elastomeric seal member 288 occupies a groove 290 (see FIG. 24 as well) through which the openings 286 extend. The electrode elements 28 pass through the seal member 288, which forms a fluid-tight seal about the electrode elements 28. In the illustrated embodiment (see FIGS. 24 and 25), the seal member 288 comprises a separate annular ring which is molded from an elastomeric material, such as silicone, or, alternatively, an elastomeric, injection moldable material such as santoprene. During assembly (as FIG. 25 shows), the seal member 288 is advanced over the stem 124 from its proximal end and inserted by stretching into the groove 290. The electrical connections of the electrode supply wires 42 to the proximal ends of the electrode elements 28 are accomplished in the same manner as previously described.

In this arrangement, the seal member 288 does not provide either a sealing function or a support function for the basket arms. The seal member 288 serves only to seal around the electrode elements 28 in the region where they enter the irrigation manifold chamber 278.

B. Direct Irrigation Using an Irrigation Seal in the Catheter Tube

Figure 27:
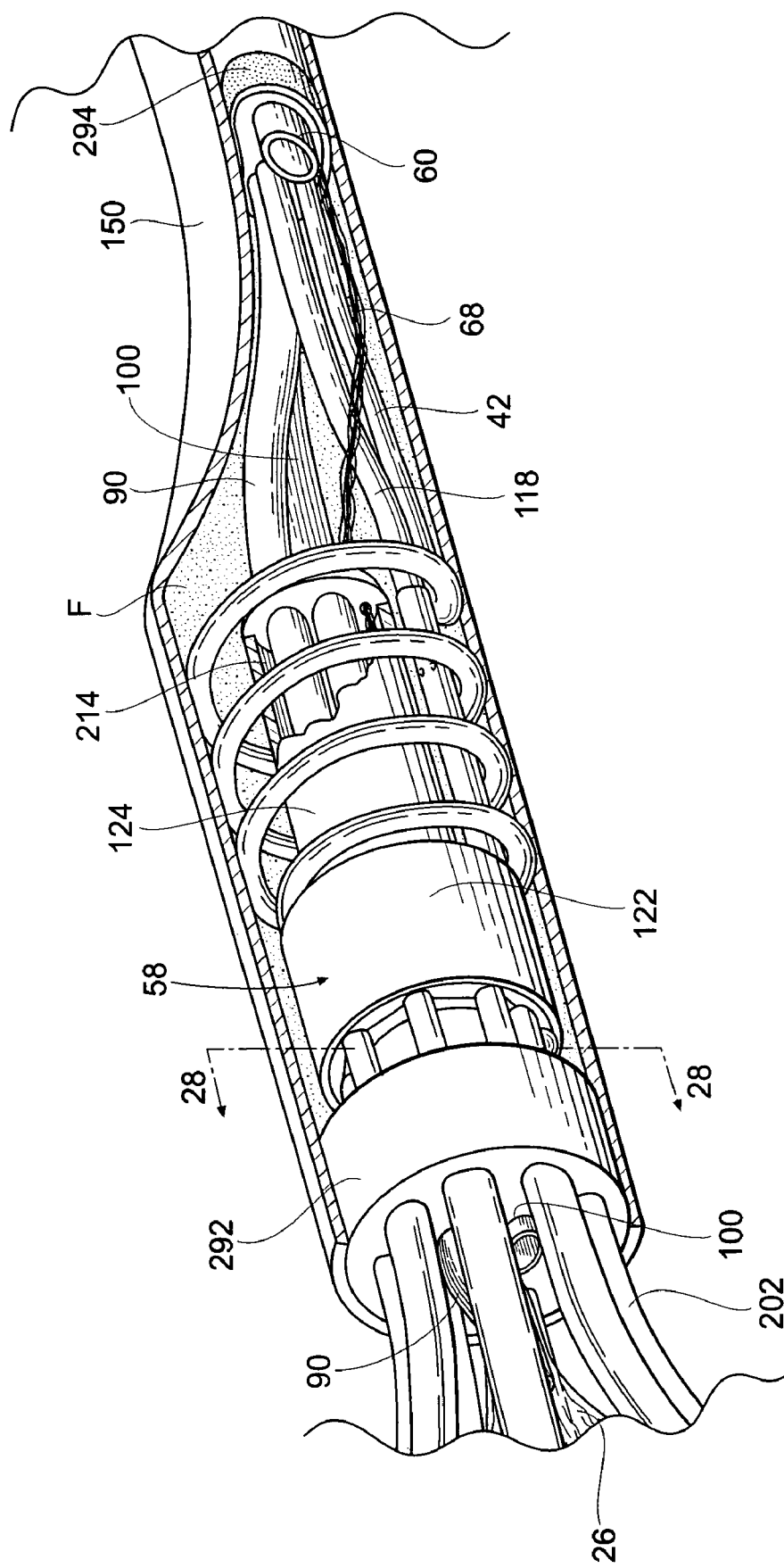
FIG. 27 is an enlarged perspective view of an operative element showing yet another structural arrangement that provides for cooling of surface tissue by direct irrigation, by conveyance of irrigation fluid directly through the distal catheter shaft component on which the operative element is carried.
Figure 28:
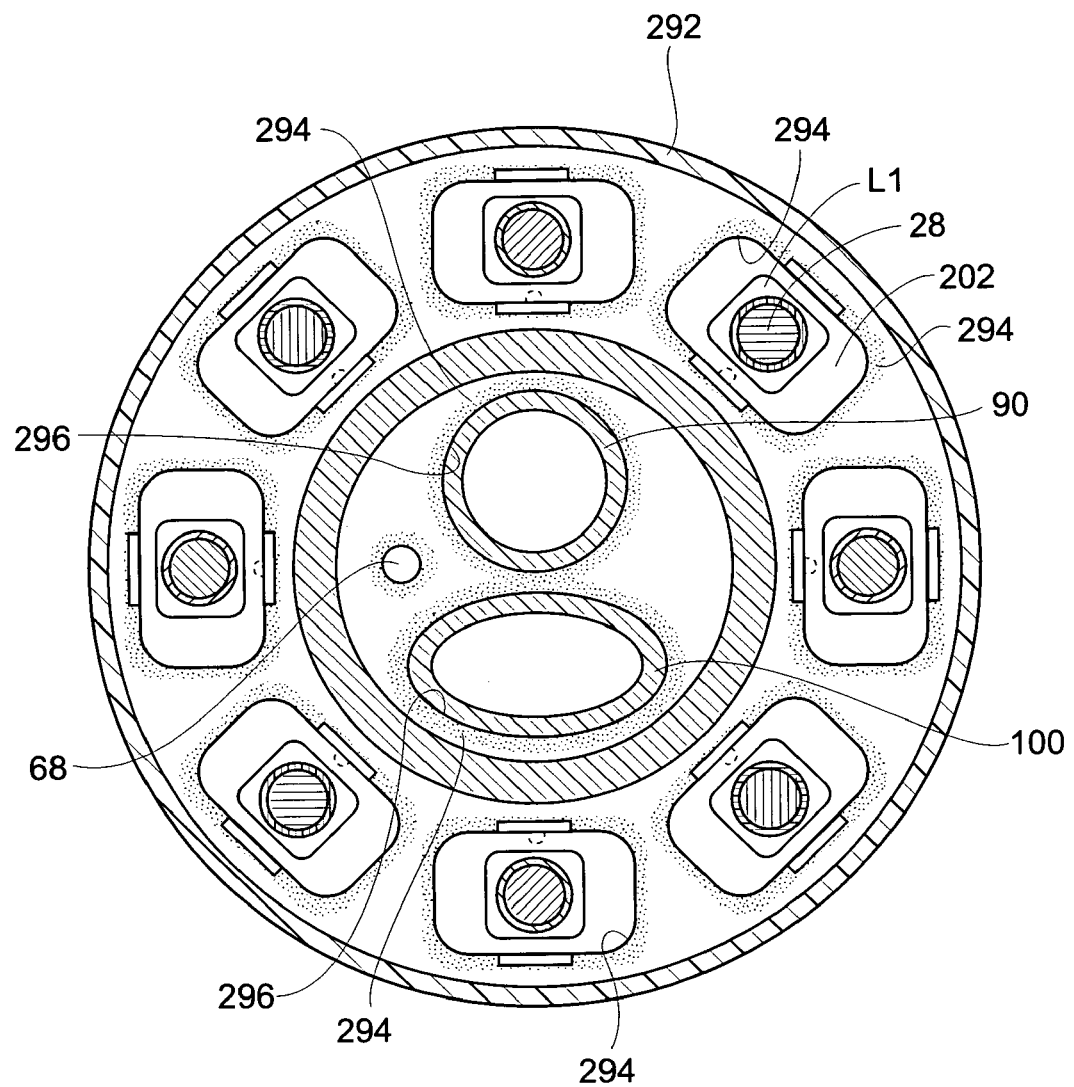
FIG. 28 is a section view taken generally along line 28-28 in FIG. 27.

FIGS. 27 and 28 show yet another embodiment in which direct irrigation can be accomplished. This embodiment shares many of the same features of earlier described embodiments with regard to the basket structure, needle advancer element, etc., and common reference numbers have thereby been assigned to shorten the description. In this embodiment (see FIG. 24), however, a basket base element comprises a single piece hub component 292 that is formed as an integrated part of the electrode advancer stem 124. The integrated assembly can comprise a molded or machined plastic part, fabricated, e.g., from polycarbonate, or Peek™ plastic material, or Ultem™ plastic material. In this direct irrigation embodiment, the basket base hub component 292 is free of any elastomeric seal member.

In this embodiment, the proximal ends of the basket arms 202 are secured in a fluid-tight manner within lumens 294 the hub component 292 (see FIG. 28), e.g., by an adhesive bond 294. In this arrangement, the proximal ends of the basket arms 202 can include a single lumen L1, as shown in FIG. 28 (as well as FIG. 10). As FIG. 28 shows, the lumen L1 carries the electrode element 28 as well as irrigation fluid, thereby enabling direct irrigation. As FIG. 28 also shows, the balloon inflation tube 90, the aspiration tube 100, and the bundle 68 of thermocouple wires also pass through lumens 296 in the hub component 292, for location outside the hub component 292 to perform their intended functions. These components are secured, e.g., by adhesive bonds 294, in a fluid-tight manner within the lumens 296.

Outside the hub component 292 (see FIG. 28), the balloon inflation tube 90 is joined to the balloon structure 26. The aspiration tube 100 is positioned generally flush with the exterior surface of the hub component 292. The thermocouple wire bundle 68 is separated out into the two groups of thermocouple wires 68A and 68B and routed individually through the grooves 66 of the basket arms 202 (as shown, e.g., in FIG. 17B), to form the crimped temperature sensing elements adjacent each electrode/irrigation opening 206.

In this arrangement, irrigation fluid is conveyed directly to the lumens L1 through the previously described distal shaft component 150. The distal shaft component 150—which desirably comprises a molded or machined plastic part, comprising, e.g., polycarbonate, or Pebax™ plastic material, or PET™ plastic material, or Ultem™ plastic material—is secured at its proximal end to the terminus of the extruded catheter shaft 140, which carries the irrigation tube 60, as well as other components serving the operative element. The distal shaft component 150 holds and secures at its distal end the hub component 292. When so assembled, the distal shaft component 150 encloses the working components of the electrode advancer assembly 58, tubes, and wires serving the operative element. It also forms a passage capable of carrying liquid.

In this arrangement (see FIG. 27), the irrigation tube 60 is terminated adjacent the terminus of the extruded catheter shaft 140. Irrigation fluid F conveyed by the tube 60 can thereby be directed into the interior of the distal shaft component 150. The irrigation fluid fills the entirety of the distal shaft component 150, and will flow into the open lumens L1 of the basket arms 202 secured to the hub component 292. Direct irrigation is thereby enabled.

As FIG. 27 also shows, the balloon inflation tube 90, the aspiration tube 100, and the bundle 68 of thermocouple wires also pass within the fluid-filled space of the distal shaft component 150, through the stem passage 214, and exit the hub component 292 through the lumens 296 provided for this function, as previously described.

In this arrangement (see FIG. 27), an adhesive bond 294 forms a fluid-tight junction between the distal shaft component 150 and the catheter shaft 140. The bond 294 also encapsulates or "pots" the lumens of the catheter shaft 140, to create fluid-tight seals about the irrigation tube 60, the aspiration tube 100, the balloon inflation tube 90, the electrical wires 40, the bundle 68 of thermocouple wires, and the electrode advancer stylet 118 carried within the catheter shaft lumens. The bond 294 prevents leakage of irrigation fluid at the junction between the distal shaft component 150 and catheter shaft 140, as well as prevents irrigation fluid from flowing out of the distal shaft component 150 in a proximal direction within the catheter shaft 140. The electrode advancer stylet 118 is desirably coated with a material, e.g., Teflon™ plastic, to break it loose from the adhesive bond 294, so that it can be advanced and retracted through the adhesive bond 294 to perform its intended function.

V. The Operative Element

Maintaining Desired Spacing Among the Arms

In using any of the foregoing representative embodiments of the operative element 16, 16', and 200, the objective is to produce a circumferential array of generally equally spaced lesions about the interior diameter of the targeted sphincter tissue region. It is possible that, upon expansion of the expandable structure 26, the basket arms 20/202 can inadvertently shift apart at unequal circumferential intervals. This phenomenon becomes more likely when the basket arms 20/202 possess smaller cross-sectional dimensions, and thus possess less mechanical stiffness. Basket arms with smaller cross-sectional dimensions are required in a basket structure that carries more electrode elements, and thus require more basket arms (which the foregoing embodiments make possible). Furthermore, when the electrode elements themselves are increasingly more firmly secured within the operative element (which the foregoing embodiments accomplish), inadvertent shifting of the basket arm may also cause inadvertent skewing of the electrode element.

Figure 29:
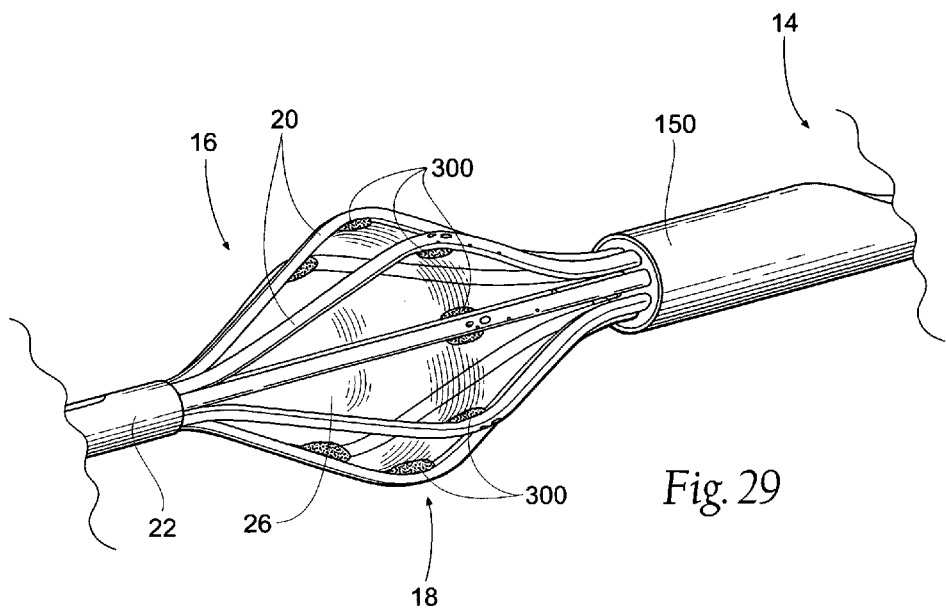
FIG. 29 is a perspective view of an operative element of the type shown in FIGS. 2A and 2C, and in which the arms of the basket are physically restrained from movement out of a desired circumferentially equally spaced array by the use of adhesive.

FIG. 29 shows one representative embodiment of an operative element 16 in which the arms 20 of the basket 18 are physically restrained from movement out of a desired circumferentially equally spaced array. In this embodiment, a flexible adhesive 300 bonds each arm to the underlying expandable structure 26. The adhesive 300 secures the basket arms 20 to the structure 26, to resist shifting of and to maintain a desired spacing among the basket arms 20 upon expansion of the structure 26.

Figure 30:
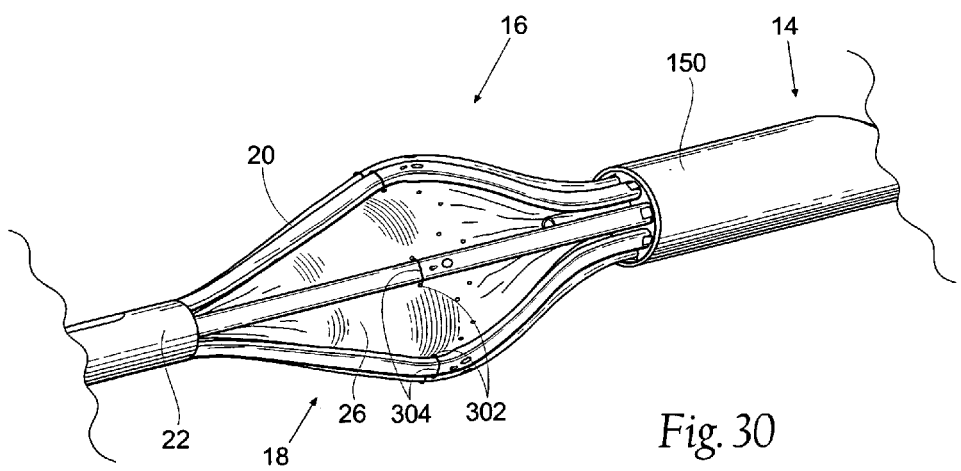
FIG. 30 is a perspective view of an operative element of the type shown in FIG. 11, and in which the arms of the basket are physically restrained from movement out of a desired circumferentially equally spaced array by the use of suture material.

In an alternative embodiment (see FIG. 30), the expandable structure 26 includes the already described irrigation openings 152, through which irrigation fluid F is dispensed (in the manner shown in FIG. 11). In this arrangement, additional openings 302 are formed in the structure 26 for the purpose of receiving suture material 304. The suture material 304 "ties" the basket arms 20 to the structure 26, to resist shifting of and maintain a desired spacing among the basket arms 20 upon expansion of the structure 26.

Figure 31:
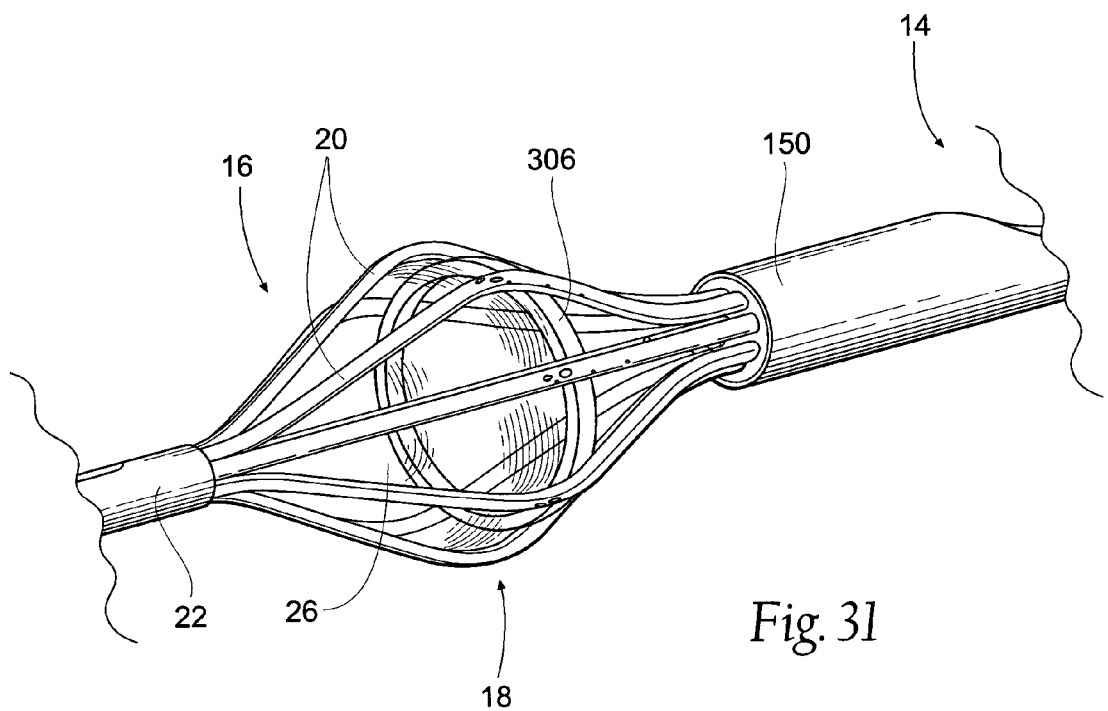
FIG. 31 is a perspective view of an operative element of the type shown in FIGS. 2A and 2C, and in which the arms of the basket are physically restrained from movement out of a desired circumferentially equally spaced array by the use of a resilient component.

In another alternative embodiment (see FIG. 31), an external resilient component 306 encircling the expandable structure 26 holds the basket arms 20 in the desired circumferentially spaced array during expansion and collapse of the structure 26. The resilient component 306 can take various forms.

In one arrangement, as shown in FIGS. 32A/B/C, the external component 306 comprises a formed elastomeric band 308, made, e.g., from molded silicone or santoprene. As FIG. 32B shows, the band 308 is, in use, positioned about the expandable structure 26 just proximal to (or, alternatively, just distal to) the openings 56 through which the electrode elements 28 exit the arms 20. The band 308 includes a circumferential array of arm support openings 310 (see FIG. 32A), through which the basket arms 20 pass (see FIG. 32B). The arm support openings 308 are formed to support the arms 20 in the desired circumferential spaced-apart array. The band 308 can be secured to the basket 18, e.g., by adhesive, to provide additional stability if desired.

It is to be understood that the elastomeric band 308 can be configured to support essentially any arrangement of arms 20. In the illustrated embodiment, eight openings 310 are spaced equidistant about the band 308. This arrangement accommodates a basket 18 having eight arms 20 that are also spaced equidistant. In one alternative embodiment, a greater or lesser number of openings 310 are spaced equidistant to accommodate a basket 18 having a corresponding number of equidistant-spaced arms 20.

In some cases, to produce a desired lesion pattern, it may be desirable to provide a basket 18 in which arms 20 are spaced in an irregular or non-equidistant spaced pattern. In this arrangement, openings 310 of band 308 can be spaced in a corresponding irregular or non-equidistant spaced pattern.

In the embodiment illustrated in FIGS. 32A-32C, the openings 310 are of a slightly elongated or oval configuration. It is apparent that the size and configuration of openings 310 can be varied to accommodate the specific configuration of arms 20 and/or to provide a desired fit (i.e., to provide the desired tension of arms 20 within the openings 310). For example, FIG. 32D illustrates an alternative embodiment in which the openings 310 are of an essentially round configuration.

In the embodiment illustrated in FIG. 32D, the band 308 is of a greater width (W) and depth (D) relative to the previous embodiment of FIGS. 32A-32C. It is contemplated that the band 308 can be varied in width, and depth to accommodate specific needs and/or to provide sufficient support for the basket arms 20.

As FIG. 32B shows, the band 306 has a normal, at rest interior diameter, which is less than the outside diameter of the expandable structure 26 when it is in its collapsed condition. As the structure 26 expands, the elastomeric band 308 resiliently stretches (see FIG. 32C), to conform to the increase in outside diameter of the structure 26. While stretching, the band 308 keeps the spacing between the arms 20 at the desired proportional intervals. The band 308 maintains proportionally consistent spacing between the basket arms 20 during expansion of the structure 26 and deployment of the electrode elements 28, regardless of the outside diameter for the structure 26. The band 308 also imparts mechanical stiffness to the arms 20 to resist twisting. The elastomeric memory of the band 308 further assists in ensuring complete collapse of the structure 26 and surrounding basket 18 following deployment of the electrode elements 28 (as FIG. 32B shows).

Figure 33A:
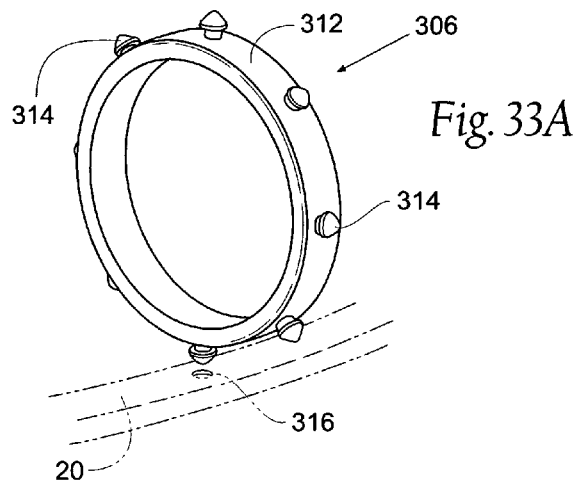
FIGS. 33A, 33B, and 33C are perspective views of an operative element of the type shown in FIG. 31, and in which the resilient component comprises an elastomeric ring.
Figure 33B:
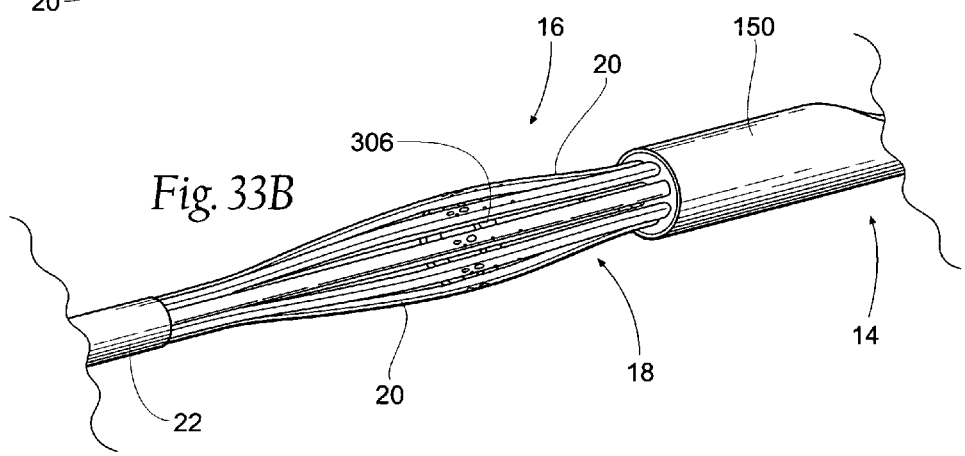

In another arrangement, as shown in FIGS. 33A/B/C, the external component 306 comprises a formed elastomeric ring 312, made, e.g., from molded silicone. As FIG. 33B shows, the ring 308 is, in use, positioned about the expandable structure 26 just proximal to (or, alternatively, just distal to) the openings 56 through which the electrode elements 28 exit the arms 20. The ring 308 includes a circumferential array of barbs 314 (see FIG. 33A), which snap fit into mating openings 316 formed on the interior surface of the basket arms 20 (see FIG. 33B). Once secured to all the basket arms 20, the ring 312 holds the arms 20 in a desired circumferential spaced-apart array.

Figure 33C:
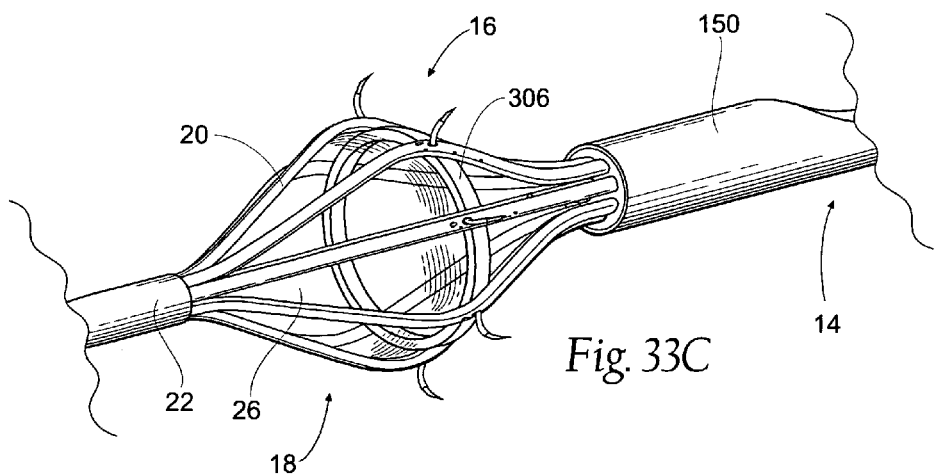

As FIG. 33B shows, like the band 306, the ring 312 has a normal, at rest interior diameter, which is less than the outside diameter of the expandable structure 26 when it is in its collapsed condition. As the structure 26 expands, the elastomeric ring 312 resiliently stretches (see FIG. 33C), to conform to the increase in outside diameter of the structure 26. While stretching, the ring 312 (like the band 308) keeps the spacing between the arms 20 at the desired proportional intervals. Like the band 308, the ring 312 maintains proportionally consistent spacing between the basket arms 20 during expansion of the structure 26 and deployment of the electrode elements 28, regardless of the outside diameter for the structure 26. The ring 312, like the band 308, also imparts mechanical stiffness to the arms 20 to resist twisting. Like the band 308, the elastomeric memory of the ring 312 further assists in ensuring complete collapse of the structure 26 and surrounding basket 18 following deployment of the electrode elements 28 (as FIG. 33B shows).

Figure 34A:
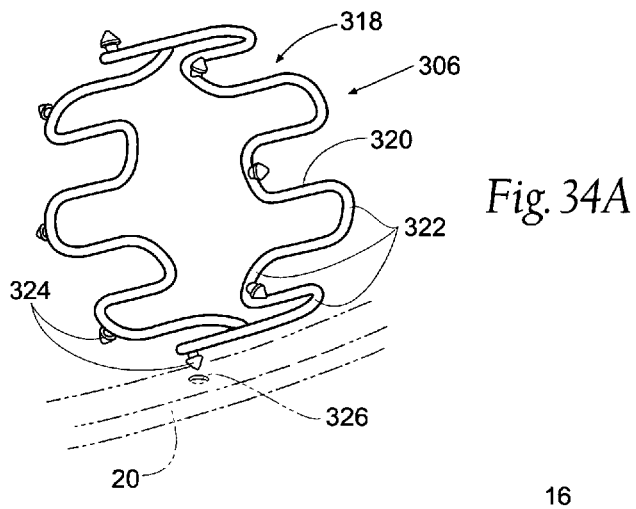
FIGS. 34A, 34B, and 34C are perspective views of an operative element of the type shown in FIG. 31, and in which the resilient component comprises a spring memory ring.

In another arrangement, as shown in FIGS. 34A/B/C, the external component 306 comprises a spring memory ring 318, which can, e.g., be fabricated from an injection molded plastic material, such as Peek™ material. The spring memory ring 318 is molded to comprise a main body 320 with undulating opposed curves 322. The curves 322 impart a plastic memory that allows resilient expansion of the body 320 from an at rest condition (shown in FIG. 34A), during which the curves 322 straighten out (see FIG. 34C), in response to an external expansion force. The plastic memory returns the body 320 to the at rest condition in the absence of an external expansion force.

Figure 34B:
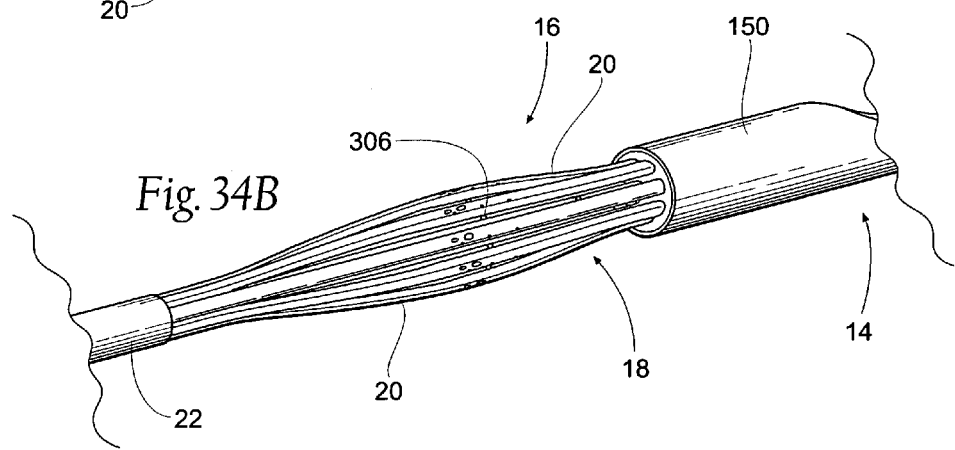
Figure 34C:
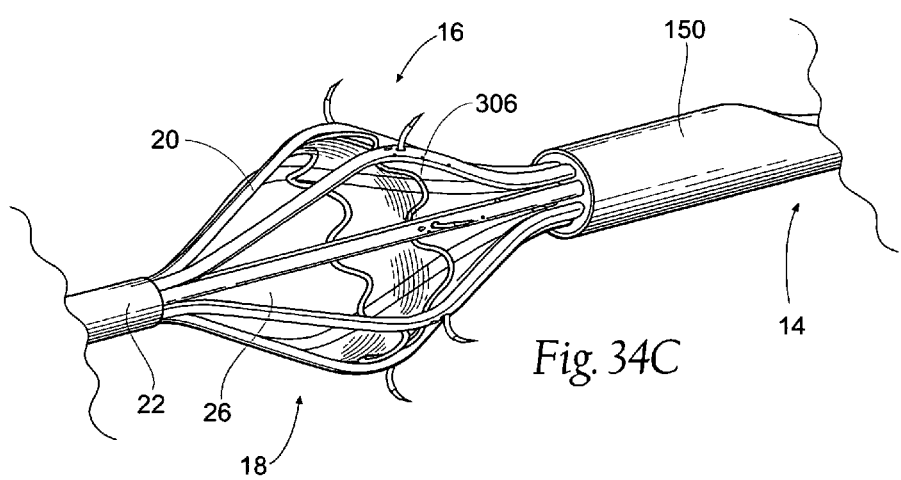

As FIG. 34B shows, the spring memory ring 318 is, in use, positioned about the expandable structure 26 just proximal to (or, alternatively, just distal to) the openings 56 through which the electrode elements 28 exit the arms 20. The spring memory ring 318 includes a circumferential array of barbs 324 (see FIG. 34A), which snap fit into mating openings 326 formed on the interior surface of the basket arms 20 (see FIG. 34B). Once secured to all the basket arms 20, the spring memory ring 318 holds the arms 20 in a desired circumferential spaced-apart array.

In its at rest condition (as FIG. 34B shows) the spring memory ring 318 has a normal, at rest interior diameter, which is less than the outside diameter of the expandable structure 26 when it is in its collapsed condition. When the curves 322 are fully straightened-out, the spring memory ring 318 has a maximum interior diameter equal to or less than the maximum outside diameter of the structure 26.

The structure 26 expands and imposes an external expansion force on the spring memory ring 318. The curves 322 of the spring memory ring 318 straighten out in response to this external force (see FIG. 33C), to accommodate the increase in outside diameter of the structure 26. As the curves 322 straighten out, the body 320 of the spring memory ring 318 (like the band 308 and the ring 312) keeps the spacing between the arms 20 at the desired proportional intervals. Like the elastomeric memory of the band 308 and ring 312, the spring memory of the ring 318 maintains proportionally consistent spacing between the basket arms 20 during expansion of the structure 26 and deployment of the electrode elements 28, regardless of the outside diameter for the structure 26. The spring memory ring 312, like the elastomeric band 308 and ring 312, also imparts mechanical stiffness to the arms 20 to resist twisting. Like the elastomeric memory of the band 308 and ring 312, the spring memory of the ring 312 further assists in ensuring complete collapse of the structure 26 and surrounding basket 18 following deployment of the electrode elements 28 (as FIG. 34B shows).

VI. The Operative Element with Tethered Endoscope

FIG. 35 shows an operative element 16 carried at the distal end of a catheter tube 14, of the type previously described. Like reference numbers are therefore assigned like structural elements.

Figure 37:
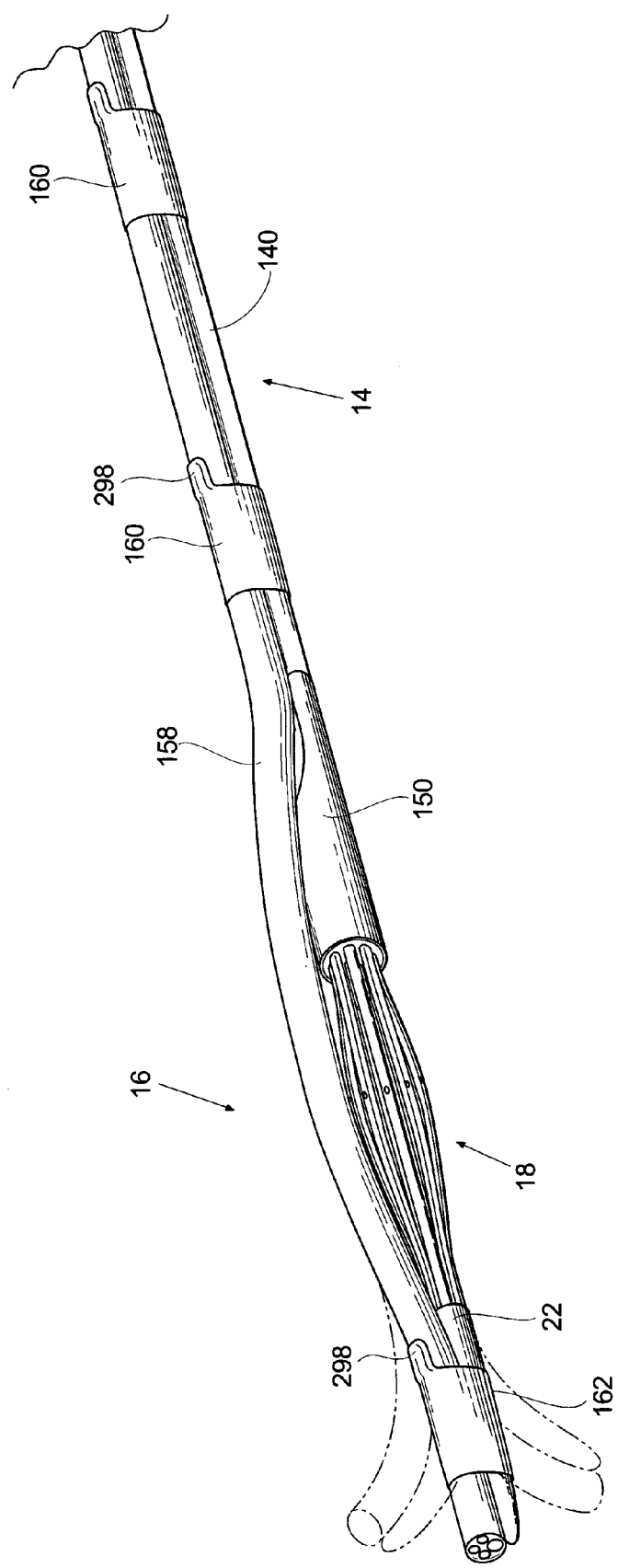
FIG. 37 is a perspective view of the operative element shown in FIG. 35, showing flexure of the tethered endoscope to provide a steering function for the operative element.
Figure 38:
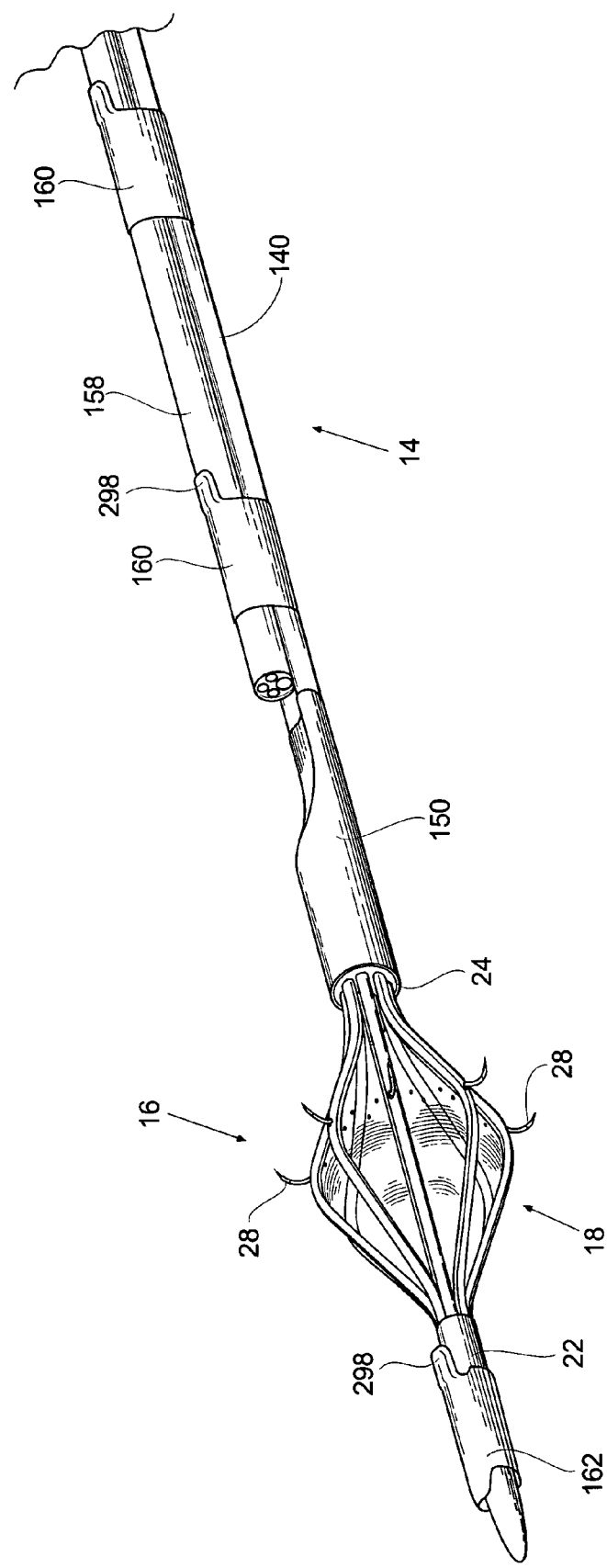
FIG. 38 is a perspective view of the operative element shown in FIG. 35, showing sliding movement of the endoscope during its tethered use with the operative element.

As previously described, the operative element 16 comprises a three-dimensional basket 18 having an expandable interior balloon structure 26 (see FIG. 38). The arms 20 of the basket 18 carry electrode elements 28, which can be retracted (as shown in FIG. 37) or extended (as shown in FIG. 38), for piercing tissue and applying ablation energy.

In the embodiment shown in FIG. 35, a visualization element or endoscope 158 is tethered to the catheter tube 14 and operative element 16. The endoscope 158 passes through more guide sheaths 160 on the extruded catheter shaft 140 proximal to the distal shaft component 150.

The guide sheaths 160 can be variously constructed. In the illustrated embodiment (see FIG. 36), the guide sheath 160 comprises a low durometer, molded elastomeric material, e.g., silicone. The guide sheath 160 desirably has a cross section that matches that of the catheter shaft 140, which, in the illustrated embodiment, is scalloped. A tab 298 can be provided on the guide sheath 160 to assist stretching of the guide sheath 160 open for insertion of the endoscope 158.

The tubular geometry of the endoscope 158 nests within the scalloped external configuration of the extruded shaft 140. As FIG. 35 shows, the scalloped configuration allows side-by-side ("piggy-back") deployment of the endoscope 158 on the catheter tube 14, while maintaining a minimized outside diameter.

As shown in FIG. 35, the endoscope 158 can extend over the operative element 16 (which is shown in its collapsed condition). The distal end of the endoscope 158 releasably rests in a distal guide sheath 162 on the distal tip 22. Secured to the distal tip 22 in this fashion (see FIG. 37), flexure of the distal end of the endoscope by operation of a conventional steering mechanism on-board the endoscope 158, also serves to flex or steer the distal extremities of the operative element 16 itself. The steerable endoscope 158, carried in tandem with the operative element 16, provides the operative element 16 with a steering function during its initial deployment.

Axially retracting the endoscope 158 serves to release the distal end of the endoscope 158 from the distal guide sheath 162. A lubricant is desirably applied to the endoscope 158, to enable the physician to readily slide the endoscope fore and aft along the catheter tube 14 within the proximal guide sheaths 160. The catheter tube 14 thereby serves as a deployment platform for the endoscope 158 itself. More particularly, the endoscope 158 be deployed but once alongside the catheter tube 14, to provide visualization support during deployment and use of the operative element 16 in a targeted tissue region.

Figure 39A:
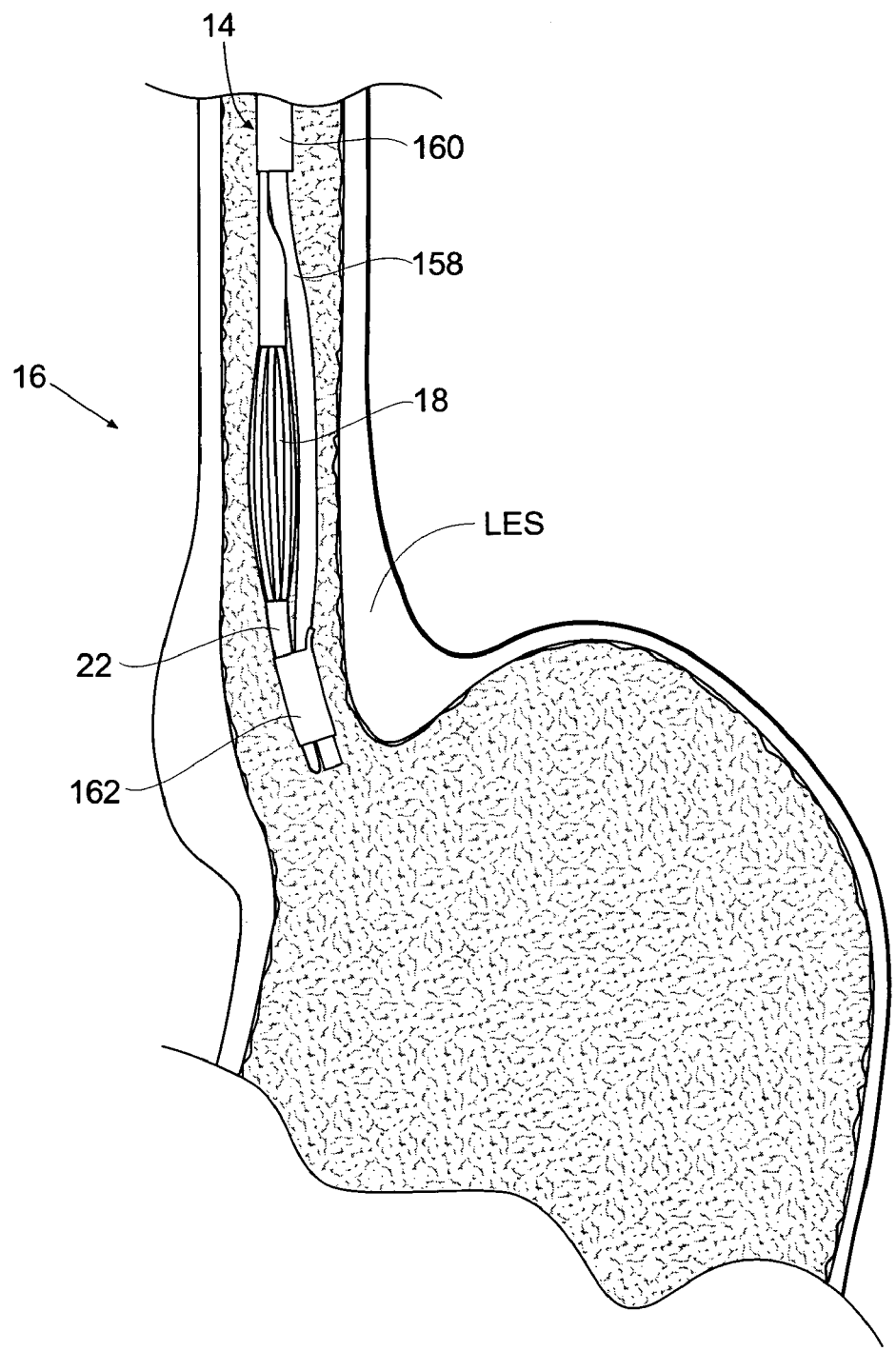
FIGS. 39A to 39E are a sequence of views illustrating the use of the operative element and tethered endoscope during a procedure that forms lesion patterns in or near the lower esophageal sphincter and cardia of the stomach for the treatment of gastro-esophageal reflux disease (GERD).

FIGS. 39A to 39E demonstrate the use and operation of the endoscope 158 and operative element 16 in a convenient, piggy-back fashion. The endoscope 158 is deployed along with the catheter tube 14 and operative element in the manner shown in FIG. 39A. FIG. 39A shows, for the purpose of illustration, the deployment of the operative element 16 at or near the lower esophageal sphincter (LES) for the purpose of treating GERD. In this arrangement, the operative element 16 is in its collapsed condition, and the endoscope 158 rests alongside the catheter tube 14 and over the operative element 16 within the proximal and distal guide sheaths 160 and 162. In this configuration, the distal regions of the operative element 16 can be deflected or steered, using the on-board steering capabilities of the endoscope 158 (as FIG. 37 also shows). In this configuration, the physician can use the visualization functions of the endoscope 158 to obtain proper position and alignment of the operative element 16 with the LES.

Figure 39B:
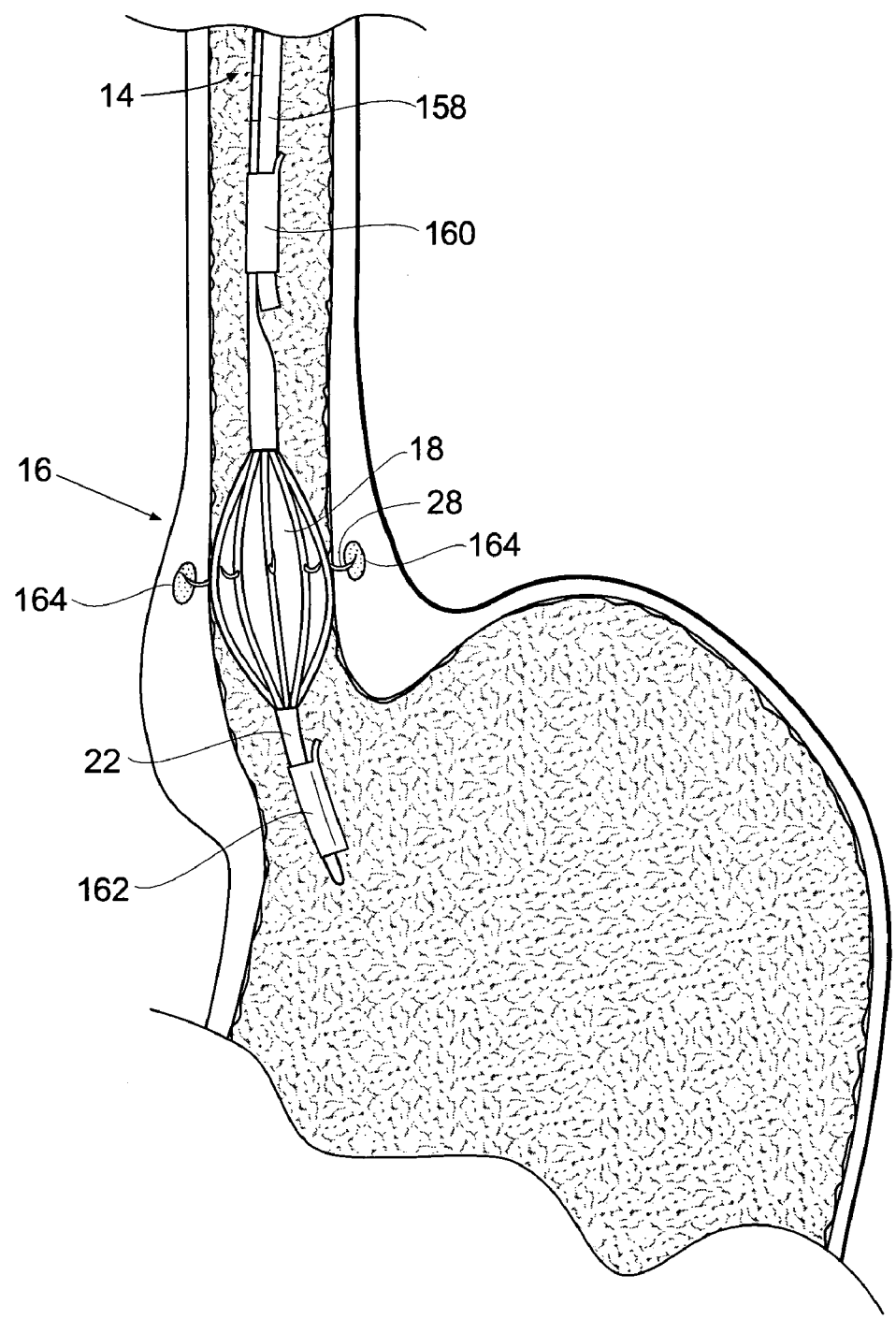

Once proper position and alignment are achieved (see FIG. 39B), the physician slides the distal end of the endoscope 158 free of the distal guide sheath 162. The physician slides the endoscope 158 further aft, proximally of the operative element 16 (as FIG. 39B shows). The physician can now expand the balloon structure 16 and extend the electrode elements 16 into piercing contact with tissue at or near the LES. Application of ablation energy forms lesions 164.

Figure 39C:
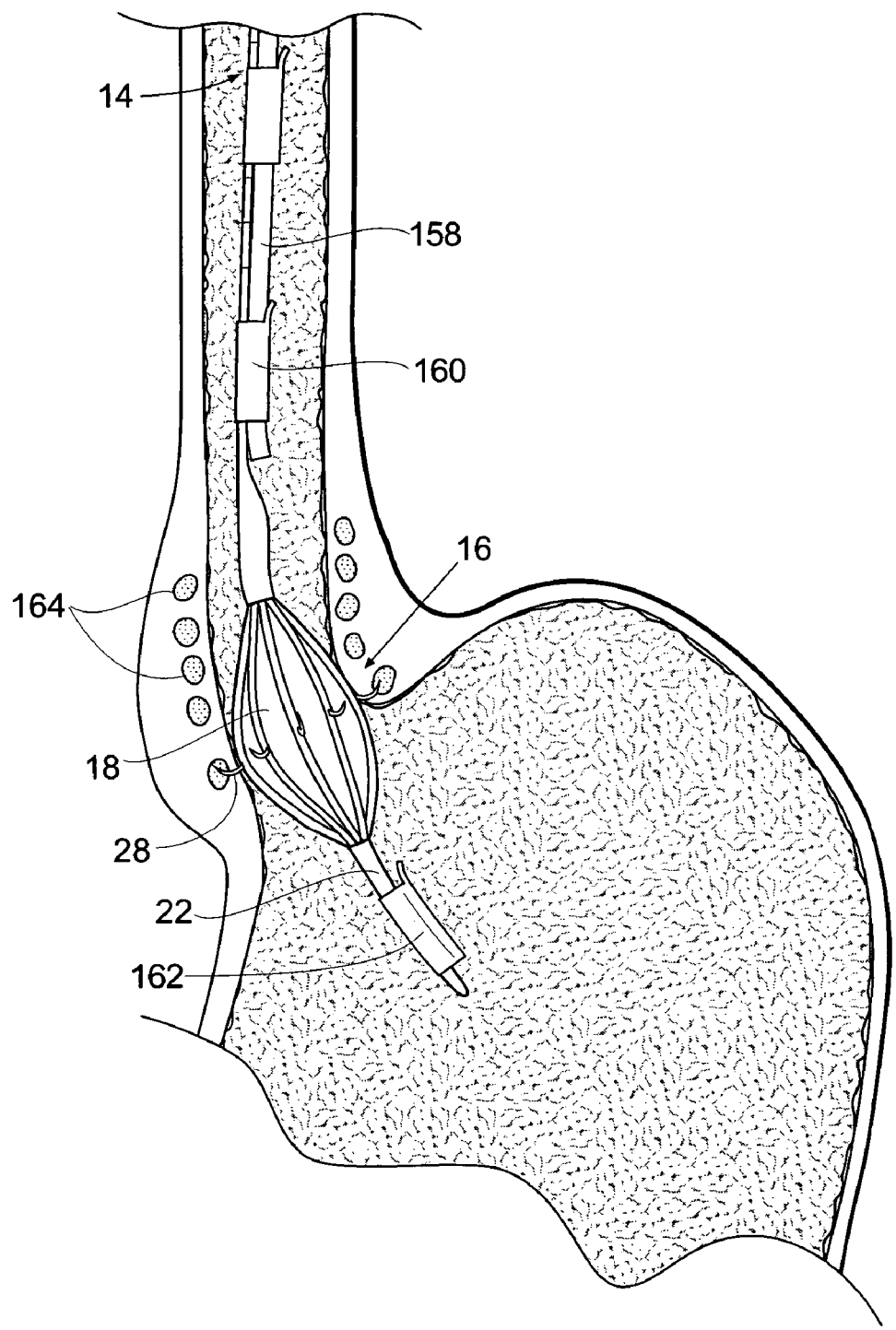
Figure 39D:
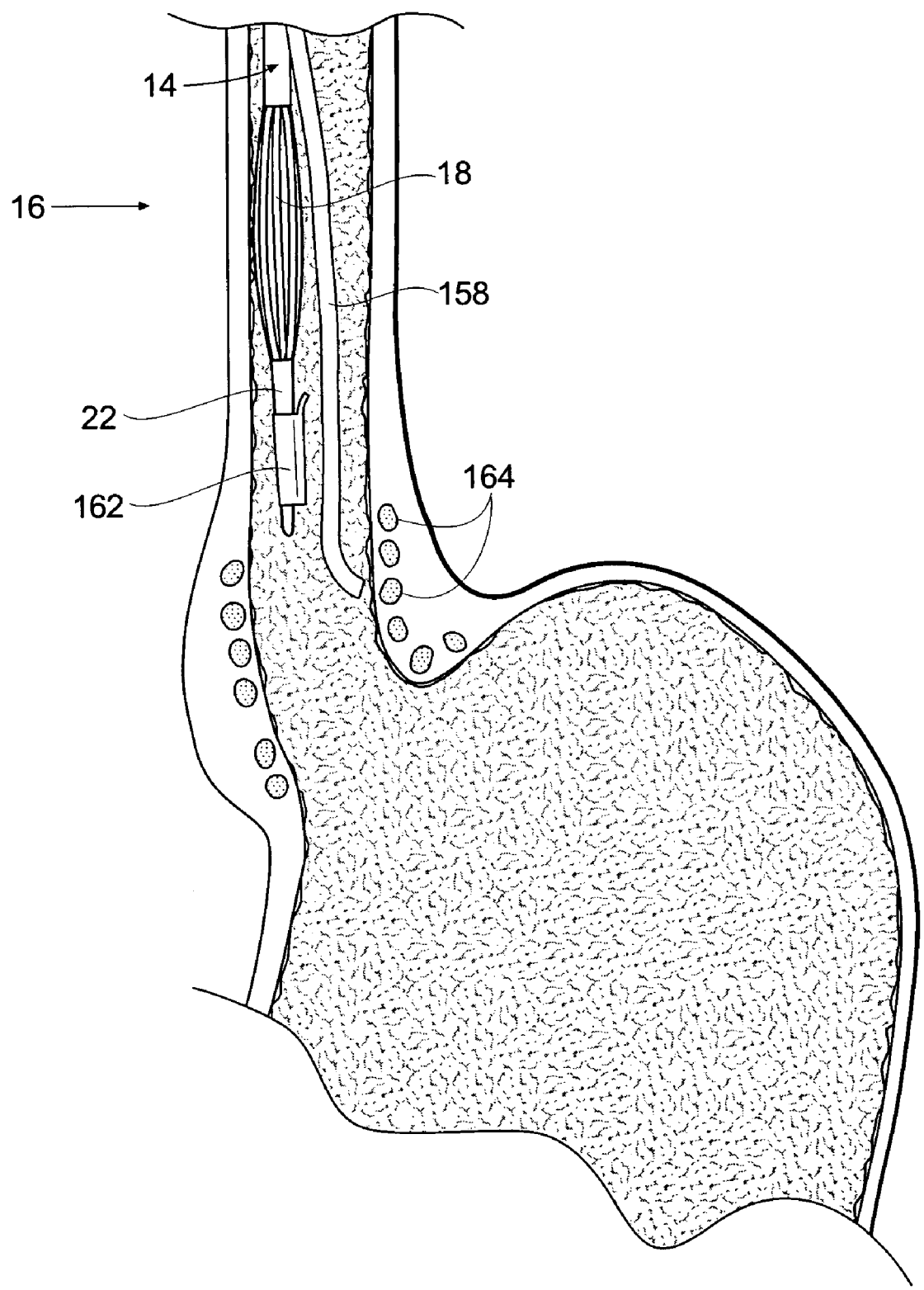
Figure 39E:
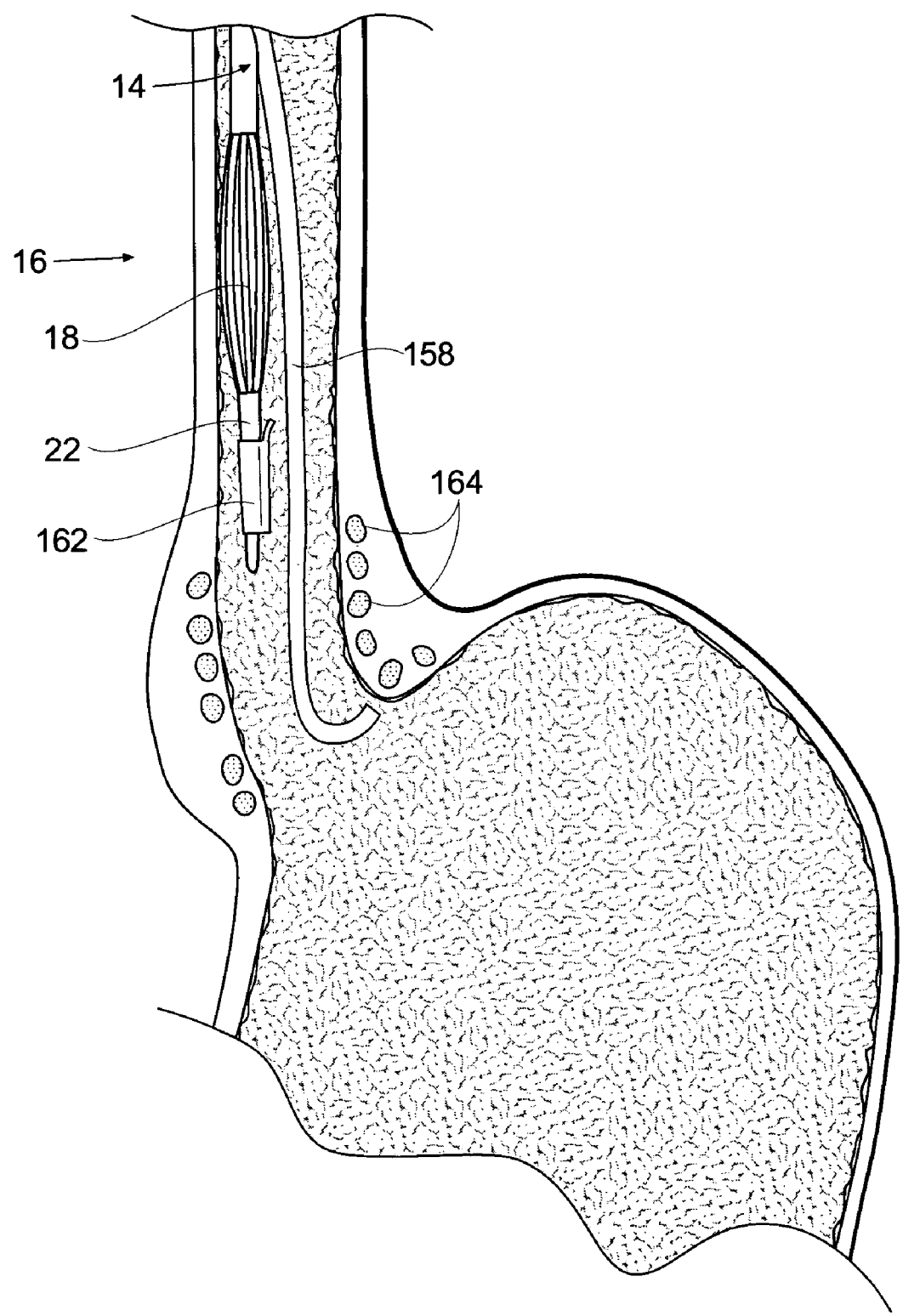

Retraction of the electrode elements 16 and collapsing of the balloon structure 16 allows the physician to reposition the operative element 16 and perform one or more additional ablation sequences (see FIG. 39C). In this way, the physician forms a desired pattern of circumferentially and axially spaced lesions 164 at or near the LES and cardia.

At any time during the ablation sequences, the physician can withdraw the operative element 16 from the targeted region. By sliding the endoscope 158 within the guide sheaths 160 along the catheter tube 16, the physician can position the distal end of the endoscope 158 to visualize the targeted tissue region at or near the LES (see FIG. 39D) or at or near the cardia (see FIG. 39E). Because the endoscope 158 is tethered to the catheter tube 16 throughout the procedure, the physician has continuous and immediate access and use of the endoscope 158 within the targeted tissue region. The endoscope 158 can be deployed but once at the beginning of a procedure, and need not be deployed, redeployed, positioned, and repositioned repeatedly during a given procedure.

FIG. 40 shows an alternative embodiment of an operative element 16 carried at the distal end of a catheter tube 14, in which a visualization element or endoscope 158 is tethered to the catheter tube 14 and operative element 16. In this embodiment, the endoscope 158 passes through a slot 328 integrally formed in the distal end of the tip 22 (see FIG. 41).

In this arrangement, the tip 22 is desirably formed from an elastomeric material, which permits the slot 328 to be resiliently stretched to accommodate passage of the endoscope 158. The integrated slot 328 obviates the need for a separate guide sheath 162 on the tip 22. In this arrangement, guide sheaths 160 for the endoscope 160 are still desirably provided on the extruded catheter shaft 140 proximal to the distal shaft component 150 (as shown in FIG. 40).

Figure 42:
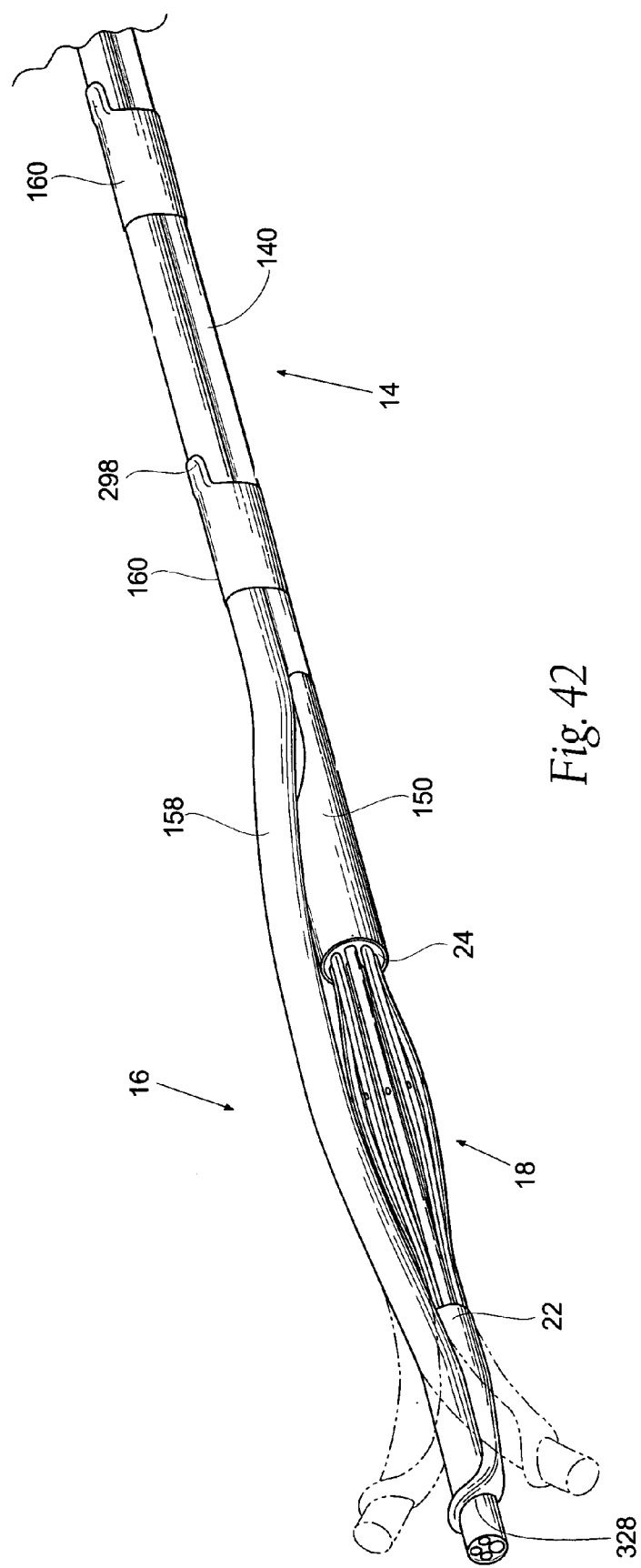
FIG. 42 is a perspective view of the operative element shown in FIG. 40, showing flexure of the tethered endoscope to provide a steering function for the operative element.
Figure 43:
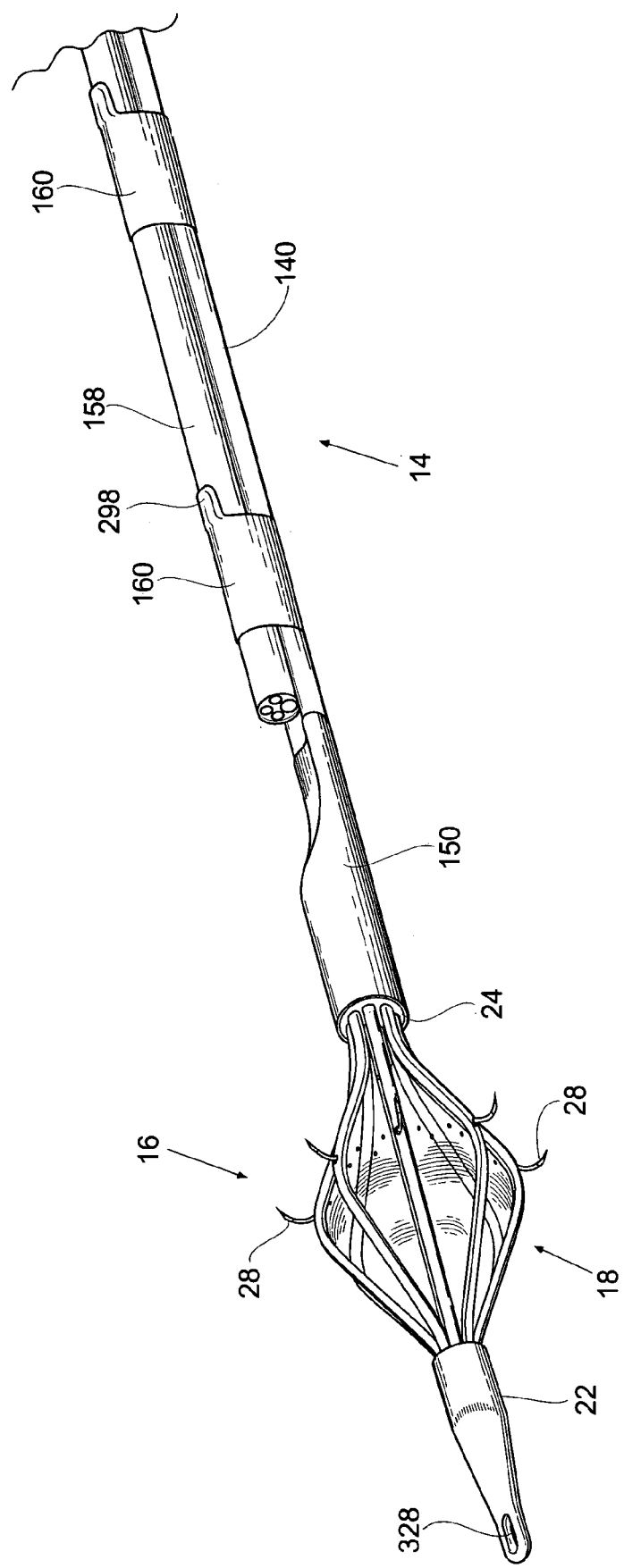
FIG. 43 is a perspective view of the operative element shown in FIG. 40, showing sliding movement of the endoscope during its tethered use with the operative element.

As shown in FIG. 40, the endoscope 158 can extend over the operative element 16 (which is shown in its collapsed condition). The distal end of the endoscope 158 releasably fits into the slot 328. Secured to the distal tip 22 in this fashion (see FIG. 42), flexure of the distal end of the endoscope by operation of a conventional steering mechanism on-board the endoscope 158, also serves to flex or steer the distal extremities of the operative element 16 itself. The steerable endoscope 158, carried in tandem with the operative element 16, provides the operative element 16 with a steering function during its initial deployment.

Axially retracting the endoscope 158 serves to release the distal end of the endoscope 158 from the slot 328 (as FIG. 38 shows). As before described, a lubricant is desirably applied to the endoscope 158, to enable the physician to readily slide the endoscope fore and aft along the catheter tube 14 within the proximal guide sheaths 160. Thus, in this arrangement, the catheter tube 14 still serves as a deployment platform for the endoscope 158 itself. More particularly, the endoscope 158 be deployed but once alongside the catheter tube 14, to provide visualization support during deployment and use of the operative element 16 in a targeted tissue region. The endoscope 158 and operative element 16 shown in FIG. 40 can be used and operated in the same convenient, piggy-back fashion shown in FIGS. 39A to 39E.

Figure 44:
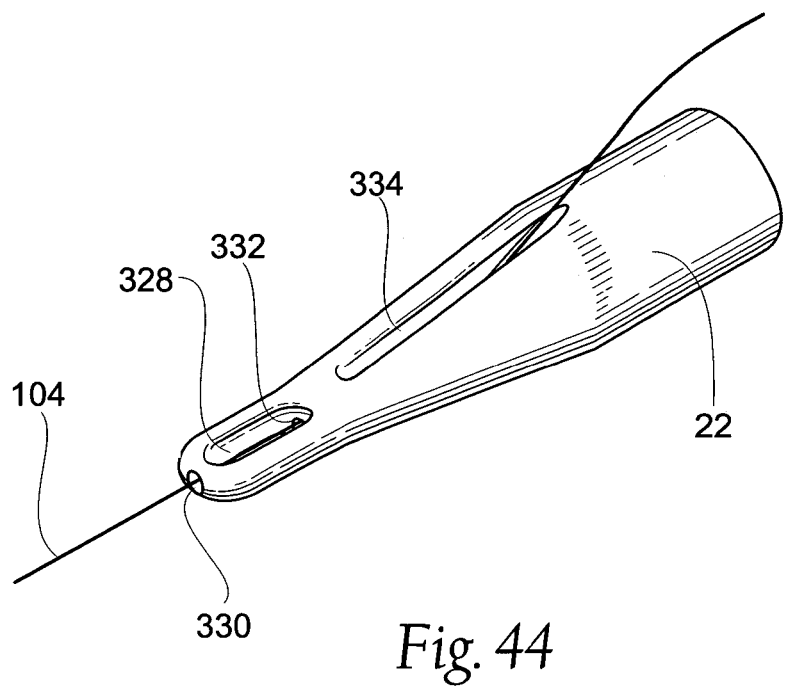
FIG. 44 is an enlarged perspective view of a slotted distal tip of the type shown in FIG. 41 to accommodate passage of an endoscope, and further showing additional tracking passages that accommodate passage of a guide wire in the absence of an endoscope.
Figure 45:
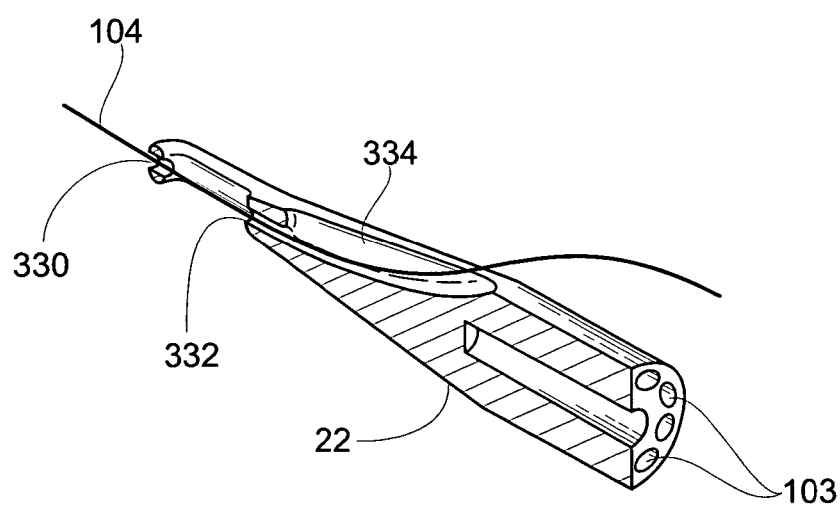
FIG. 45 is a side sectional view showing the interior of the guide wire tracking passages that the slotted distal tip shown in FIG. 44 includes.

In the absence of the endoscope 158, the slotted tip 22 shown in FIG. 40 can be used to accommodate passage of a guide wire 104. This is shown in FIG. 44. Desirably, the tip 22 includes additional tracking passages through which the guide wire 104 can pass. As shown in FIGS. 44 and 45, the additional tracking passages can include a tracking passage 330 at the distal end of the slot 328 and a tracking passage 332 at the proximal end of the slot 328. A guide wire entry passage 334 (see FIG. 45) in the tip 22 aligned with the tracking passage 332, also desirably directs the guide wire 104 into and through the slot 328 (through the tracking passages 330 and 332).

Figure 46:
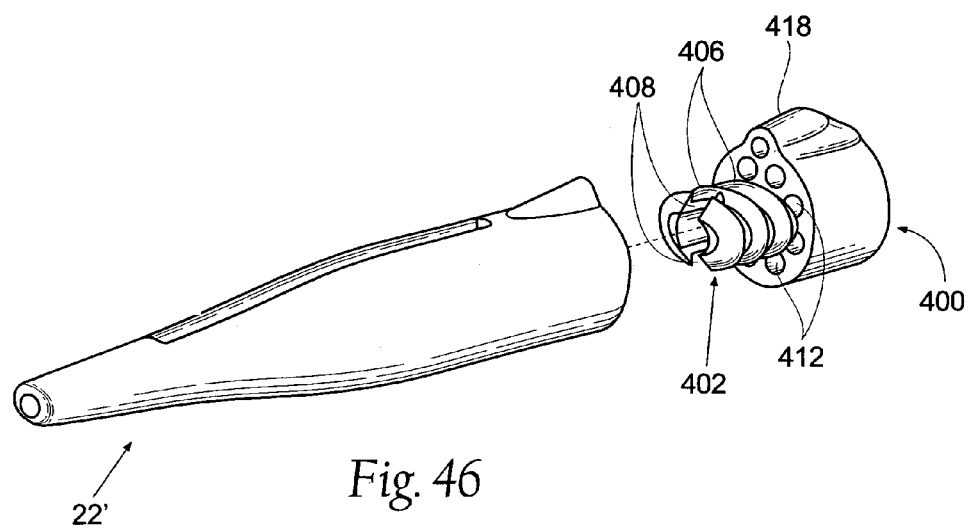
FIG. 46 is an exploded view of an alternative embodiment of a catheter distal tip assembly that accommodates passage of a guide wire in which the distal tip is coupled to a catheter tip base by an intermediate connector.
Figure 47:
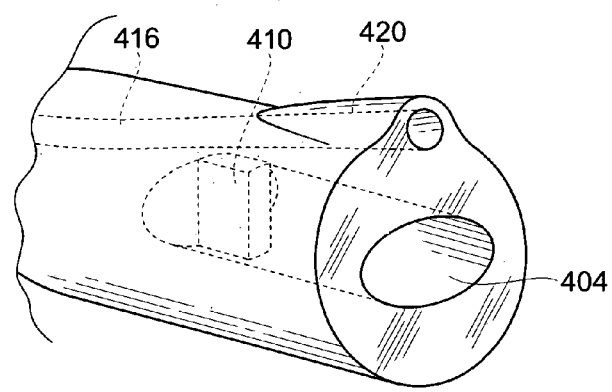
FIG. 47 is partial perspective view of the distal tip shown in FIG. 46 and illustrating a guidewire lumen and an elliptical-shaped opening adapted to receive the intermediate connector in phantom.
Figure 48:
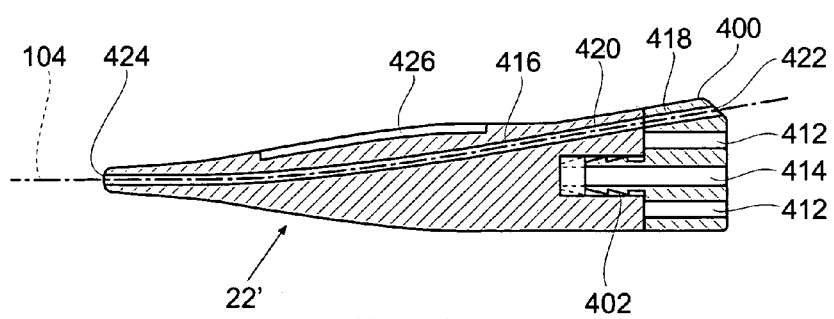
FIG. 48 is a side sectional assembled view of the catheter tip assembly taken along line 48-48 of FIG. 46.

FIGS. 46-48 illustrate an alternative embodiment of a catheter distal tip assembly providing a distal tip 22' suitable for use in the absence of an endoscope. The distal tip 22' may be conventional, formed, e.g., from semi-rigid, medical grade plastic (e.g., Pebax™ plastic material, polyurethane, silicone, Santoprene™ plastic material, Kraton™ plastic material, or other flexible materials) by conventional molding or machining techniques.

Distal tip 22' is desirably sized and configured to mate with a catheter tip base 400, e.g., in a male-female coupled fitting arrangement, to form a catheter tip assembly that provides a smooth transition from the relatively stiff basket assembly to the flexible distal tip 22'.

In the illustrated embodiment, catheter tip base 400 carries or is coupled to an intermediate connector 402. Distal tip 22' includes an opening 404 sized and configured to receive the intermediate connector 402 to couple the distal tip 22' to the catheter tip base 400. The opening 404 and the intermediate connector 402 are desirably sized and configured to provide a secure fit and prevent rotation of the connector 402 within the tip 22'.

For example, in the illustrated embodiment, the intermediate connector 402 is of a generally elliptical configuration and provides a series of ribs or barbed ends 406 that mate with a complementary elliptical-shaped opening 404 in the distal tip 22' to permit mechanical attachment of the base 400 to the distal tip 22'. A pair of slots 408 in barbs 406 mate with a boss 410 within the opening 404 of tip 22' to secure the connector 402 and prevent rotation of the connector 402 within the tip 22'. The barbs 406 and boss 410 form a strong mechanical joint that can be further secured, e.g., with UV-cured adhesive.

The catheter tip base 400 is desirably formed from a rigid molded or machined plastic, e.g., polycarbonate or Peek™ plastic material.

The catheter tip base 400 preferably includes a series of lumens 412 for receiving and collectively joining the distal ends of the extruded basket arms 20, thereby serving as a rigid spine to receive the basket 18. The base 400 desirably also includes a lumen 414 for receiving the distal end of the balloon structure 26. The arms 20 and the distal end of the balloon structure 26 can be secured to the base 400, e.g., by adhesive bonding or by snap-fit engagement.

The guide wire 104 is threaded through a lumen 416 extending through the catheter tip base 400 and the distal tip 22'. The interior lumen 416 comprises a first tracking passage 418 extending through the catheter tip base 400 and a second tracking passage 420 extending through the distal tip 22'. The interior lumen 416 extends between an proximal opening 422 in the catheter tip base 400 and a distal opening 404 in the distal tip 22'. This arrangement provides a low entry angle for the guide wire 104, desirably approximately 10°. This arrangement also provides containment of the guide wire 104 at both the proximal and distal ends of the guide wire lumen 416, thereby reducing the likelihood of "S-curve" type bending of the guide wire 104 during passage through the lumen 416. A slot or groove 426 in the distal tip 22' aids in positioning the device during insertion, as illustrated in FIG. 48.

Figure 49:
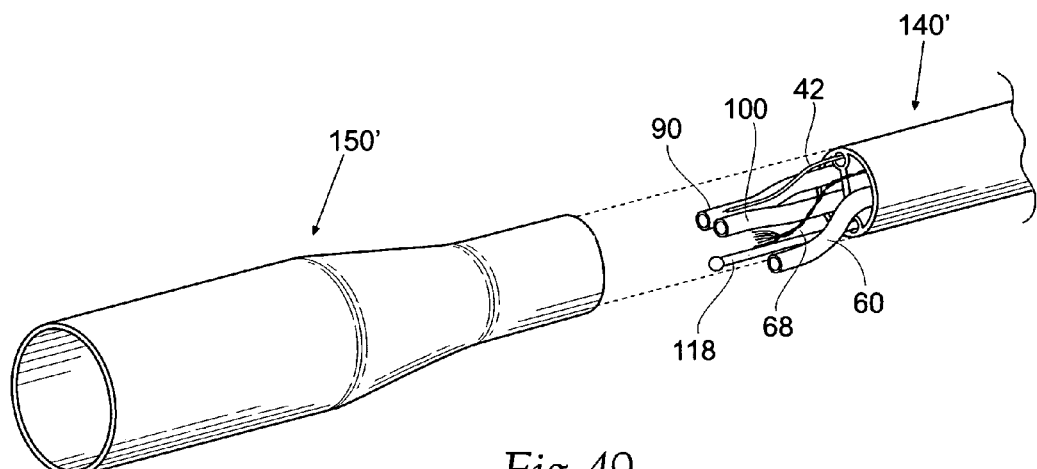
FIG. 49 is an exploded perspective view of an alternative embodiment of the catheter shaft and catheter distal end component shown in FIG. 1 in which the catheter shaft and distal end component are of an essentially rounded configuration.
Figure 50:
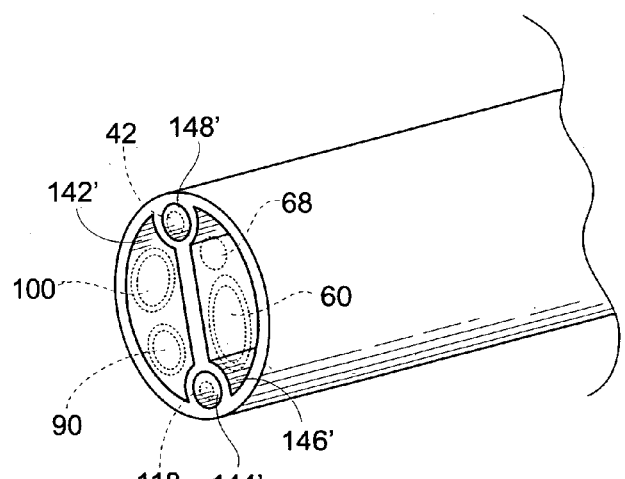
FIG. 50 is a close-up perspective view of the catheter shaft shown in FIG. 49 and illustrating the arrangement of interior lumens within the catheter shaft.

FIGS. 49 and 50 illustrate an alternative embodiment of a catheter shaft 140' presenting an essentially rounded, non-scalloped profile suitable for use in the absence of an endoscope. The co-extruded lumens 142'-148' in the shaft 140' accommodate passage of the various components that, in use, couple to the operative element 16.

More particularly, one co-extruded lumen 142' accommodates passage of the aspiration tube 100 and the balloon inflation tube 90. A second co-extruded lumen 144' accommodates passage of the electrode advancer stylet 118. A third co-extruded lumen 146' accommodates passage of the irrigation tube 60 and the bundle 68 of thermocouple wires. A fourth co-extruded lumen 148' accommodates passage of the electrode supply wires 42. As best seen in FIG. 50 the second and fourth lumens 144' and 148' are desirably off-center to provide alignment of the electrode advancer stylet 118 and electrode supply wires 42 with the needle advancer assembly 58.

Shaft 140' couples to distal shaft component 150'.

The distal shaft component 150' can be molded or reformed and is sized and configured at its proximal end to engage the terminus of the extruded catheter shaft 140' in a frictional slide-fit.

VII. Alternative Embodiment

Figure 51:
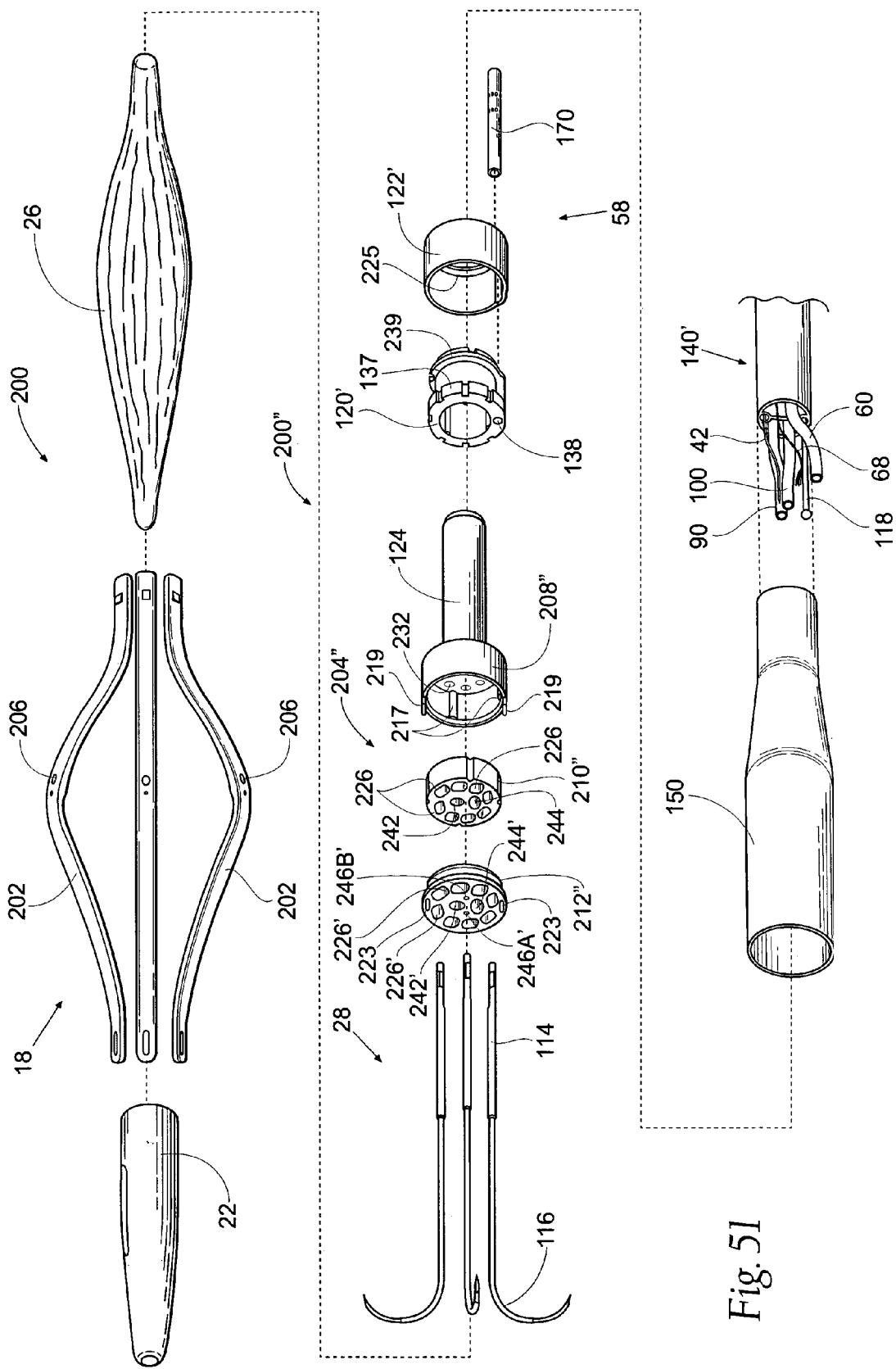
FIG. 51 is an exploded perspective view of the components of another embodiment of an operative element providing for cooling of surface tissue by "direct irrigation that can be used in association with the treatment device shown in FIG. 1.

FIG. 51 shows another alternative embodiment of an operative element 200" that enables direct irrigation. Operative element 200" is similar to operative element 200' previously described, and therefore like reference numbers will be used to indicate like components. Previous descriptions of structural elements having the same reference number are incorporated herein.

In the illustrated embodiment, closure wall 216 is eliminated such that interior passage 214 extends through the proximal end of the stem 124 to provide a single lumen at the proximal end of the stem 124.

The base element 204" differs in certain respects from the previously described base elements 204 and 204'. Chamber 208" includes a series of internal ribs 217 and external bosses 219 for engaging the irrigation seal 210" and the irrigation seal cap 212". The internal ribs 217 are positioned along the inner circumferential margin of the chamber 208" and are sized and configured to engage a series of complementary circumferential or external grooves 221 on the irrigation seal 210". This arrangement provides a keying system to properly orient the chamber 208" and the seal 210". External bosses 219 are sized and configured to engage a series of complementary slots 223 on the irrigation seal cap 212", providing an additional keying system to properly orient the chamber 208", the seal 210", and the cap 212". In the illustrated embodiment, four equidistant-spaced ribs 217 engage four equidistant-spaced grooves 221 and two equidistant-spaced external bosses 219 engage two equidistant-spaced slots 223. It is apparent that the number, configuration, and spacing of ribs 217, grooves 221, bosses 219, and slots 223 can be varied to provide different keying arrangements.

Needle advancer hub 120' is similar to hub 120 previously described. Hub 120' is desirably of an essentially rounded configuration as opposed to the slightly octagonal configuration of hub 120. External ribs 137 are preferably of a decreased length with respect to the previously described hub 120. The proximal end of the hub 120' includes a collet 239. The collet 239 engages the sleeve 122' to couple the hub 120' to the sleeve 122' in a snap fit engagement.

Sleeve 122' is similar in configuration to sleeve 122 previously described. The proximal end of the sleeve 122' desirably includes a chamfer 225 on the internal edge to facilitate installation of the sleeve 122' over the proximal ends of the needles 28. The sleeve 122' can be loaded onto the hub 120' from the proximal end after the needles 28 and stylet 118 have been installed.

Hub 120' and sleeve 122' are secured together by means by snap-fit, instead of by crimping of the hypotube 170 onto the stylet 118. A hypotube 170 is desirably still provided to secure the stylet 118 to the hub 120.

We claim:

1. A catheter assembly comprising an elongated member, a basket assembly carried by the elongated member including a first arm and a second arm,
an expandable balloon structure positioned in an interior of the basket assembly and having a collapsed condition in which the first and second arms of the basket assembly are collapsed in a collapsed outside diameter about the expandable balloon structure and an expanded condition urging the first and second arms of the basket assembly to open and expand to an expanded outside diameter greater than the collapsed outside diameter to exert an opening force upon tissue surrounding the basket assembly, and
a formed elastomeric band including a circumferential array of first and second arm support openings through which the first and second arms pass to support the first and second arms a desired circumferentially-spaced array, the elastomeric band including elastomeric memory having a normal, at rest interior diameter less than the collapsed outside diameter of the basket assembly to collapse the first and second arms about the expandable balloon structure when the expandable balloon structure is in the collapsed condition, the elastomeric band resiliently stretching to conform to an increase in outside diameter as the basket assembly opens and expands toward the expanded outside diameter, the first and second arm support openings of the elastomeric band maintaining the first and second arms in the desired circumferentially-spaced array during expansion of the basket structure.

2. An assembly as in claim 1 wherein the elastomeric band comprises silicone.

3. An assembly as in claim 1 wherein the elastomeric band imparts a mechanical stiffness to resist twisting of the first and second arms.

4. An assembly as in claim 1 further including at least one tissue-penetrating electrode carried in each of the first and second arms for sliding movement between a retracted position withdrawn in the respective arm and an extended position extending outward of the respective arm.

* * * * *